(12) United States Patent
Nigam et al.

(10) Patent No.: US 11,004,539 B2
(45) Date of Patent: May 11, 2021

(54) PREDICTING METABOLIC SIDE EFFECTS OF TRANSPORTED DRUGS

(71) Applicant: The Regents of the University of California, Oakland, CA (US)

(72) Inventors: Sanjay K. Nigam, Del Mar, CA (US); Henry C. Liu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1116 days.

(21) Appl. No.: 15/436,567

(22) Filed: Feb. 17, 2017

(65) Prior Publication Data
US 2017/0241043 A1    Aug. 24, 2017

Related U.S. Application Data

(60) Provisional application No. 62/296,981, filed on Feb. 18, 2016.

(51) Int. Cl.
G16B 5/00     (2019.01)
G16B 35/00    (2019.01)
G16C 20/60    (2019.01)

(52) U.S. Cl.
CPC .............. *G16B 35/00* (2019.02); *G16B 5/00* (2019.02); *G16C 20/60* (2019.02)

(58) Field of Classification Search
None
See application file for complete search history.

(56) References Cited

U.S. PATENT DOCUMENTS 6,680,302 B2 * 1/2004 Seidman .................. A61P 1/00
                                                          514/45

OTHER PUBLICATIONS

Ahn etal (JBC 286:31522-31) (Year: 2011).*
Duan et al (Mol. Pharmaceutics 9: 3340-3346) (Year: 2012).*
Ahn et al., "Interaction of Organic Cations with Organic Anion Transporters," J of Biol. Chem., 284(45):31422-31430, 2009.
Kaler et al., "Structural Variation Governs Substrate Specificity of Organic Anion Transporter (OAT) Homologs," J. of Biol. Chem., 282(33):23841-23853, 2007.
Kouznetsova et al., "Elucidation of common pharmacophores from analysis of targeted metabolites transported by the multispecific drug transporter-Organic anion transporter) (OAT1)," Bioorg Med Chem., 19(11):3320-3340, 2011.
Truong et al., "Multi-level Analysis of Organic Anion Transporters 1, 3, and 6 Reveals Major Differences in Structural Determinants of Antiviral Discrimination," J. of Biol. Chem., 283(13):8654-8663, 2008.
Wikoff et al., "Key structural features for substrate binding to organic anion transporter 1(Oat1; slc22a6) identified by global untargeted metabolomics of Oat1null plasma," J. Proteome Res., 10(6):2842-2851, 2011.

* cited by examiner

*Primary Examiner* — Christopher M Gross
(74) *Attorney, Agent, or Firm* — Gavrilovich, Dodd & Lindsey LLP

(57) ABSTRACT

Provided are drug-transport metabolomics profile assessments and therapies.

7 Claims, 36 Drawing Sheets

A

| Prediction | # Reactions & metabolites predicted to change |
|---|---|
| Total reactions | 1026 |
| Exchange/transport reactions | 321 |
| Metabolites predicted to be altered in transport | 177 |
| GEM-predicted metabolites (excluding water, ATP, etc.) | 146 |

B

| Metabolites identified by previous targeted and untargeted metabolomics and are also present in iMM1415 BiGG Database | Altered in urine/plasma? | Predicted to change |
|---|---|---|
| 3-Hydroxybutyrate | yes | yes |
| 4-Hydroxyphenyllactate | yes | yes |
| 3-Hydroxypropionate | yes | yes |
| 4-Hydroxyphenylacetate | yes | yes |
| Orotate | yes | yes |
| 4-Hydroxyphenylpyruvate | yes | yes |
| alpha-Ketoglutarate | yes | yes |
| Urate | yes | yes |
| Uracil | yes | yes |
| N-Acetylaspartate | yes | yes |
| Benzoate | yes | -- |
| 3-Hydroxyisobutyrate | yes | -- |
| 2-Oxo-3-methylvalerate | yes | -- |
| 2-Oxoisocaproate | yes | -- |
| Pantothenic acid | yes | -- |
| 4-Pyridoxic acid | yes | -- |
| Kynurenine | yes | -- |
| Methionine | yes | -- |
| Thymidine | yes | -- |

FIGURE 2A-B

| Novel OAT1 ligands | Measured $K_i$ ($\mu M$) | Metabolic pathways |
|---|---|---|
| Prostaglandin E1 | 12 | Arachidonic acid metabolism |
| Dihydrofolic acid | 93 | Folate biosynthesis |
| Palmitoleic acid | 200 | Fatty acid metabolism |
| 16-Hydroxy-hexadecanoic acid | 13 | Fatty acid metabolism |

FIG. 4B

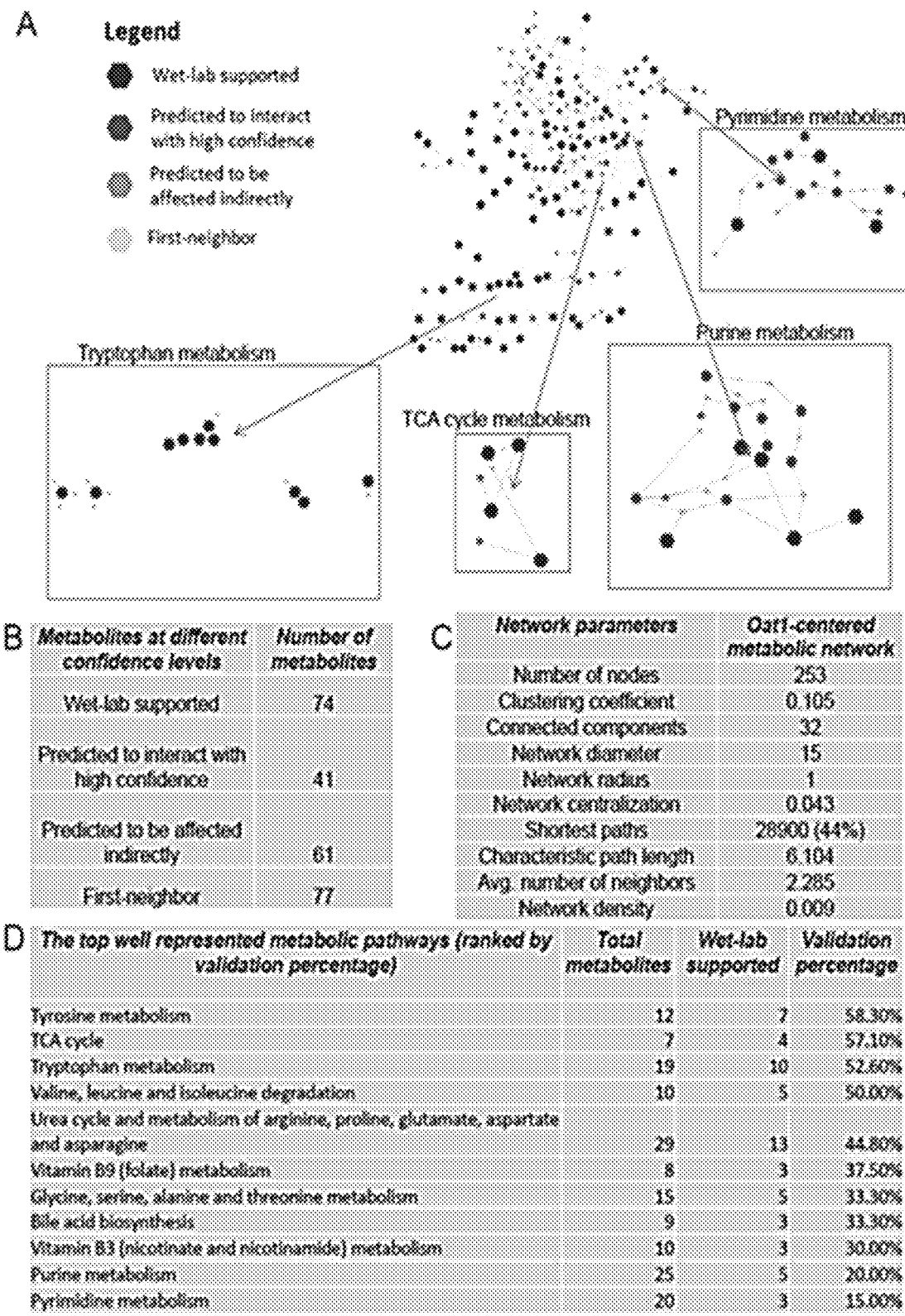
FIGURE 5A-D

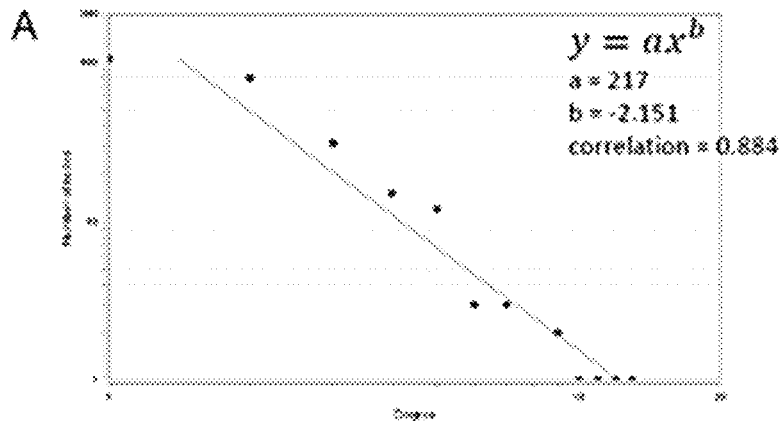
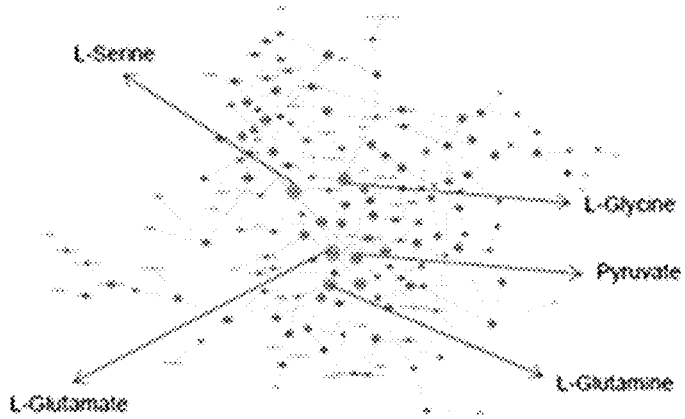
FIGURE 6A-D

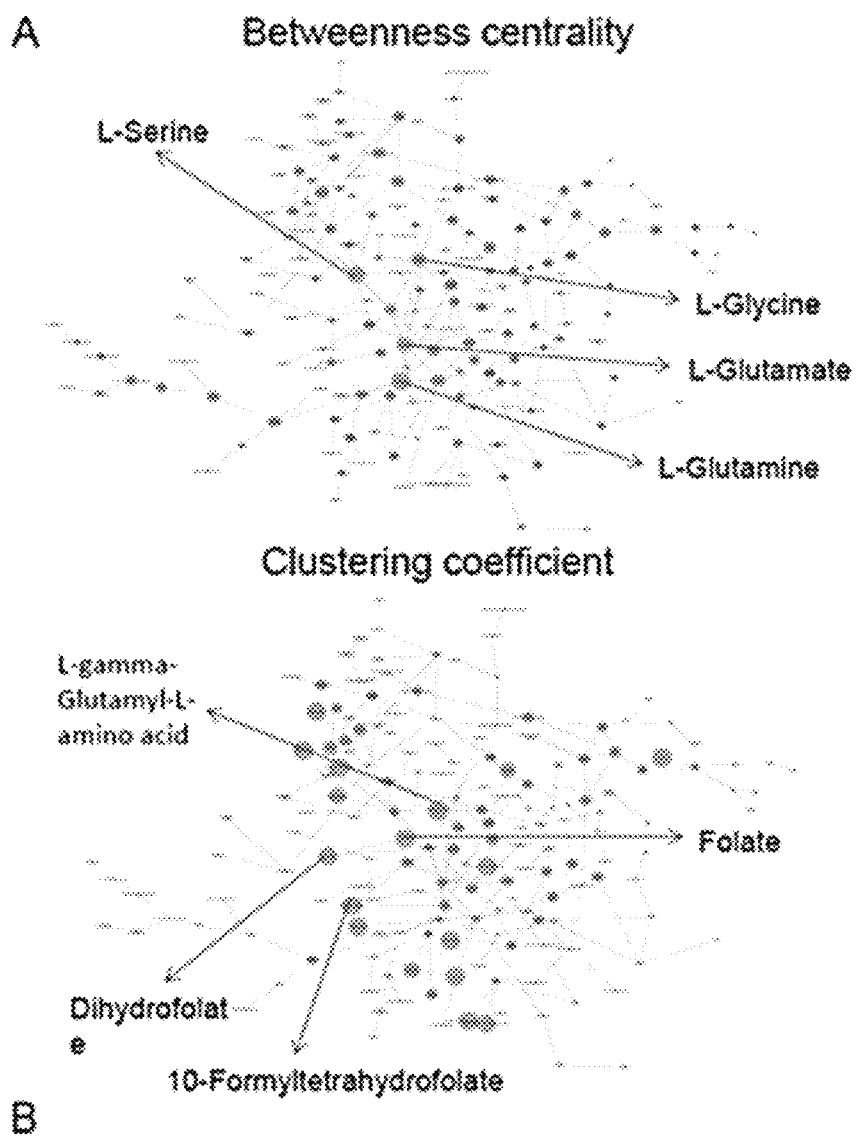
FIGURE 7A-B

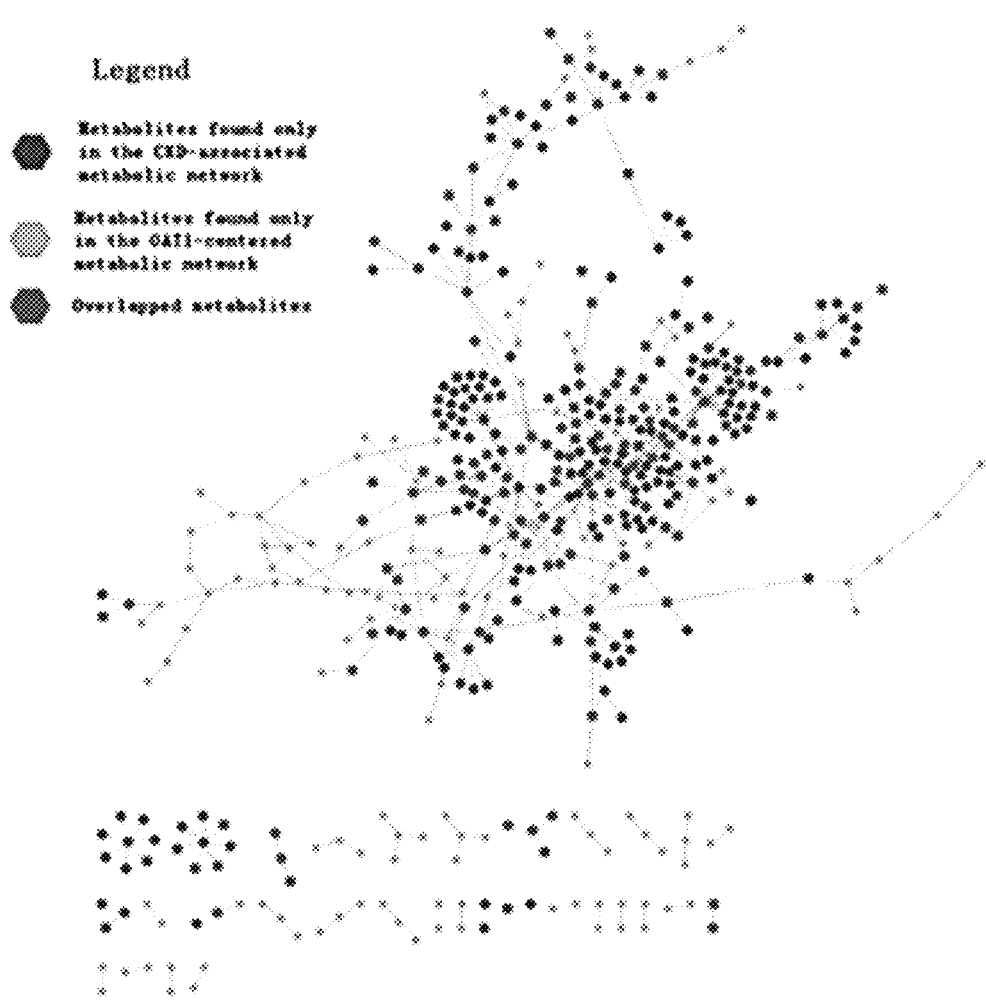
FIGURE 8A-B

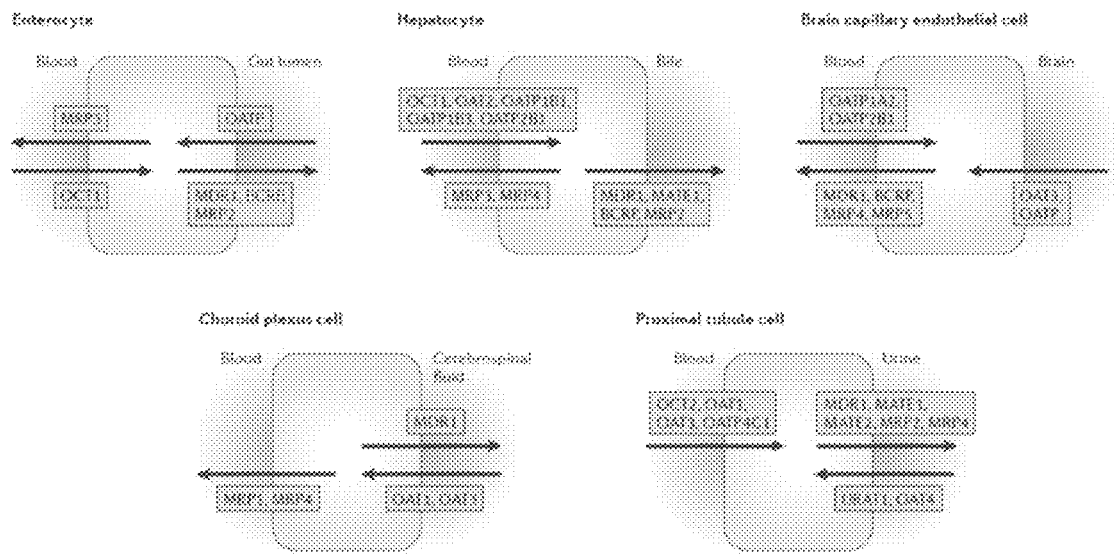
FIGURE 9
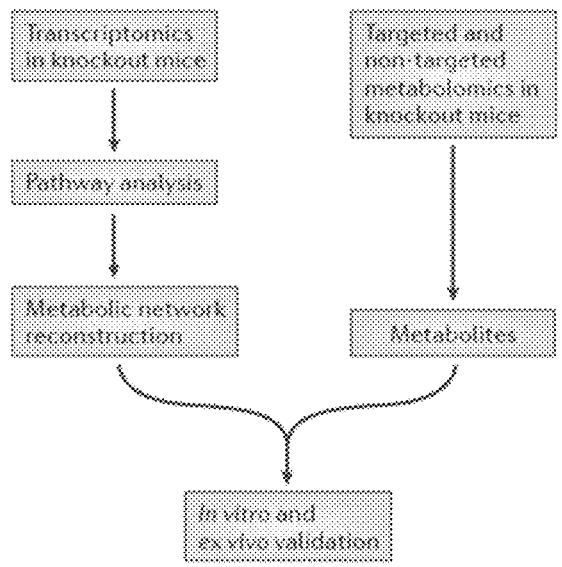
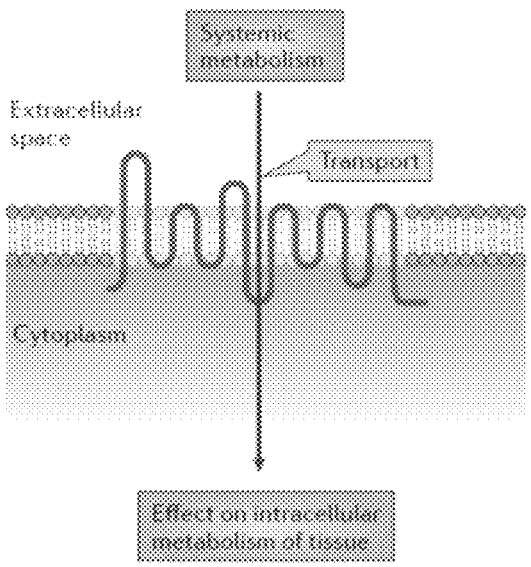
FIGURE 10A-B

OAT1 vs. OCT1

OAT3 vs. OCT1

OAT1 vs OAT3

OCT1 vs OCT2

| Top well-represented metabolic pathways | Average Degree |
|---|---|
| TCA cycle | 3.7 |
| Tyrosine metabolism | 2.1 |
| Urea cycle and metabolism of arginine, proline, glutamate, aspartate and asparagine | 4.3 |
| Tryptophan metabolism | 3.5 |
| Vitamin B3 (nicotinate and nicotinamide) metabolism | 3.0 |
| Valine, leucine and isoleucine degradation | 1.4 |
| Vitamin B9 (folate) metabolism | 6.5 |
| Glycine, serine, alanine and threonine metabolism | 4.3 |
| Bile acid biosynthesis | 3.7 |
| Purine metabolism | 3.1 |
| Pyrimidine metabolism | 2.6 |

FIG. 22E

PREDICTING METABOLIC SIDE EFFECTS OF TRANSPORTED DRUGS

CROSS REFERENCE TO RELATED APPLICATIONS

This application claims priority under 35 U.S.C. § 119 from Provisional Application Ser. No. 62/296,981, filed Feb. 18, 2016, the disclosure of which is incorporated herein by reference.

STATEMENT REGARDING FEDERALLY SPONSORED RESEARCH

This invention was supported by a Grants R01-GM098449, R01-GM010498 and U54-HL07160 from the National Institutes of Health. The U.S. Government has certain rights in the invention.

TECHNICAL FIELD

This invention relates to methods of identifying and tailoring drug therapy, including approaches to identifying metabolic consequences of drug therapy, the design of drugs based on metabolites accumulating in knockout animals and identified as potential drug transporter substrates, and the targeting of drugs and metabolites to tissue compartments based on the aforementioned methods of metabolite identification.

BACKGROUND

Multiple drug transporters are present in various organs of the body including the kidney, the intestinal epithelium, the brain microvessel endothelium, and the liver. Humans are highly variable in their ability to metabolize and excrete drugs. This variability underlies a great deal of morbidity and mortality as standardized doses of medications can produce drug levels that range from sub-therapeutic to toxic. Organic anion and cation transporters (OATs and OCTs, respectively) are a family of transmembrane proteins largely expressed in excretory organs such as kidney and liver are a major component of the human xenobiotic excretion machinery. These proteins interact with many commonly used drugs including antibiotics, anti-hypertensives, and anti-inflammatories among others. As such it is probable that variations in either the coding or regulatory sequences of OAT and OCT genes contribute significantly to differences in drug-handling capability.

SUMMARY

Genome-scale metabolic reconstruction of transcriptomic data derived from a comparison of wild-type and organic anion transporters together with virtual screening using pharmacophore hypotheses created from known transporter-interacting drugs, provides a number of metabolites potentially affected by deletion of a transporter. These metabolites can and have been validated in wet-lab assays of, for example, the transporter "OAT1". Re-evaluation of the transport and knockout metabolomics data generated a largely experimentally validated OAT1-centered metabolic network that included several key metabolic pathways. Since many of the network metabolites have been implicated as "uremic toxins in chronic-kidney disease (CKD)," a CKD-associated metabolic network was constructed. This overlapped significantly with the OAT1-centered network, suggesting the importance of OAT1 activity in modulating CKD-induced metabolic changes. This novel combined systems biology/computational chemistry approach should be applicable to other SLC and ABC drug transporters to analyze how they may regulate normal and disease metabolism individually and as a group.

The disclosure describes how to predict, based on a drug or other small molecule structure (e.g., pharmacophores), the likely impact on transporter-mediated metabolism. Competition of drugs with metabolites at the level of transporters involved in absorption, distribution, and elimination of drugs and metabolites can lead to major metabolic side effects over the long term. The disclosure can predict many of these ahead of time. This is useful for companies repurposing drugs or prioritizing leads, and possibly, useful clinically to predict metabolic complications in patients on multiple drugs and thus help with choosing the proper drugs in the hospital and clinic. The disclosure uses a combination of metabolic reconstruction (systems biology) methods with computational (pharmaceutical) chemistry, as well as wet lab validation.

The disclosure provides a method for determining a drug therapy or efficacy, drug transporter-associated metabolic disease or disorder, or metabolic side effect in a subject, comprising detecting an amount of each of a plurality of metabolites in a biological sample obtained from the subject, identifying a single or plurality of drug transporter-associated metabolomics pathways; comparing the plurality of metabolites to the single or plurality of drug transporter-associated metabolomic pathways to identifying metabolites associated with a drug transport-associated metabolomic pathways; determining a pharmacophore associated with a plurality of drugs and/or metabolites transported by a drug-transport protein; and determining, based on overlapping metabolites between the drug transport-associated pathways, the metabolites in a biological sample and the pharmacophore the effect a drug will have on metabolism in a subject. In one embodiment, the method further comprises determining a difference between a control and subject's metabolites, wherein a difference is indicative of a drug transport-associated metabolic disease or disorder associated with a pharmacophore. In another embodiment, the method further comprises identifying a drug therapy for the subject based upon a pharmacophore constructed from drugs and/or metabolites that interact with a drug transporter protein. In yet another embodiment, the drug transport-associated metabolomics pathways are identified by analyzing a wild-type metabolic profile and a selected drug-transporter knockout metabolic profile and/or the metabolomics profile of a subject with altered expression and/or function of a drug transporter. In yet another embodiment, the disclosure provides a metabolite or set of metabolites is monitored in a drug therapy for a modulation of a drug transporter metabolic profile to determine an efficacy of the drug and/or the presence of metabolic side effects.

The disclosure also provides a method of treating a subject comprising determining a drug therapy, determining a metabolic profile associated with a pharmacophore of the drug therapy and a drug transporter and administering the drug.

The disclosure also provides a method comprising: (a) obtaining a metabolomic drug transport profile; (b) obtaining a sample from a subject; (c) identifying metabolites in the sample; (d) comparing the metabolites to the metabolomic drug transport profile to identify a patient drug-transport metabolomic profile; (e) provide a drug therapy based upon the patient drug-transport metabolomic profile. In one embodiment, the method further comprises obtaining one or more pharmacophore profiles associated with one or more drug-transport proteins. In a further embodiment, the one or more pharmacophore profiles are matched to the patient drug-transport metabolomic profile to identify a drug therapy.

The disclosure also provides a method of generating a metabolite profile for a drug (cation or anion) transport protein comprising: (a) obtaining a metabolite profile for a normal control cell or organism; (b) knocking-out expression of a drug transport protein in a cell or organism to obtain a knockout organism; (c) obtaining a metabolite profile from the knocked-out cell or organism; (d) comparing the metabolite profile between the normal control cell or organism and the knockout cell or organism; and (e) identifying differences in the profiles, wherein the difference comprises the metabolite or metabolomics profile associated with the drug transport protein. In one embodiment, the normal control and knockout organism comprise a mouse or rat species. In a further embodiment, the metabolites in the metabolite or metabolomics profile to identify one or more common pharmacophores of the metabolites, wherein the one or more common pharmacophores are a pharmacophore profile for the drug transport protein. In yet a further embodiment, the pharmacophore profile is compared to pharmacophore profiles for known drugs to identify drugs that are transported or affect the drug transport protein.

The disclosure also provides a method of identifying a subject with a disease or disorder in a drug transport protein comprising, obtaining a metabolite profile from the subject; comparing the metabolite profile from the subject to a metabolite profile for a drug transport protein identified by the method above, wherein the same or substantially the same profile is indicative of a disease or disorder associated with the drug transport protein.

The disclosure also provides a method of identifying a drug therapy or efficacy for a subject, comprising the method above, wherein a drug therapy or profile is predicated upon the pharmacophore profile associated with the metabolite profile of the drug transport protein.

The disclosure provides a metabolic network which is the result of metabolic network reconstruction of in vitro and in vivo knockout data. This network can be used to overlap with a disease network to identify therapy and disease progression and is key to the invention. The network includes data and research results from transcriptomics, metabolomics and in vitro transport assays to obtain a drug-transporter-dependent metabolic network. The disclosure provides a unique combinations of metabolites predicted by multiscale "omics" data derived from knockout animals and combined with wet-bench lab transport data in cells and tissues to provide a unique reconstruction of drug transporter metabolism which can be overlapped with disease metabolite profiling to predict the metabolic side effects of transported drugs. The one or a plurality of networks can be used. For example, a drug transporter-dependent metabolic network can generated for drug transporters (which, are multispecific). This enables the creating of a set of overlapping networks of metabolites that would be perturbed by one or more drugs (e.g., acting on OAT1/SLC22A6 and ABCC4 in drug therapy. The methods allow prediction of the metabolic alterations that result from adding or administering a drug to a subject. Furthermore, the networks provide a predictive power for drug therapy in subjects that have a preexisting drug transport dysfunction.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A-B shows the results of GEM analysis based on transcriptomics of the knockout animals are consistent with in vivo metabolomics. (A) The number of metabolic reactions and metabolites predicted to be altered due to Oat1 knockout based on GEM analysis. (B) Comparison of metabolomics data from Oat1 knockout mouse (plasma, urine) with computational predictions of GEM transcriptomic-based metabolic network. Column 1: List of metabolites identified by targeted and untargeted metabolomics analysis and represented in iMM1415 (a GEM model). Column 2: Metabolites that are altered either in plasma or urine or both by metabolomics. Column 3: Predictions of changes in fluxspans made by GEM based on the transcriptomic data from wildtype and Oat1 knockout mice (-- is either no change predicted or no prediction possible).

FIG. 4A-B shows the wet lab validation of predicted metabolites and the identification of novel OAT1 metabolites. (A) The $IC_{50}$ curves for the metabolites characterized in the in vitro uptake inhibition assay using CHO stably expressing Oat1. The assay was done by testing for inhibition of uptake of 10 μM 6CF, a fluorescent tracer that is also an OAT1 substrate. (B) The table summarizes the calculated Ki and metabolic pathways the characterized metabolites were involved in.

FIG. 5A-D shows the OAT1-centered metabolic network contains several biochemical pathways essential for cellular metabolism. (A) The network consisted of metabolites known to or predicted to, interact with OAT1; these metabolites were classified according to the level of confidence with which they interacted with OAT1. In the order of level of confidence, the categories were: 1), "wet-lab supported", 2), "predicted to interact with high confidence", 3), "predicted to be affected indirectly", and 4), "plus-one. The "wet-lab support" metabolites were supported by either in vitro or in vivo data. The metabolites "predicted to interact with high confidence" were ones predicted by GEM and passed the pharmacophore filter criteria. The metabolites "predicted to be affected indirectly" were ones that were predicted by GEM only but did not pass the pharmacophore filter criteria. The "plus-one" metabolites were predicted by Metscape as the first neighbors of the aforementioned three groups and did not fit any of the other categories described above. The level of confidence of metabolites interacting with the transporter is reflected by the size and color of nodes; the larger and darker the metabolites are, the higher the confidence of interacting with OAT1. In the network, the well-represented metabolic pathways are shown. (B) The number of metabolites falls into the four confidence categories. (C) The global network parameters of the OAT1-centered metabolic network. (D) The total number of metabolites, the number of wet-lab supported metabolites, and the validation percentage for well-represented pathways are listed in FIG. 5D. Most represented metabolic pathways are ranked according to the validation percentage. Tyrosine, TCA cycle, and tryptophan metabolism are the most well-validated pathways represented in the network, and they contain several metabolites known as classical OAT1 substrates.

FIG. 6A-D shows the degree distribution and the node degree map of OAT1-centered metabolic network. (A) The degree distribution for the network was fitted with the power law equation, $y=ax^b$, using the least-squared method. The measured correlation coefficient a is equal to 217, and the measured exponent b is equal to $-2.151$, demonstrating that the network had degree distribution that followed a power law and was thus found to be scale-free (B) The map shows the value of degree for individual nodes of the main component of the network (and the higher the value of the parameter, the bigger the node). (C) The values of degree for the highlighted metabolites are listed along with the average values of the highlighted metabolites and of all metabolites in the network. (D) the top well represented metabolic pathways.

FIG. 7A-B shows (A) a mapping of metabolites and (B) a listing of certain metabolites.

FIG. 8A-B shows the overlap of the OAT1-centered metabolic network and the chronic kidney disease (CKD)-associated metabolic network. The CKD-associated metabolic network is built based on the metabolites known to be biomarkers for chronic kidney disease (Zhao, 2013). (A) The overlapped, combined model is shown. Overlapping metabolites (113) are marked red, and they represented 44.9% of metabolites in OAT1-centered metabolic network; metabolites found only in the CKD metabolic network are marked blue; and metabolites found only in the OAT1-centered metabolic network are marked green. Among the overlapping ones were metabolites that are both listed as potential uremic toxins and known to directly interact with OAT1 (Deguchi et al., 2004; Wikoff et al., 2011); these included metabolites such as xanthurenate, xanthine, L-citrulline, and hippurate. (B) The number of metabolites for the three metabolite groups is shown along with some examples.

FIG. 9 shows examples of transporters.

FIG. 10A-B shows reconstruction of metabolic networks from large-scale 'omics' data implicates drug transporters in metabolic pathways. (A) One type of computational approach based on 'omics' data for connecting transporters and metabolic pathways is schematically represented. In this strategy, transcriptomic data derived from transporter knockout mice are analysed using genome-scale metabolic reconstruction tools. This approach can be used to support a potential linkage between a specific transporter and certain metabolic pathways that can be further validated by in vitro and other assays. Metabolomics data from knockout mice are also very valuable for supporting predictions. An approach related to this was used to link SLC22A6 (OAT1)-mediated transport to several metabolic pathways. (B) The type of combined computational-wet-lab approach schematized in part (A) once performed for multiple ATP binding cassette (ABC) and solute carrier (SLC) drug transporters, can enable novel interpretations of the role of drug transporters in whole-body physiology, as well as in intracellular metabolism in specific tissues.

FIG. 22A-E shows measures of the global and node network parameters of the OAT1-centered metabolic network, another Cytoscape plugin, NetworkAnalyzer, was used to study the topology of the metabolic network (A). The whole network consisted of 32 connected "components" (253 nodes), including one main component (170 nodes), in which the majority of metabolites were interconnected, and 31 other small self-connected components. Degree distribution, P(k), was measured, which calculates the probability of a selected node n having exactly k degrees (degree of a node is equal to the number of links it has to other nodes). The OAT1-centered metabolic network was found to follow the power law distribution (B) and had Y value of 2.151; thus, the network, like most biological networks, was not random, but appeared scale-free [i.e., most nodes have only a limited number of links, and a few nodes have a very large number of links (these highly connected nodes are also called "hubs")]. Metabolites with high degree were found, including pyruvate, L-glutamine, L-glycine, L-glutamate, and L-serine (C, D). Pyruvate is not only known to interact with OAT1 in vitro4, but it also serves as the precursor for the TCA cycle, which is the energy pathway classically linked with OAT1 function. In addition, the amino acids with high degrees are also important precursors for several metabolic pathways, and their importance in metabolism, as well as in the OAT1-centered network supports, again, the significance of OAT1 in cellular metabolism. Metabolic pathways with an average degree greater than 3.5, included vitamin B9 (folate) metabolism; urea cycle and metabolism of arginine, proline, glutamate, aspartate and asparagine; glycine, serine, alanine and threonine metabolism; and TCA cycle (E).

DETAILED DESCRIPTION

Figure 1A:
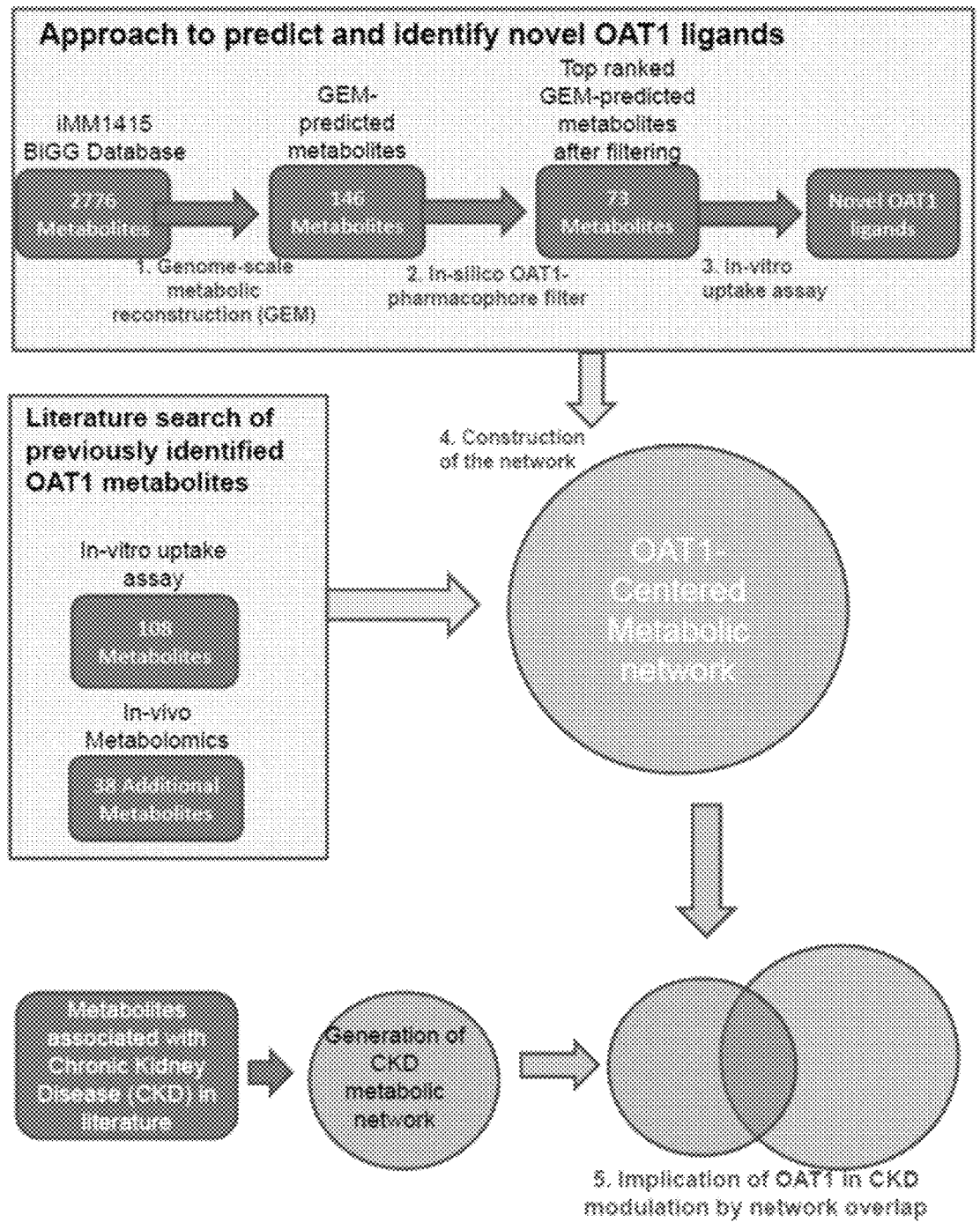
FIG. 1A-C shows (A) a flowchart of methods, which consist of 5 stages: 1) systems biology analysis and mathematical simulation of metabolic reconstruction, 2) computational chemistry analysis and generation of pharmacophore hypotheses and the application of pharmacophore filtering, 3) wet-lab validation and identification of new OAT1 metabolites, 4) construction of a substantially validated OAT1-centered metabolic network, and 5) evaluation of the role of the OAT1-centered metabolic network in disordered metabolism of chronic kidney disease (uremia). (B) An overall strategy employed in an embodiment of the disclosure. As described below, the approach is comprised of 5 stages: 1) systems biology analysis of transcriptomic data for the prediction of metabolites altered by the absence of a chemical transport protein (e.g., OAT1); 2) validation of predictions using metabolomics and kinetic data; 3) computational chemistry analysis, generation of pharmacophore hypotheses, and the application of pharmacophore filtering; 4) wet-lab validation and identification of new chemical transport metabolites/signaling molecules construction of a substantially validated transport-centered metabolic network. (C) Shows a flowchart illustrating the steps employed for the integration of transcriptomic data into the GEM iMM1415 and its analysis leading to the prediction of OAT1-interacting metabolites.

As used herein and in the appended claims, the singular forms "a," "an," and "the" include plural referents unless the context clearly dictates otherwise. Thus, for example, reference to "a cell" includes a plurality of such cells and reference to "the agent" includes reference to one or more agents and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which may be used in connection with the description herein. However, with respect to any similar or identical terms found in the incorporated publications and those expressly defined in this application, then the terms' definition as expressly put forth in this application shall control in all respects.

Despite their well-established roles in the absorption, distribution, and elimination of xenobiotics, there is growing evidence for the transport of metabolites, nutrients, signaling molecules, antioxidants, and other molecules of physiological importance at the organismal and cellular levels by members of the SLC (solute carrier) and ABC (ATP-binding cassette) "drug" transporter families. Owing to their role in regulating the movement of endogenous metabolites across barrier epithelia and between body fluid compartments, it is becoming clear that these transporters play important roles in cellular, organ, and whole body metabolism. In order to address this question, a combined systems biology and computational chemistry approach is described herein. The combination of metabolic reconstruction (systems biology) methods with computational (pharmaceutical) chemistry, as well as wet lab validation was undertaken for all drug transporters of the SLC and ABC family. This information provides a tremendous impact on the understanding of many metabolic diseases (diabetes, gout, kidney disease, liver disease, etc.). Furthermore, since common drugs (or their metabolites) are distributed or eliminated through these transporters, it will help clarify drug-induced metabolic changes.

In vivo drug transport is accomplished by two transporter superfamilies: the solute carrier (SLC) transporters and the ATP-binding cassette (ABC) transporters. Because they have a crucial role in absorption, distribution, metabolism and elimination (ADME), these drug transporters are of considerable pharmacological significance (Table 1); indeed, owing to recent regulatory interest, the focus on these transporters has intensified.

TABLE 1

| Drug | Transporter name* | | | |
|---|---|---|---|---|
| (type of drug) | ABC | SLC22 | SLCO | SLC47 |
| Methotrexate (anticancer, antirheumatic) | ABCC1 ABCC2 ABCC3 ABCC4 ABCC5 ABCG2 | SLC22A6 SLC22A8 SLC22A11 | SLCO1A2 SLCO1B3 | — |
| Acyclovir (antiviral) | — | SLC22A1 SLC22A6 SLC22A7 SLC22A8 | — | SLC47A1 SLC47A2 |
| Adefovir (antiviral) | ABCC4 | SLC22A6 | — | — |

TABLE 1-continued

| Drug | Transporter name* | | | |
|---|---|---|---|---|
| (type of drug) | ABC | SLC22 | SLCO | SLC47 |
| Pravastatin (statin) | ABCB11 | SLC22A8 SLC22A11 | SLCO1B1 SLCO2B1 | — |
| Rosuvastatin (statin) | ABCG2 | SLC22A8 | SLCO1A2 SLCO1B1 SLCO1B3 SLCO2B1 | — |
| Cimetidine (histamine H$_2$ receptor antagonist) | — | SLC22A2 SLC22A8 | — | SLC47A1 SLC47A2 |
| Metformin (antidiabetic) | — | SLC22A1 SLC22A2 SLC22A3 | — | SLC47A1 SLC47A2 |

The common names of the transporters in the table are shown in brackets in the following list: ABCC1 (MRP1); ABCC2 (MRP2); ABCC3 (MRP3); ABCC4 (MRP4); ABCC5 (MRP5); ABCB11 (BSEP); ABCC2 (BCRP); SLC22A1 (OCT1); SLC22A2 (OCT2); SLC22A3 (OCT3); SLC22A6 (OAT1); SLC22A8 (OAT3); SLC22A11 (OAT4); SLCO1A2 (OATP1A2); SLCO1B1 (OATP1B1); SLCO1B3 (OATP1B3); SLCO2B1 (OATP2B1); SLC47A1 (MATE1); SLC47A2 (MATE2).

Organic anion and cation transporters, slc22 family members (OATs, OCTs, OCTNs, and ORCTLs) are transmembrane proteins essential to renal excretion and are encoded by a group of related genes. Multiple OATs and OCTs have been identified in the last few years. Examples of these organic anion transporters are provided in Table 2:

TABLE 2

| Organisms | OAT (aliases) | GenBank Accession |
|---|---|---|
| Murine | OAT 1 (NKT slc22a6) | MMU52842 and NM008766 |
| Murine | OAT 2 (NLT slc22a7) | AB069965 |
| Murine | OAT 3 (Root slc22a8) | NM_031194 and AB079895 |
| Human | OAT 1 | AF097490 |
| Human | OAT 2 | AF210455 |
| Human | OAT 3 | AF097491 |
| Human | OAT 4 | AB026116 |
| Human | OAT 5 | BK001421 |
| Murine | OAT 6 | AF536195.1 |

The above identified GenBank references are incorporated herein by reference in the entirety.

Additionally, UST1, UST3, and OAT5, have sequence homology to transport organic anions as well. Examples of organic cation transporters include OCT1 (slc22a1), OCT2 (slc22a2), and OCT3 (slc22a3), while OCTN1 (slc22a4), OCTN2 (slc22a5; UST2), OCTN3 (slc22a9), and CT2 transports carnitine as well as cations.

ABC drug transporters utilize ATP hydrolysis and function as efflux transporters. In contrast SLC transporters do not rely directly on ATP hydrolysis. Various isoforms of SLC and ABC drug transporters are highly expressed in epithelial cells (on apical and basolateral surfaces) that separate nearly all body fluid compartments (including those containing urine, cerebrospinal fluid or bile), as well as in brain endothelial and other cells, such as circulating cells in the blood.

The drug transporters that have so far received the greatest attention are two ABC transporters (namely ABCB1 (also known as P-glycoprotein (PGP) or MDR1) and ABCG2 (also known as BCRP)) and five SLC transporters (namely SLC22A6 (also known as OAT1 or NKT), SLC22A8 (also known as OAT3 or ROCT), SLC22A2 (also known as OCT2), SLCO1B1 (also known as OATP1B1) and SLCO1B3 (also known as OATP1B3)).

SLC drug transporters do not rely directly on ATP hydrolysis and are largely, but not exclusively, uptake transporters; that is, they are generally involved in the uptake of small molecules into cells. These SLC (Organic Anion Transporters (OATs)) mediate the uptake of structurally diverse compounds: endogenous (steroids, odorants, cyclic nucleotides, neurotransmitters) and exogenous (NSAIDs, toxins, antibiotics) organic wastes (Eraly et al., 2004; Kaler et al., 2006). Importantly, the antiviral nucleoside and nucleobase analogues (Burckhardt and Burckhardt, 2003; Sweet, 2005), antiretrovirals, have recently been implicated as OAT substrates. To combat HIV, Herpes or other retroviruses, antivirals are often administered in prolonged combination therapies as either triple or quadruple cocktails, which can lead to unknown drug-drug interactions (Young, 2005). Pharmacokinetic interactions at the OAT level are often exploited for altering drug bioavailability, such as the frequent use of probenecid to prolong drug action (Launay-Vacher et al., 2006). Unfortunately, many documented cases have indicated that long-term exposure to antivirals is associated with nephrotoxicity, acute renal failure, lactic acidosis, hepatic failure, and skeletal myopathy (Anderson et al., 2004; Lewis, 2003). In spite of this, relative Oat affinity data ($K_m$ or $IC_{50}$) on particular antivirals is limited mostly to OAT1 (Burckhardt and Burckhardt, 2003; Cihlar et al., 1999; Wada et al., 2000), with disparate sources indicating that Oat3 might contribute as well (Cha et al., 2001; Takeda et al., 2002; Uwai et al., 2007). Thus, the particular contribution of each Oat to the basolateral uptake of antivirals is unknown, and potential drug-drug interactions can involve a multiplicity of confounding factors: multiple dependent transporters, varying degrees of substrate specificity at the transporter level, as well as non-overlapping tissue and cell localization. Further mOAT6, an olfactory mucosal transporter, has been postulated as a nasal drug-administration route, but few drug compounds have been implicated as ligands (Monte et al., 2004; Schnabolk et al., 2006). In fact, with such extreme advantages and disadvantages to antivirals, it is surprising that there is a lack of precise data for controlling these incongruent pharmacological effects.

Active transport of endogenous metabolites and xenobiotics from blood to urine across the cells of the renal proximal tubule is an important protective mechanism. Accordingly, there are excretory transport systems in the kidney comprising groups of organic anion transporters (OATs) and organic cation transporters (OCTs), which are subfamilies within the amphiphilic solute transporter branch (SLC22A) of the major facilitator superfamily. In the adult, these transporters are also expressed in other barrier epithelia such as the intestine, placenta, retinal pigment epithelium, and the choroid plexus (CP). Their expression in the CP (located in the ventricles of the brain), coupled with evidence that neurotransmitters (e.g., choline) and neurotransmitter metabolites (e.g., 5-hydroxyindoleacetic acid (from serotonin) and homovanillic acid (from dopamine)) are substrates for the OATs and OCTs, suggests that these transporters actively regulate the composition of brain extracellular fluid. This regulation of the extracellular fluid is accomplished by controlling the flux of xenobiotics and central nervous system by-products from cerebrospinal fluid (CSF) to blood. Transient OAT expression in unexpected sites (e.g., spinal cord, bone, and skin) during development provide an indication that these transporters play a role in the formation or preservation of extra-renal tissues, as well.

Six members of the organic anion transporter family have been characterized: OAT1, OAT2, OAT3, OAT4, OAT5 and OAT 6. OAT1, originally described as novel kidney transporter, NKT, (GenBank accession no. MMU52842 (murine), incorporated herein by reference), has been localized to the basolateral membrane of renal proximal tubules and to the apical membrane of CP through direct observation of an OAT1/green fluorescent protein fusion construct and by immunohistochemistry on adult rat kidney sections. Uptake by OAT1 is trans-stimulated by glutarate, demonstrating that it functions as an organic anion/dicarboxylate exchanger, consistent with its localization in the basolateral membrane of proximal tubule cells. Initial characterization studies of OAT2 (originally described as novel liver transporter), OAT3, and OAT4 indicated that, unlike Oat1, uptake mediated by these transporters is not subject to trans-stimulation, indicating that they function as facilitative transporters rather than exchangers. Mechanistically this would suggest that these transporters are located in the apical membrane in the proximal tubule; however, human OAT3 has recently been localized to the basolateral membrane by immunocytochemistry.

OAT3 (Slc22a8) was originally identified as a gene of unknown specificity that had sequence homology to the transporter genes OAT1 and OAT2. It was subsequently demonstrated that its expression is absent in the juvenile cystic kidney (jck) mouse model and markedly reduced in the kidneys of mice homozygous for the osteosclerosis (oc) mutation. It was, therefore, designated as "reduced in osteosclerosis transporter," or Roct. However, it is now known that Roct shares a 92 and 64% identity at the amino acid level with the recently cloned rat and human OAT3 genes, respectively, and is the murine OAT3 ortholog.

Organic anion transport is known, on the basis of physiological studies, to be regulated by steroids, particularly androgens, as well as by the substrates themselves. Investigations to date have revealed a marked sexual dimorphism in OAT expression, with OAT2 and OAT3 messenger RNA levels negatively and positively regulated, respectively, by testosterone. The potential implications of these findings for gender differences in drug-handling in humans are clear. Post-translationally, OATs have been found to be regulated by phosphorylation: epidermal growth factor, acting through mitogen-activated protein kinases induces OAT activity, and protein kinase C.

Endogenous OAT substrates, which include cyclic nucleotides, prostaglandins, folate, and dicarboxylates, suggest the potential functioning of OATs in various cellular and physiological processes. In addition, certain unexpected observations on the ontogeny of the OATs hint at a potential role in development (possibly due to morphogenetic activity of the above substrates). For example, OATs 1-3 manifest transient embryonic expression in a variety of disparate tissues, including brain, spinal cord, dura matter, intestine, lung, skin, and bone, in addition to liver and kidney. Study of the evolution of OATs through identification of orthologs in phylogenetically distant (and simpler) organisms can provide clues to additional functions performed by these genes. A search of the recently completed *Cuenorhabditis elegans* (worm) and *Drosophila melanogaster* (fly) genomes and have found several OAT-like sequences. Because each gene in the entire *C. elegans* genome has been systematically inactivated with RNA interference, null mutations for the putative worm OATs are available for developmental and functional analysis.

In addition, the sequencing of the human genome has uncovered a remarkable feature of the chromosomal organization of OAT genes. Six of the eight known OATs are found in three tightly linked pairs (i.e., as adjoining neighbors without other genes interposed between them); specifically, these are OAU and OAT1 and 3, OAT4 and URAT1, and UST3 and OAT5. Inspection of the dendrogram of the OAT family reveals that these physical pairs are also proximal tubule closely related 'phylogenetic pairs'. Furthermore, pair members have similar tissue distributions: OAT1 and 3 are in kidney and to a lesser extent brain; OAT4 and URAT1 are also in kidney, but not in brain, with OAT4 present in placenta as well; and OAT5 and UST3 are in liver. These observations suggest that the pairing of OAT genes might exist to facilitate the coordinated transcription (co-regulation) of pair members, for example, through their utilization of a shared regulatory DNA sequence.

Human OAT1 and 3 and rat OAT1 and 3 were all detected in the basolateral concentrations of the proximal tubule. Expression of OAT 1 and 3 was found throughout S1-S3 (in contrast to earlier studies suggesting that rat OAT1 was restricted to the S2 segment). However, rat OAT3 was additionally found in the cortical and medullary thick ascending loop of Henle, connecting tubules, and cortical and medullary collecting ducts. Human OAT4 and URAT1 resembled human OAT1 and 3 in being exclusive to the proximal tubule, but were localized to the apical rather than basolateral surface.

Therefore, tubular and membrane localization does appear to sort with the chromosomal pairings, with OAT1 and 3 at the basolateral surface of the proximal tubule and OAT4 and URAT1 at its apical surface. Consistent with what is known about the physiology of basolateral and apical organic anion transport, the basolateral pair, OAT1 and OAT3, couple organic anion influx to the sodium-dependent dicarboxylate gradient, while the apical pair, URAT1 (which couples organic anion efflux to uptake of tubular urate) and OAT4, are sodium-independent. Thus the OAT1/OAT3 and OAT4/URAT1 gene pairs appear to operate at the basolateral and apical steps respectively of tubular renal organic anion secretion. It should be noted that the membrane colocalization of pair-members does not imply their functional interdependence, as individual OATS are known to independently mediate organic anion transport.

The availability of molecular clones and coding sequences for the OATs and ABC transporters has enabled the rapid (and continuing) functional characterization of these transporters. Notable among recently identified substrates is urate, the tubular reabsorption of which appears to be due to exchange by the apically located URAT1 for intracellular organic anions. Urate, and therefore URATI, have been proposed to contribute to the relative longevity of humans. However, though not noted as such in the report of its cloning, URAT1 appears to be the human ortholog of the previously identified murine RST. The presence of an ortholog in the comparatively short-lived mouse mitigates the hypothesis that URAT1 makes a major contribution to human longevity. Other recently reported substrates include uremic toxins (including indoxyl sulfate which has been hypothesized to contribute to the progression of renal failure), mercaptopurates, and the heavy metal chelator 2,3-dimercapto-1-propanesulfonate.

Nephrotoxins as substrates for OATS have turned out to be a recurring theme, as exemplified by the transport of ochratoxin A, cephaloridine, tetracycline, mercuric conjugates, nephrotoxic cysteine conjugates, and the antivirals adefovir and cidofovir (the latter are the topic of much current interest because of their potential role in the treatment of smallpox following a bioterror attack). Thus, the proximal tubule might be a primary target for toxicity precisely because potential toxins accumulate within it through the action of the basolateral OATS.

Molecular biology techniques for uncovering the biochemical processes underlying disease have been centered on the genome, which consists of the genes that make up DNA, which is transcribed into RNA and then translated to proteins, which then function in metabolic pathways to generate the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over tens of thousands of genes, hundreds of thousands of RNA transcripts and up to a million proteins in human cells. However, it is estimated that there may be as few as 2,500 small molecules in the human metabolome.

Metabolomics is the study of the small molecules, or metabolites, contained in a cell, tissue or organ (including fluids) and involved in primary and intermediary metabolism. Thus, metabolomics reflects a direct observation of the status of cellular physiology, and may thus be predictive of disease in a given organism. Subtle biochemical changes (including the presence of selected metabolites) can be reflective of a given disease, disorder, condition, or physiological state, or class thereof. The accurate mapping of such changes to known metabolic pathways can permit researchers to build, e.g., a biochemical hypothesis for a disease. Based on this hypothesis, the enzymes and proteins critical to or characteristic of the disease can be uncovered such that disease targets may be identified for treatment with targeted pharmaceutical compounds or other therapy. Thus, in some aspects, metabolomic technologies can offer advantages compared with, or in addition to, other approaches such as genomics, transcript profiling, and/or proteomics. With metabolomics, metabolites, and their role in the metabolism may be readily identified. In this context, the identification of disease targets may be expedited with greater accuracy relative to other known methods.

The following table shows the association of transporters and transporter-associated diseases and disorders.

TABLE 3

| Gene name (alternative name) | Association |
| --- | --- |
| SLC22A2 (OCT2) | Metformin concentration, platinum-based drug toxicity |
| SLC22A4 (OCTN1) | Inflammatory disease |
| SLC22A5 (OCTN2) | Systemic carnitine deficiency, inflammatory disease |
| SLC22A6 (OAT1) | Mercury concentration, diuretic response |
| SLC22A8 (OAT3) | Mercury concentration, diuretic response, antibiotic handling |
| SLC22A12 (URAT1) | Hypouricaemia, hyperuricaemia |
| SLC47A1 (MATE1) | Metformin concentration |
| SLCO1B1 (OATP1B1) | Hyperbilirubinaemia, statin-induced myopathy |
| ABCB1 (MDR1) | Chemotherapy resistance, inflammatory bowel disease |
| ABCC2 (MRP2) | Dubin-Johnson syndrome |
| ABCG2 (BCRP) | Chemotherapy resistance, hyperuricaemia |

The term "metabolic pathway" refers to a series or set of anabolic or catabolic biochemical reactions in a living organism ("metabolic reactions") that convert (transmuting) one chemical species into another.

The term "metabolite" refers to any substance produced by or transmutated in a metabolic reaction. A "metabolite"

is considered to be in or belong to a particular metabolic pathway if it is a precursor, product, and/or intermediate of the pathway and/or if the pathway's precursor or product is readily traceable to the metabolite. Such a metabolite can be an organic compound that is a starting material, an intermediate in, or an end product of the metabolic pathway. Metabolites include molecules that during metabolism are used to construct more complex molecules and/or that are broken down into simpler ones. The term includes end products and intermediate metabolites.

The disclosure uses a combination of metabolic information, coupled with known ligand and chromophore designed and wet-bench experimental data to identify drug therapy and/or drug efficacy. In some embodiments, the presence and/or amount(s)/level(s) of specific metabolite(s) in a given metabolic pathway (e.g. products or intermediates of the pathway), and/or collections of such metabolites, are detected or measured, for example, by mass spectrometry and/or chromatography. In some embodiments, such detected amounts are compared to normal or control amounts. In some embodiments, the detected amounts are used to assess or detect alterations in the metabolic pathway, which in some aspects is informative for diagnosis and/or prediction of disease(s) or condition(s). In a specific embodiment, the metabolomics profile of a specific drug transporter or combination of transporters are identified by comparing 'normal controls' to knockout organisms that have a dysfunction or elimination of a specific drug transporter or combination of transporters. In this way, chemical compounds, including drugs and metabolites of respiration can be identified and associated with a drug transporter "profile".

The term "metabolome" refers to the collection of metabolites present in an organism. The human metabolome encompasses native small molecules (natively biosynthesizeable, non-polymeric compounds) that are participants in general metabolic reactions and that are part of the maintenance, growth and function of a cell or tissue.

The terms "patient" and "subject" encompass both human and non-human organisms, including non-human mammals. The term "subject" includes patients and also includes other persons and organisms, e.g., animals such as livestock. For example, the term encompasses subjects diagnosed or analyzed by the methods of the disclosure or from which biological samples are derived.

A "metabolomic profile" is a profile of pathway activity associated with the small molecule metabolites. In one embodiment, a metabolomics profile comprises the metabolites that are associated with a drug transport protein (e.g., an OAT or OCT protein) (sometimes referred to as drug transport metabolomics profile). The activity of the pathways is an indication of metabolic health. For example, one or more small molecule metabolites can be measured in a specific pathway, the small molecule metabolites can include intermediates as well as the end product. The metabolomics profile identifies the pathway's "activity". If the pathway produced a normal amount of the metabolite, then the pathway is normal, however, if the pathway produces excessive or reduced amounts then the pathway has aberrant activity. Typically a disease state (or risk thereof) is identified by a plurality of aberrant pathways in a metabolomics profile. The pathway can be identified numerically, by color, by code or other symbols as being aberrant or normal. In the human body, a vast number of metabolic pathways are well characterized including substrates, intermediates, products, enzymes, genes and the like. One of skill in the art can readily identify the pathways and their metabolites and interconnectedness with other pathways. For example, Sigma-Aldrich has an on-line, interactive metabolic pathway for numerous species including humans (see, e.g., [http://]www[.]sigmaaldrich.com/technical-documents/articles/biology/interactive-metabolic-pathways-map.html) (note that the foregoing has been modified with brackets to eliminate an active hyperlink). For particular disease states, the disclosure provides certain metabolomics profiles that are useful for diagnosis. In the case to organic anion/cation transporters, for example, a change of metabolomics profiles from a "control" or "normal" profile can be indicative of the subject that may have difficulty clearing a drug or overclearing a drug or otherwise difficulties with drug metabolism which can play a role in a drug's efficacy and/or risk.

A small molecule metabolite profile and metabolomic profile can be obtained for normal control (e.g., a "control small molecule metabolite profile" or "control metabolomic profile") and would include an inventory of small molecules or metabolomic pathways that are active in similar cells, tissue or sample from a population of subjects, tissues or cells that are considered "normal" or "healthy" (e.g., lack any disease or disorder traits or phenotypic characteristics relative to a specific disease or disorder being examined).

The term "small molecules" includes organic and inorganic molecules, such as those present in a biological sample obtained from a patient or subject. Examples of small molecules include sugars, fatty acids, amino acids, nucleotides, intermediates formed during cellular processes, and other small molecules found within a cell. In some embodiments, the small molecules are metabolites.

The term "small molecule metabolite profile" refers to the composition, amounts, and/or identity, of small molecule metabolites present in a biological sample, a cell, tissue, organ, or organism. The small molecule metabolite profile provides information related to the metabolism or metabolic pathways that are active in a cell, tissue or organism. Thus, the small molecule metabolite profile provides data for developing a "metabolomic profile" (also referred to as "metabolic profile") of active or inactive metabolic pathways in a cell, tissue, or subject. The small molecule metabolite profile includes, e.g., the quantity and/or type of small molecules present. A "small molecule metabolite profile," can be obtained using a single measurement technique (e.g., HPLC) or a combination of techniques (e.g., HPLC and mass spectrometry). The type of small molecule to be measured will determine the technique to be used and can be readily determined by one of skill in the art.

Also as used herein, the term "test metabolite" is intended to indicate a substance the concentration of which in a biological sample is to be measured; the test metabolite is a substance that is a by-product of or corresponds to a specific end product or intermediate of metabolism.

"Transgenic animal" refers to an animal to which exogenous DNA has been introduced while the animal is still in its embryonic stage. In most cases, the transgenic approach aims at specific modifications of the genome, e.g., by introducing whole transcriptional units into the genome, or by up- or down-regulating pre-existing cellular genes. The targeted character of certain of these procedures sets transgenic technologies apart from experimental methods in which random mutations are conferred to the germline, such as administration of chemical mutagens or treatment with ionizing solution.

The term "knockout mammal" and the like, refers to a transgenic mammal wherein a given gene has been suppressed by recombination with a targeting vector. It is to be emphasized that the term is intended to include all progeny generations. Thus, the founder animal and all F1, F2, F3, and so on, progeny thereof are included.

"Knock-in" refers to the fusion of a portion of a wild-type gene to the cDNA of a heterologous gene "Knock-out" refers to partial or complete suppression of the expression of a protein encoded by an endogenous DNA sequence in a cell. The "knock-out" can be affected by targeted deletion of the whole or part of a gene encoding a protein, in an embryonic stem cell. As a result, the deletion may prevent or reduce the expression of the protein in any cell in the whole animal in which it is normally expressed. For example, an "OAT3 knock-out animal" refers to an animal in which the expression OAT3 has been reduced or suppressed by the introduction of a recombinant nucleic acid molecule that disrupts at least a portion of the genomic DNA sequence encoding OAT3.

The term "chimera," "mosaic," "chimeric mammal" and the like, refers to a transgenic mammal with a knockout in some of its genome-containing cells.

The term "heterozygote," "heterozygotic mammal" and the like, refers to a transgenic mammal with a knockout on one of a chromosome pair in all of its genome-containing cells.

The term "homozygote," "homozygotic mammal" and the like, refers to a transgenic mammal with a knockout on both members of a chromosome pair in all of its genome-containing cells.

A "non-human animal" of the invention includes mammals such as rodents, non-human primates, sheep, dog, cow, chickens, amphibians, reptiles, etc. Typical non-human animals are selected from the rodent family including rat and mouse, most typically mouse, though transgenic amphibians, such as members of the *Xenopus* genus, and transgenic chickens can also provide important tools for understanding and identifying agents which can affect, for example, protein function and disease models.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides.

Typically, the genome of the transgenic non-human mammal comprises one or more deletions in one or more exons of the genes and further comprises a heterologous selectable marker gene.

In principle, knockout animals may have one or both copies of the gene sequence of interest disrupted. In the latter case, in which a homozygous disruption is present, the mutation is termed a "null" mutation. In the case where only one copy of the nucleic acid sequence of interest is disrupted, the knockout animal is termed a "heterozygous knockout animal".

Despite their well-established roles in the absorption, distribution and elimination of xenobiotics (Huang et al., 2010), there is growing evidence for the transport of metabolites, nutrients, signaling molecules, antioxidants and other molecules of physiological importance at the organismal and cellular levels by members of the SLC and ABC "drug" transporter families (Ahn and Nigam, 2009; Nigam, 2015; Wu et al., 2011).

Among these transporters, organic anion transporter 1 (OAT1/SLC22A6), originally dubbed NKT (Lopez-Nieto and Nigam, 1996; Lopez-Nieto et al., 1997), mediates the rate-limiting steps in the renal elimination of organic anionic drugs and a few cationic drugs (Ahn et al., 2009; Burckhardt and Burckhardt, 2011; Nigam et al., 2015; VanWert et al., 2010). The pharmacological and toxicological relevance of OAT1 has been supported by in vivo and ex vivo studies in knockouts (Nagle et al., 2011; Nagle et al., 2013; Torres et al., 2011; Truong et al., 2008; Vallon et al., 2008), which have also provided new information about the potential role of OAT1 in basal physiology. For example, metabolomic studies comparing the plasma and urine of wild-type (WT) and knockout (KO) mice revealed significant changes in the concentrations of a number of endogenous metabolites (Eraly et al., 2006; Wikoff et al., 2011).

Taken together with the fact that OAT1 and other SLC22 transporters have been implicated in the transport of key biochemical pathway intermediates, as well as in metabolic diseases (Ahn et al., 2011; Nigam et al., 2015), this suggests an important, if underappreciated, role for SLC "drug" transporters in metabolic processes. Perhaps because of their key role in pharmacokinetics, these transporters are not generally depicted in biochemical pathways involving the metabolites they transport. Such an omission could have clinical significance, with drugs directly or indirectly affecting pathways normally involved in the movement of key metabolites, pathway intermediates, and signaling molecules, thereby fundamentally affecting cell and organ physiology. If so, this might help explain metabolite-drug interactions and perhaps even aspects of certain drug-induced metabolic syndromes (e.g., those seen with diuretic use or chronic HIV antiviral treatment). It may also be useful for further defining the role of drug transporters in modulating common metabolic diseases, such as diabetes and kidney diseases (Nigam, 2015; Prentice et al., 2014; Sharma et al., 2013).

Figure 1B:
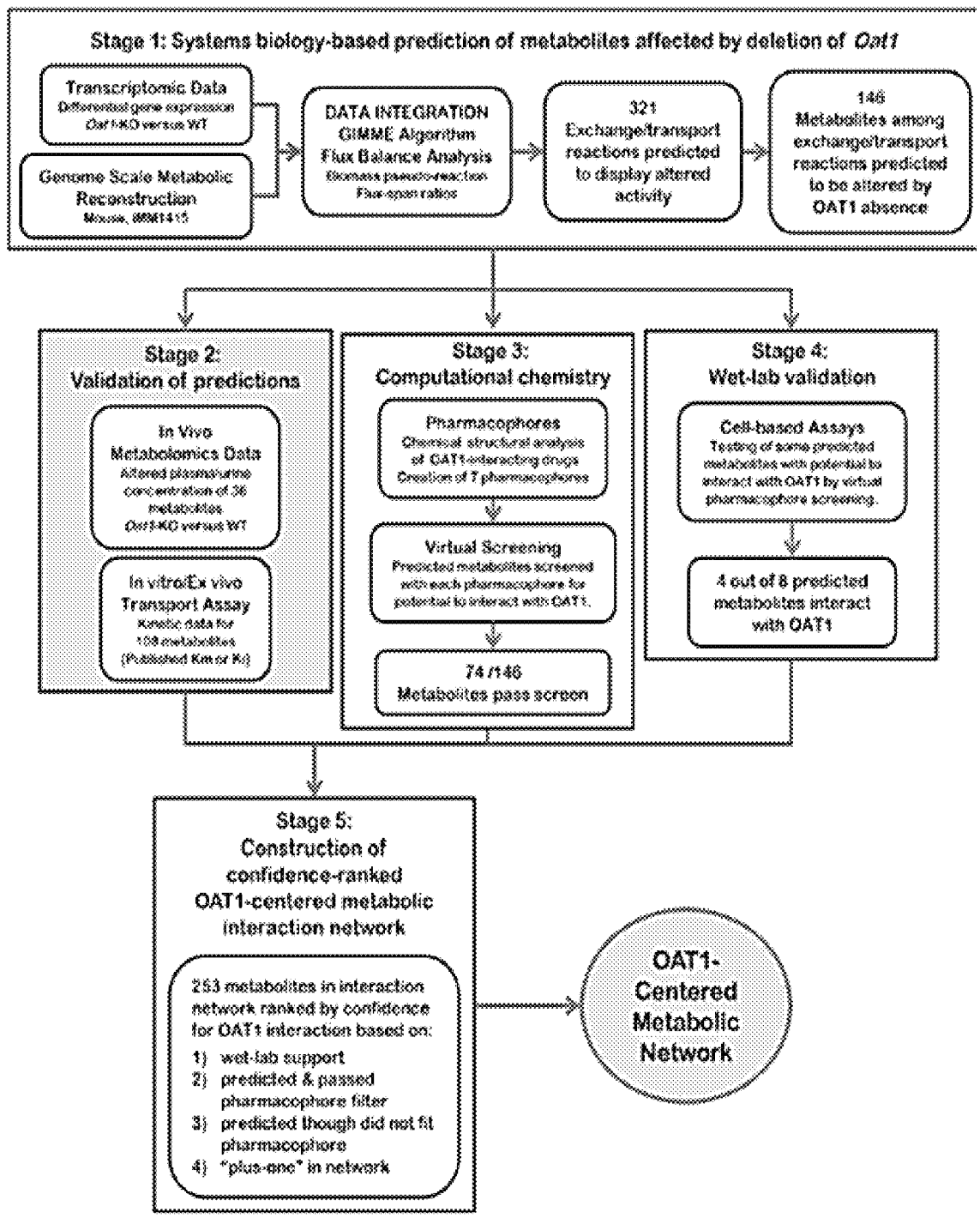

Thus, it is important to begin to build a detailed map of metabolism affected by "drug" transporters such as OAT1. In order to address this the disclosure provides a combined systems biology and computational chemistry approach (FIG. 1A-B). Transcriptomics data derived from wildtype (WT) and OAT1-deficient mouse kidneys was analyzed and used to build a mathematical reconstruction using iMM1415 (Sigurdsson et al., 2010), a mouse genome-scale metabolic reconstruction (GEM) (Duarte et al., 2007), which predicted the involvement of ~150 metabolites represented in several biochemical pathways. Some predictions were then validated with untargeted and targeted metabolomics data obtained from the Oat1 knockout mouse (Eraly et al., 2006; Wikoff et al., 2011). These metabolites were quantitatively assessed for their likelihood to bind OAT1 by virtual screening using pharmacophore models based on drugs known to be handled by this transporter. Novel metabolites predicted to interact with OAT1 were assayed using in vitro transporter assays, and based on these analyses, an "OAT1-centered metabolic network" was constructed to reflect those metabolites with the ability to interact with OAT1. In this OAT1-centered network, about thirty percent of the metabolites are validated by in vitro data and/or in vivo data. This network was further evaluated in the context of metabolic changes occurring in chronic kidney disease (CKD), which can cause dramatic alterations in metabolites, including uremic toxins thought to interact with OAT1 (Wikoff et al., 2011). A strong overlap was observed between the CKD-associated metabolic network and the OAT1-centered metabolic network, raising the possibility that targeting the expression and/or function of OAT1 may be useful for modulating some of the metabolic alterations of CKD. Moreover, the approaches employed can be applied to other SLC and ABC drug transporters to define how they separately and collectively regulate systemic metabolism in health and disease.

The following table shows the result of transporter knockouts on metabolites:

TABLE 4

| Gene name (alternative name) | Metabolites (alternative name) |
|---|---|
| Slc22a6 (Oat1) | 3-Hydroxybutyrate |
| | Benzoate |
| | 2-Hydroxy-3-methylvalerate |
| | 2-Oxoglutarate (α-ketoglutarate) |
| | Indoxyl sulphate |
| | Indole lactic acid |
| | Kynurenine |
| | Pantothenic acid |
| | Urate |
| | Thymidine |
| | Orotic acid |
| | Amino-cresol sulphate |
| Slc22a8 (Oat3) | Pongamoside A |
| | 9-Amino-nonanoic acid |
| | Flavin mononucleotide |
| | Thymidine |
| | Urate |
| Slco1a1 (Oatp1a1) | Trimethylamine |
| | Gulonate |
| | Isethionic acid |
| Slco1a4 (Oatp1a4) | Trimethylamine |
| | Isethionic acid |
| SLCO4C1(OATP4C1)* | Asymmetric dimethylarginine |
| | Guanidinosuccinic acid |
| | Trans-aconitate |
| Abcc3 (Mrp3) | Enterodiol-glucuronide |
| | Secoisolariciresinol-glucuronide |
| | Enterolactone-glucuronide |

The disclosure further provides a pharmacophoric approach for developing a drug therapy or limiting a drug therapy based upon pharmacophore and metabolomics and drug transporters. The pharmacophore can be characterized, for example, via crystallography data and/or chemistry. The structural features of a drug can be expressed as one or more pharmacophore features and/or compiled in a pharmacophore model comprising one or more pharmacophore features.

Pharmacophore generation can be according to software designed for such a task. Candidate molecules (from, for example, one or more chemical libraries) can be selected from those molecules which align to the pharmacophore models. Typically, candidate molecules are docked and scored in silico. Scoring can be according to software designed for such a task. After selection of molecules aligning to one or more pharmacophore models, with optional scoring in silico, the selected molecules can be obtained, for example, by chemical synthesis or from a commercial source. The selected molecules can be measured for binding affinity and/or effect on function of the drug-transporter or on downstream metabolic profiles. Such assessment can be according to a biological assay. The tested molecules can be further selected according to desirable measured parameters. The selected molecules and/or the further selected molecules can optionally be further optimized.

A pharmacophore model can be constructed from structural information of biomolecule/drug components, including definition of atom position. In various embodiments, in silico approaches can be used for de novo structure design with a fragment based approach employing contact statistics, 3D surface models, and docked ligands as templates.

A pharmacophore model or scheme is generally a set of structural features that are related. Typical feature components useful in generating a pharmacophore scheme include, but are not limited to, atomic position; atomic radii; hydrogen bond donor features; hydrogen bond acceptor features; aromatic features; donor features; acceptor features; anion features; cation features; acceptor and anion features; donor and cation features; donor and acceptor features; acid and anion features; hydrophobic features, hydrogen bond directionality, and metal ligands. Such features can be located, for example, at a single atom, centroids of atoms, or at a projected directional position in space.

Exemplary resources for accomplishing such modeling and queries include, but are not limited to MOE (CGG) (providing pharmacophore query and visualization), Glide (Schrodinger) (providing docking and scoring), Accord for Excel (Accelrys) (providing organization of molecular information including chemical structures and formulas), and the ZINC database (UCSF) (providing a library of commercial compounds).

The disclosure thus provides a predictive model of drug therapy and interactions that utilize the pharmacophore-related drug transport of organic transporters to identify/target downstream metabolomics diseases and disorders. For example, using metabolomics data obtained from organic transporter knockouts and metabolomics data to various diseases and disorders one can then create a map of related pathways and thus drug therapies that are associated with the particular drug candidate. Moreover, such drug therapies can be used to predict and modify the efficacy of a drug treatment regimen.

The examples below provide a validated, and disease relevance OAT1-centered metabolic network. This drug transporter is also the focus of regulatory agencies concerned about side effects of drugs due to interaction at the level of the transporter (Nigam, 2015). Indeed, it is becoming increasingly clear that OAT1 and other drug transporters—which are differentially and highly expressed in various epithelial tissues lining body fluid compartments, as well as endothelial and other cells and are also highly conserved through evolution—play key roles in regulating levels of endogenous metabolites (Ahn et al., 2011; Nigam et al., 2015; Wikoff et al., 2011; Wu et al., 2013).

A limited number of endogenous substrates of these "drug" transporters have been identified, which has made it more difficult to identify the metabolic networks in which these transporters might be involved. Furthermore, metabolic reconstruction has been hampered in most cases by relevant 'omics' data and computational methods, but OAT1 is a notable exception. OAT1 is largely responsible for the uptake of anionic substrates from the blood and their elimination into the urine, from the viewpoint of organ physiology, any change in the function of OAT1 (e.g., Oat1 knockout) would concomitantly alter the concentration of metabolites transported by OAT1 not only in the bloodstream, but in the proximal tubule cells of the kidney as well, which could result in alterations in gene expression. Thus, with the availability of transciptomic and metabolomics (untargeted and targeted) data from the Oat1 knockout mice, the disclosure links one of the most important multispecific drug transporters, OAT1, to a number of metabolic pathways; we are thus able to propose an OAT1-centered metabolic network, much of which is validated by in vitro and/or in vivo data. Furthermore, the disclosure provides methods that provides a separate direct interactions with the transporter from potential indirect cascade effects. Metabolites in this network substantially overlap with those known to accumulate in CKD patients (including many putative uremic toxins) as well as in animal models of this complex metabolic disorder.

Thus the disclosure combines multiple systems biology and computational chemistry methods with wet lab data from knockout mice and in vitro assays (FIG. 1). The disclosure uses transcriptomic changes from the Oat1 knockout kidney to develop a quantitative reconstruction with the well-validated systems biology tool iMM1415 (a mouse genome-scale metabolic reconstruction (GEM)) to predict metabolic changes due to the loss of Oat1. In this example, the predictions were in reasonable agreement with the in vivo metabolomics results. Chemical constraints are applied at the molecular and atomic levels to identify those metabolites predicted by GEM that were likely to be directly transported by a transporter (e.g., OAT1); these constraints can then be built into pharmacophore models based on a set of drugs known to directly interact with the transporter (e.g., OAT1) at an affinity of <100 µM. This approach can be used to narrow the list of metabolites likely to interact with the transporter (e.g., OAT1). For example, a set of 8 of these were tested using in vitro assays; half (4) were identified as directly interacting with OAT1, including prostaglandin E1, dihydrofolic acid, palmitoleic acid, and 16-hydroxy-hexadecanoic acid (FIG. 4B). These metabolites can be important in whole-body physiology and cellular metabolism. For example, prostaglandin E1, an endogenous vasodilator, serves to increase peripheral blood flow (Weiss et al., 2002), while dihydrofolic acid is required to synthesize both purines and pyrimidines. Palmitoleic acid, a longchained fatty acid serving as a potential lipokine, is important in the regulation of lipid metabolism (Hodson and Karpe, 2013). Based on these results, the transporter (e.g., OAT1) can be implicated in the modulation of a number of metabolic pathways, including, in the case of OAT2, the urea cycle, TCA cycle, purine and pyrimidine metabolism, tyrosine metabolism, fatty acid, and prostaglandin metabolism.

The multifaceted analyses described here, e.g., for OAT1, enable the construction of a "drug transporter"-centered metabolic network that can be applied to other SLC and ABC drug transporters to generate a more comprehensive picture of the role these transporters play in metabolism. Eventually, this approach can connect cellular metabolism in different organs via molecules transported by multispecific drug transporters (as well as other transport systems such as those involving other types of transporters or channels).

Given the broad substrate specificity of many SLC and ABC transporters, as well as their abundance in tissues like the kidney and liver, it is likely that they play an important role in modulating metabolite levels in complex metabolic diseases such as chronic liver and kidney disease, metabolic syndrome and diabetes (Nigam, 2015; Prentice et al., 2014; Schuetz et al., 2014; Sharma et al., 2013). For example, some metabolites known to be transported by OAT1 are potential classical uremic toxins (e.g., indoxyl sulfate, kynurenate, spermine, and uric acid) which accumulate in CKD (Duranton et al., 2012; Vanholder et al., 2003). The analyses, for instance, indicate the importance of the OAT1-centered network in CKD; half of the metabolites in the OAT1-centered network overlapped with the CKD network. This provides a rationale for potential therapies aimed at ameliorating the uremic syndrome of CKD by enhancing Oat1 expression and/or function.

In addition, the complexity of the OAT1-centered network points to the possibility of unexpected metabolic changes that could be induced by chronic treatment with drugs that compete with key metabolites for elimination; these changes could go well beyond the relatively straightforward concept of transporter-level competition for the ligand binding site. Thus one can separate direct versus indirect interactions of metabolites with transporters (e.g., OAT1); thus, a drug that tightly binds e.g., OAT1, may not only alter metabolites that directly compete for transport but also others in the OAT1-centered network that are not directly transported by OAT1. Since thiazide diuretics and HIV antivirals are transported by OAT1 (Nagle et al., 2011; Nagle et al., 2013; Truong et al., 2008), the OAT1-centered network may help in understanding the drug-induced metabolic syndromes associated with chronic treatment with these drugs (Anderson et al., 2004; Lewis, 2003; Monier and Wilcox, 2004; Sinxadi et al., 2013). Importantly, once drug-transporter metabolic networks are created for other SLC and ABC multispecific transporters, the systems biology approach employed here may be useful for explicitly predicting the metabolic alterations expected for new drugs in healthy or diseased populations with globally-altered metabolism (e.g. CKD, liver disease, metabolic syndrome, diabetes).

A computer system can be used to process and compare data associated with metabolite/metabolomics profiles. For example, a computer may be understood as a logical apparatus that can read instructions from media and/or a network port, which can optionally be connected to server having fixed media. The system, can include a CPU, disk drives, optional input devices such as keyboard and/or mouse and optional monitor. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party.

In some cases, the computer system can be implemented using software modules executing on computer architectures and systems. In other embodiments, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card Software comprising algorithms to performed comparisons of metabolic/metabolomics profiles and/or identifying pharmacophores associated with a group of metabolites can be implemented on a computer system.

The following examples are provided to further demonstrate the invention and do not limit the disclosure or the claims.

EXAMPLES

Example 1

Figure 3A:
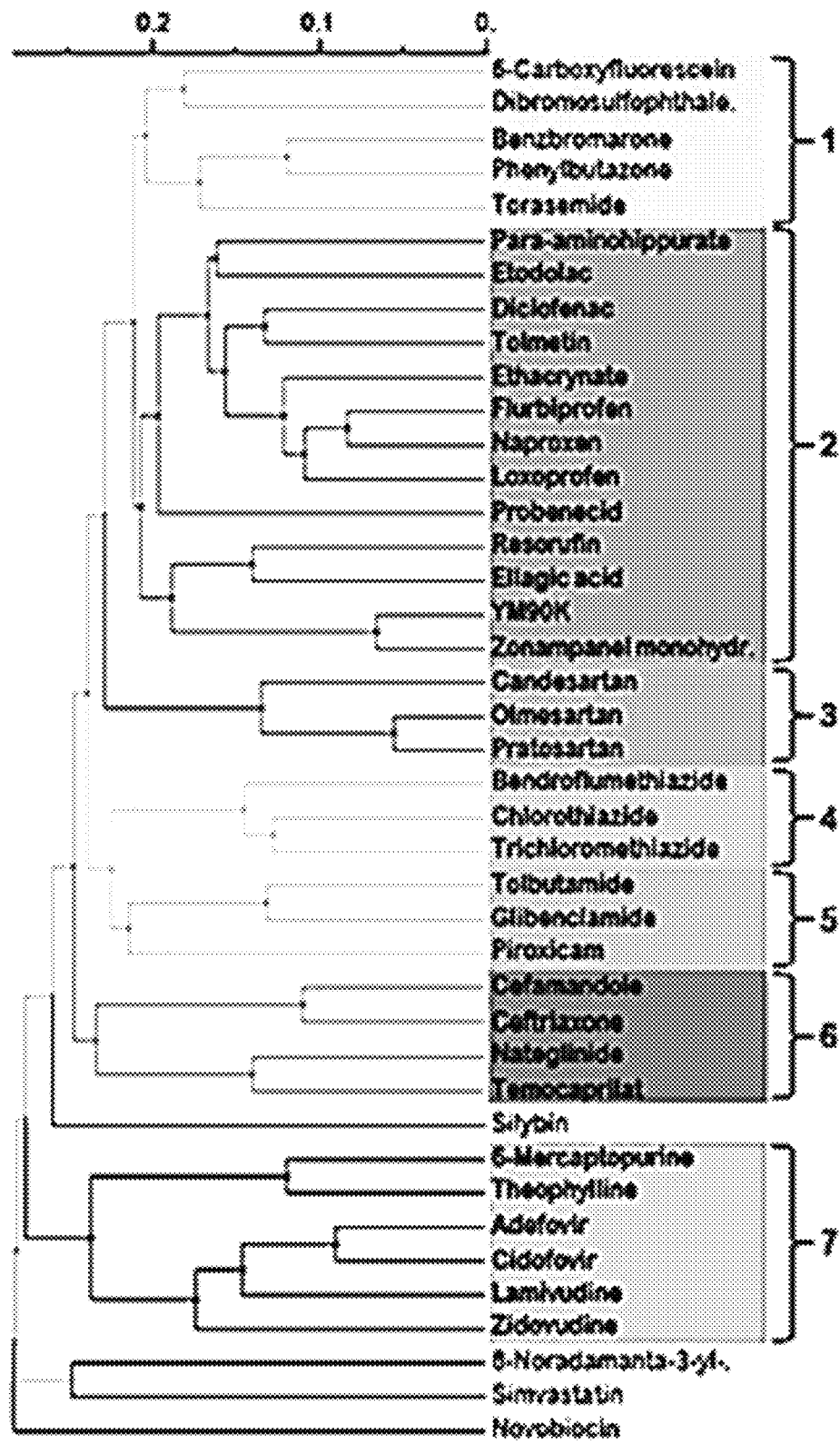
FIG. 3A-C shows the clustering of drugs and the alignment and pharmacophore generation for individual clusters. (A) Clustering of OAT1 drugs based on atomic property field (APF). (B) The alignment of drugs from cluster 1 and the creation of pharmacophore model 1. (C) The seven pharmacophore models generated; blue—hydrogen bond donor; red—hydrogen bond acceptor; white—aromaticity; yellow—hydrophobacity; light red—negative charges; Light blue—positive charges.
Figure 19A:
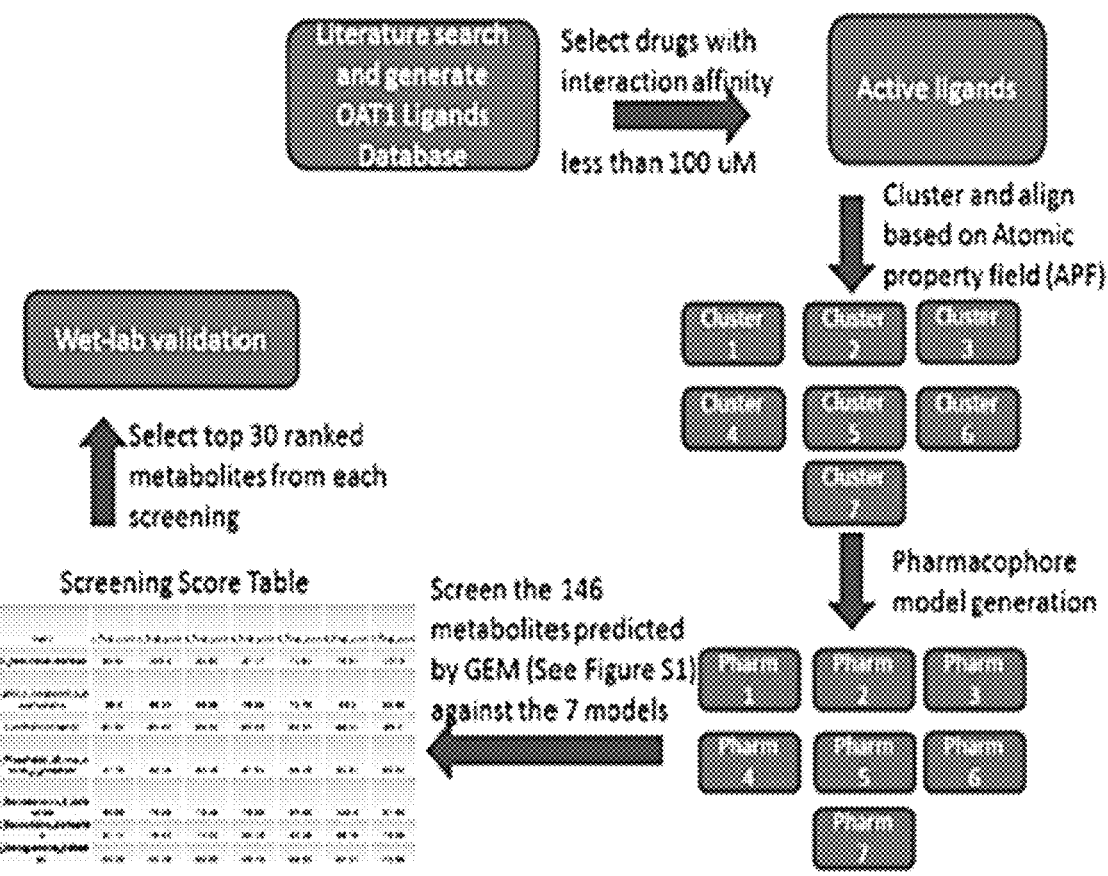
FIG. 19A-B shows Ligand-based pharmacophore creation and virtual screening. (A) A literature search was done to identify high-affinity OAT1 pharmaceuticals, and those having Km or Ki less than 100 μM with OAT1 interaction were selected as active ligands for pharmacophore generation. These active ligands were clustered into 7 groups based on atomic property field (APF), and a single pharmacophore model was generated based on each of the clusters, yielding a total of 7 pharmacophore models (FIG. 21). The metabolites predicted to be affected by the knockout of Oat1 in the genome-scaled metabolic reconstruction (GEM) analysis were screened against the 7 models, and the top 30 metabolites from each screening were compiled as "Top-ranked GEM predicted" (passing the OAT1 pharmacophore filter step) metabolites and some of them were selected for further wet-lab validation. (B) The receiver operating characteristic (ROC) curve generated from the virtual screening of the validating set of drugs using the pharmacophore models. The area under the curve (AUC) was calculated to be 80.58.
Figure 19B:
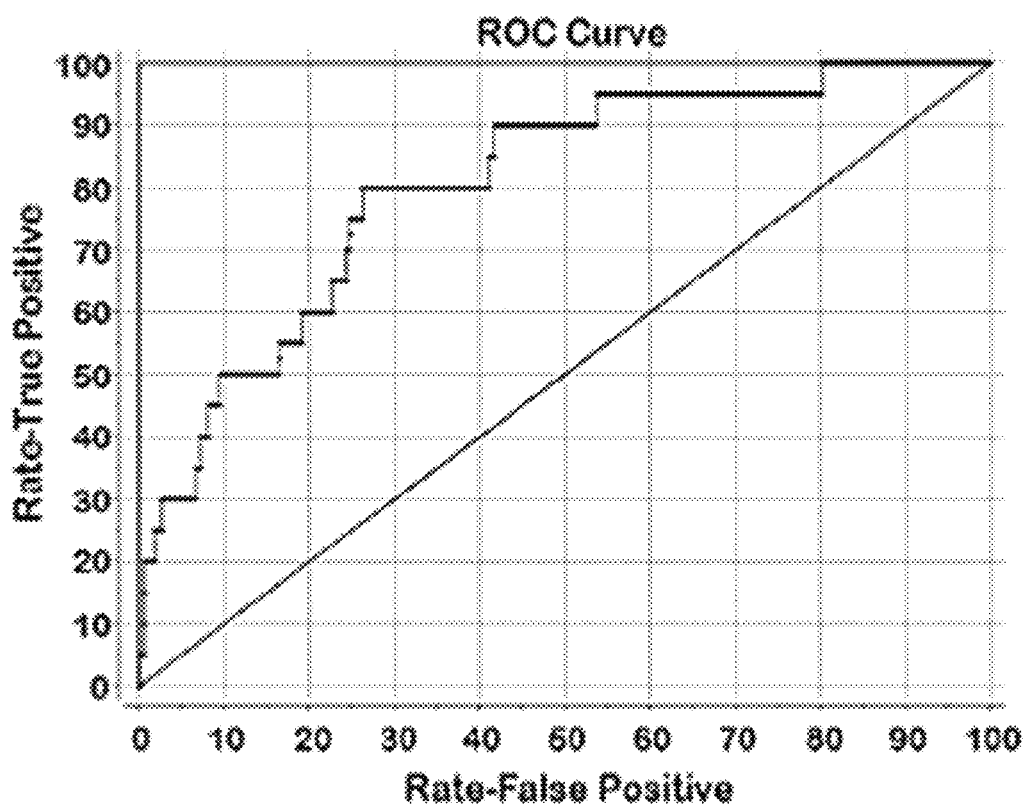
Figure 20:
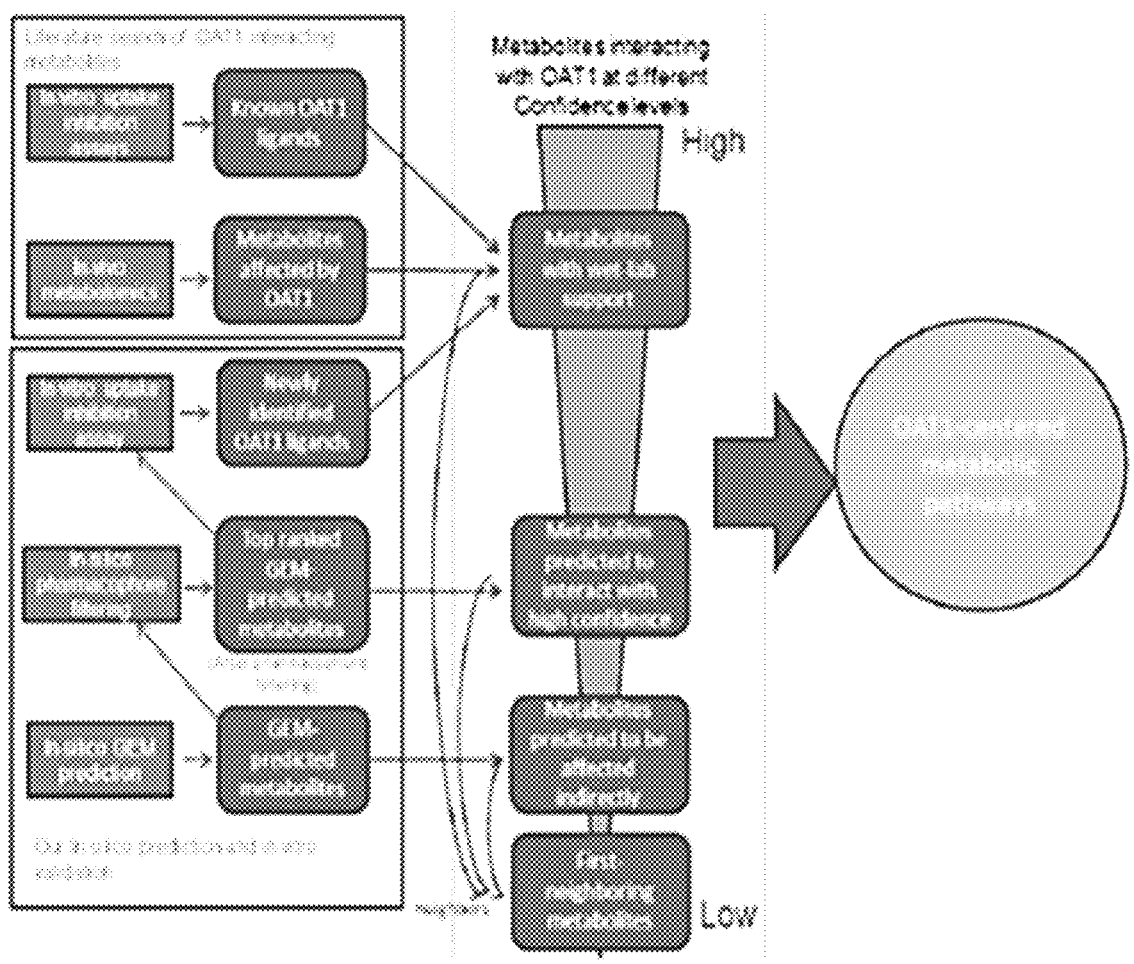
FIG. 20 shows the generation of an OAT1-centered metabolic interaction network using both wet-lab data and in-silico predictions. The OAT1-centered metabolic network was generated based on metabolites known to, or predicted to, interact with OAT1 originating from 5 sources: previous in-vitro uptake assays, previous in-vivo metabolomics, the in-vitro uptake assays done here, the GEM prediction followed by the pharmacophore filtering, and the GEM prediction alone. KEGG IDs for the metabolites were input into the Cytoscape plug-in, MetScape, and an OAT1-centered metabolic interaction network was generated.

The overall approach taken in the study is depicted in schematic flow charts (FIG. 1A-B), which comprises the following stages: 1) systems biology analysis to predict metabolites affected by the deletion of OAT1 (FIG. 1C); 2) validation of models using in vivo and in vitro data (FIG. 1B); 3) computational chemistry analysis (FIG. 3 and FIG. 19); 4) wet-lab validation (FIG. 4); and 5) construction of an OAT1-centered metabolic interaction network (FIG. 5 and FIG. 20).

Materials—

Water-soluble probenecid was purchased from Molecular Probes. The fluorescent tracer (6-carboxyfluorescein), tested metabolites, and signaling molecules (prostaglandin E1, pristanic acid, elaidic acid, trans-vaccenic acid, dihydrofolic acid, palmitoleic acid, β-nicotinamide mononucleotide, and 16-hydroxy-hexadecanoic acid) were purchased from Sigma.

Analysis of Transcriptomic Data with Mouse GEM Network—

The transcriptomic and metabolomics data from previous studies were used for the context specific analysis. The mouse GEM, iMM1415, which contains the biochemical transformations for numerous tissues and cells in mice, was utilized (see FIG. 1C). To create context-specific models, gene expression data from wild type (WT) and Oat1 knockout (KO) mice were analyzed by Microarray Suite version 5.0 to assign present/absent calls. A minimum of 3 sets of microarray data for each condition (WT and KO) was analyzed separately, and for a gene to be considered present, it had to be present in at least 2 of 3 sets of data. In this way, the gene expression data were converted into a "binary" classification (i.e. either absent or present). This binary data without regard to actual expression values was then integrated into the genome-scale metabolic reconstruction model using the GIMME algorithm using the default setting of 90% for the percentage of the objective function needed to be met to generate the model.

GEM reconstructions and the application of constraint based analysis of metabolic networks are widely used in systems biology approaches. The initial planned approach for this study described here was to apply statistical analysis or sampling of the networks with FVA. Unfortunately, the use of strictly constrained FVA models not only resulted in the prediction of a limited number of metabolites with which to work, but they also failed to capture some important interactions known to involve the transporter. Although this is not an uncommon occurrence, it is particularly problematic for this study when one takes into account the fact that our current understanding and the scope of the current metabolic models do not adequately encapsulate the metabolic interactions/alterations resulting from the deletion of SLC drug transporter. In other words, the initial approach was limited by a metabolic model that was not specifically designed to address the questions that were being asked and thus required a modified approach described below.

Sensitivity Filter Through Comparison of the Metabolic Differences Between KO and WT with FVA and Model Validation—

FVA was used to compare functional differences between the WT and KO mice based on maximal achievable reaction flux ranges. A reduced model was created by removing those reactions classified as absent based on gene expression data from the WT and KO conditions. When establishing the lower and upper bound for exchange reactions, uptake constraints for WT and KO models were set to be the same (10 μmol/h) for most metabolites, and to make the model more renal-specific, a few metabolites that were listed for the previously published renal objective function, which was used to analyze blood pressure regulation, were set to be either secreted or absorbed accordingly. In our analysis, a biomass maintenance function, which was defined to represent the metabolic composition necessary for the maintenance of mouse tissues, was used as the constraint to generate the context-specific models using the GIMME algorithm. We also considered the ATP objective function, as well as the so-called "renal objective function". As with the biomass objective function, application of these other objective functions to the data requires some degree of approximation. Although the ATP objective function produced similar results to the biomass objective function, the application of the later produced a broader range of results. Interestingly, despite its name, the application of the renal objective function resulted in a more limited set of metabolites for subsequent analysis. This is likely due to the fact that it was designed for the analysis of the role of the kidney in regulating/modulating blood pressure.

The biomass pseudo-reaction was ultimately selected to ensure that the cells could produce the complement of small molecules requisite for its function and cellular maintenance as well as metabolites/signaling molecules known to be transported by OAT1 have roles in cell maintenance and growth. Flux spans were then calculated as the differences between the maximum and minimum of reaction fluxes and the pairwise ratio between the KO and WT flux spans were calculated (i.e. [(max fluxWT)–(min fluxKO)]/[(max fluxWT)–(min flux WT)]), resulting in a set of flux span ratios for the set of reactions shared between the two models. Flux span ratios with a value of 1 were considered to be unchanged; in this loosely constrained model, any variation from 1 was considered to be affected by the absence of OAT1 and a successful model was expected to generate a list of "GEM-predicted OAT1 metabolites" that could be further evaluated.

Specificity Filter Through Pharmacophore Model Building and Validation Based on Drugs Known to Interact with OAT1—

Computational chemistry analysis was performed with ICM software developed by Molsoft L.L.C (San Diego, Calif.). The software was used to perform clustering, alignment, and pharmacophore building based on the APF of OAT1-interacting drugs or tracers (pharmaceuticals) with known Km (substrate affinity) or Ki (inhibitory affinity) of less than 100 μM were selected. A total of 61 pharmaceuticals were selected; among which two-thirds (41 drugs) were selected for a training set for the model generation, and one-third (20 drugs) were placed in a validating set. The structure-data files (pubchem.ncbi.nlm.nih.gov) for the OAT1-interacting drugs were input into ICM, which superimposed and aligned the drugs based on using the APF superimposition method. This method takes into consideration a number of three-dimensional structural parameters, hydrogen bond donors, hydrogen bond acceptors, SP2 hybridization, lipophilicity, size of large atoms, and positive and negative charges. Based upon these alignments, 7 pharmacophore hypotheses were generated. After the model generation, the validating set (serving as true positives) and all the drugs from the Drugbank database (serving as true negatives) were screened against the pharmacophores. Using these screening results, a ROC curve was generated (FIG. 19).

Screening the List of Metabolites Predicted by the Metabolic Networks with Pharmacophore Models—

The GEM-predicted OAT1 metabolites were compared with each of the 7 pharmacophore models and ranked by how well they fit with the three-dimensional molecular space defined by the drugs known to interact with OAT1. The 30 metabolites that best fit each of the 7 pharmacophores were selected as having potential to directly interact with OAT1. Many metabolites fit more than one pharmacophore model. After eliminating overlaps, 74 metabolites remained, and these were termed "top-ranked GEM-predicted OAT1 metabolites" (passing OAT1 pharmacophore filter).

Uptake Inhibition Assay—

Oat1-transfected CHO cells cultured on 96-well plates were incubated in the presence of 10 μM 6-carboxyfluorescein with or without individual metabolites (with controls treated with the OAT1 inhibitor probenecid). The $IC_{50}$ curves for novel ligands were plotted in Prism Software (GraphPad Inc., San Diego, Calif.), and the IC50 values were converted to Ki (inhibition affinity) using the Cheng-Prusoff equation.

$$K_i = \frac{IC_{50}}{1 + \frac{[S]}{K_m}} \qquad (Eq.\ 1)$$

Construction of an OAT1-Centered Metabolic Interaction Network—

The OAT1-centered metabolic interaction network was generated based on the categorization and ranking of metabolites according to the confidence for their interaction with OAT1. Those metabolites for which kinetic data exists indicating the ability to interact with OAT1 were merged together and labeled as "wet-lab supported" metabolites. Metabolites predicted by the GEM analysis, which also fit the pharmacophore filtering were designated as "metabolites predicted to interact with high confidence." Metabolites that were predicted by the GEM analysis but which did not fit the pharmacophore screen were designated as "metabolites predicted to be affected indirectly." The KEGG IDs for all of these metabolites were input then into Metscape, a Cytoscape plug-in. Metabolites present in Metscape were used as "input metabolites" to build a metabolic network. The construction of the network also introduced many "plus-one" or "first-neighbor" metabolites, and because there is currently no evidence supporting their interactions with OAT1, they were deemed to have the lowest confidence for interacting with OAT1. The network was then trimmed to eliminate uninformative nodes using the following criteria: small molecules (such as water, carbon dioxide, etc.), energy-related molecules (NADH, ATP, etc.), and large peptides not known to interact with OAT1 or related transporters (somatostatin, kinetensin, etc.) were removed; unnecessary "dead-ended" and "inter-connecting" plus-ones were removed to create a more concise network (in other words, dead-ended plus-one nodes, which connected only to one node, were removed, as were inter-connecting plus-ones that did not affect connections between wet-lab validated or predicted nodes). The final network thus consisted of metabolites that fell into four categories, which in the order of level of confidence of their potential to interact with OAT1, the categories were: 1) wet-lab supported; 2) predicted to interact with high confidence; 3) predicted to be affected indirectly; and 4) plus-one after trimming.

Metabolic Pathway Analysis—

Pathway and enrichment analyses were performed using Metaboanalyst 3.0 for pathway analysis and visualization. Lists of the KEGG IDs for the metabolites were input into this online bioinformatics resource to either the Pathway Analysis or Enrichment Analysis functionalities on the MetaboAnalyst 3.0 website. For the pathway analysis, the *Homo sapiens* (human) pathway library was selected and all compounds in the selected pathway were used. The algorithms specified were the hypergeometric test for the over-representation analysis and the relative betweeness centrality for the pathway topology analysis. For enrichment analysis, the pathway-associated metabolite set was selected as the library and all compounds in the metabolite set library were used.

Statistics—

To determine whether the overall in silico approach results in significant enrichment of metabolites known to have direct interaction with OAT1, a hypergeometric-based test was performed to calculate the various p values. The hypergeometric calculation, which is based on certain assumptions, has been used in systems biological analyses for determining the probability of a result occurring just by chance. The hypergeometric test can be used as a measure of over-representation and takes into account the overall population size, the number of successes within this population, the sample size, and the number of successes within the sample population.

A loosely constrained, context-specific analysis of transcriptomic data of a global metabolic model was performed to catch all possible metabolites potentially interacting with OAT1 (either directly or indirectly) followed by pharmacophore-based virtual screening, along with comparison to in vivo/in vitro databases and wet-lab assays to provide the specificity filters to differentiate those metabolites that would directly interact with OAT1 from those likely to indirectly be part of the pathway (but not an OAT1 substrate). Ultimately, this multi-tiered systems level analysis, together with metabolomics (from knock-out and wild type animals) and transport data from OAT1-expressing cells was used to build a detailed confidence-ranked OAT1-centered metabolic interaction network that includes many small molecules with well-established functions in metabolic and signaling pathways (FIG. 1B). A final network by working through 5 stages:

Stage 1: Prediction of Metabolites Affected by the Deletion of OAT1—

Figure 1C:
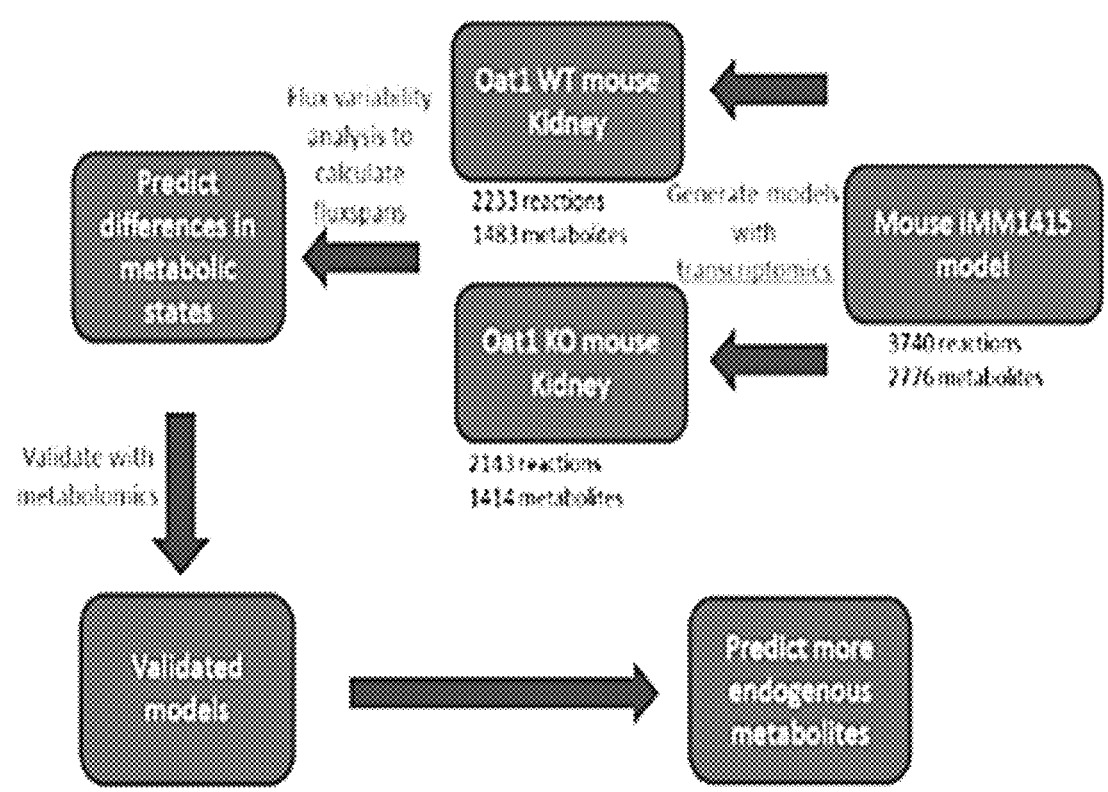

The first phase involved a systems biology approach in which transcriptomic data derived from the Oat1-KO mouse was integrated into the mouse GEM, iMM1415, to predict metabolites potentially affected by the absence of this transporter (FIG. 1C). Context-specific wild type (WT) and knock-out (KO) models were constructed from kidney gene expression data using the Gene Inactivity Moderated by Metabolism and Expression (GIMME) algorithm with iMM1415. This systems biology approach simulates the metabolic state of a tissue/organ based on transcriptomic data and the execution of specific biological processes by converting the metabolic network into mathematical equations followed by the application of linear programming to calculate a solution of fluxes (i.e. measurement of rate of production or depletion of metabolites) for each of the reactions. The generated models were confirmed to produce many of the small molecules requisite for the normal physiologic function of kidneys.

FVA, which calculates the boundary points of the steady state solution space, is one of most common constraint-based approaches used in investigations of the effects of gene deletion on a system; however, it requires an appropriate objective function (e.g. biomass production, ATP production, substrate uptake) that yields realistic flux distributions. However, the current metabolic models do not adequately encapsulate the in vivo metabolic alterations likely resulting from the loss of the drug transporter (OAT1) in a complex organ, forcing approximations to the data to gain some understanding of the in vivo role of OAT1 in metabolism. Thus, whereas several objective functions were considered, including the biomass objective function, the ATP objective function and the renal objective function, it was ultimately decided to use the biomass objective function because it is: 1) comprised of many metabolites involved in core cellular processes including those involved in regulating/modulating cell maintenance; and 2) applicable to non-proliferative cells, which either produce or consume these metabolites. Furthermore, many of the essential metabolites involved in regulating/modulating cell maintenance (e.g. Krebs cycle intermediates, prostaglandins, vitamins, uric acid, and polyamines) are transported by OAT1 and/or other closely related SLC22 family members. (Note that, in the simulations and comparative analyses between the wild type and knock-out models, the algorithm did not optimizing for growth, thus assuming that biomass is being maximized, but rather only that the biomass components can be produced by the cells, which we know to be the case, biologically.)

To increase the sensitivity of model predictions, a broad constraint at this initial stage of investigation was used, allowing the inclusion of all possible metabolites that were then ranked in confidence based on the application of pharmacophore screens, as well as available data on their ability to directly interact with OAT1 (from either in vivo metabolomics data or pharmacokinetic data). The resulting WT and KO models consisted of 2233 and 2143 reactions, respectively (FIG. 1C). FVA was used to compare metabolic differences and to find the maximum and minimum flux values for each reaction in the network, enabling the calculation of flux span ratios of the KO over WT for each reaction. Reactions with flux span ratios equal to 1 indicated no change in reaction activities due to the deletion of Oat1; flux span ratios less than 1 implied decreased reaction activities, whereas ratios greater than 1 indicated increased reaction activities. It was assumed that reactions that require transport of metabolites would change in the OAT1 KO, and 1026 reactions with altered activities were identified, including 321 exchange/transport reactions, which were responsible for the handling of 177 metabolites. After excluding water and other uninformative molecules, 146 metabolites remained, which were predicted to be linked to OAT1-mediated transport.

Stage 2: Validation of the Models Using In Vivo Data from the Oat1-KO, as Well as with In Vitro/Ex Vivo Transport Data—

Multiple approaches were used to validate the metabolic reconstruction, as well as to provide a measure of confidence in the ability of the predicted metabolites to interact with OAT1. Initially, metabolomics data from the Oat1-KO were interrogated to determine whether experimental observations corresponded with computational predictions. Previous metabolomics profiles identified 36 metabolites (some of which are also signaling molecules), with significantly altered plasma and/or urine concentrations between the WT and Oat1-KO (FIG. 1B and FIG. 1C). Among these 36 metabolites, only 19 were actually included in the iMM1415 GEM, and direct comparison with this metabolomics data revealed that 10 of these 19 metabolites were predicted by the GEM analysis. Applying a hypergeometric test to this sample clearly indicates statistically significant enrichment in such metabolites in the population of 146 predicted metabolites (p<0.01), which suggests that the systems biology approach integrating transcriptomics data together with loosely constrained FVA modeling makes reasonable predictions of the in vivo metabolic differences between WT and KO.

In addition, because metabolites that interact with OAT1 would be expected to be affected by the absence of this transporter, a search of the literature was performed and a list of 108 metabolites for which kinetic data exists (i.e. Km and/or Ki) indicating interaction with OAT1 was identified. Among these 108 metabolites, 56 are present in the iMM1415 GEM, of which 21 were found within the 146 GEM-predicted metabolites. Once again, applying a hypergeometric test to this sample reveals statistically significant enrichment in OAT1-interacting metabolites in our population of 146 predicted metabolites (p<0.01). Moreover, combining the metabolomics results with the kinetic data generated a list of 65 non-overlapping metabolites with wet-lab support (either in vivo metabolomics or in vitro/ex vivo kinetic data) for interaction with OAT1 in the iMM1415 GEM and out of these 65 metabolites 24 were predicted by the systems biology analysis and applying the hypergeometric test indicates significant enrichment in OAT1-interacting metabolites among the 146 GEM-predicted metabolites (p<0.01). Taken together, the significant enrichment of the 146 GEM-predicted metabolites in OAT1-interacting metabolites indicates the utility of the loosely constrained systems biology approach utilized in the study.

Stage 3: Pharmacophore Analysis of Metabolites' Potential to Interact with OAT1—

As described above, the broad constraints were applied in Stage 1 to identify all possible reactions and maximize the prediction of potential endogenous metabolites and signaling molecules likely affected by the absence of this drug transporter. To generate an OAT1-centered interaction network, this broad list of metabolites was then filtered and ranked by their potential to interact with OAT1. QSAR and pharmacophore modeling have been used to analyze limited sets of OAT drugs/substrates. Although many drugs appear to be related to metabolites and signaling molecules, the availability of chemical libraries and computational tools have led to more systematic comparisons of metabolites, natural compounds, and drugs. Indeed, pharmacophores based on OAT1 metabolites have previously been used to virtually screen chemical libraries and identify potential inhibitors that have been experimentally validated. It was thus reasoned that the chemical features of known OAT1-transported drugs might be used to rank the predicted metabolites for their potential to interact with OAT1. In addition, some of these metabolites could then be prioritized for later wet-lab validation to assess direct interaction with OAT1. Therefore, OAT1 pharmacophore models based on a large set of well-established drug ligands were built.

Figure 3B:
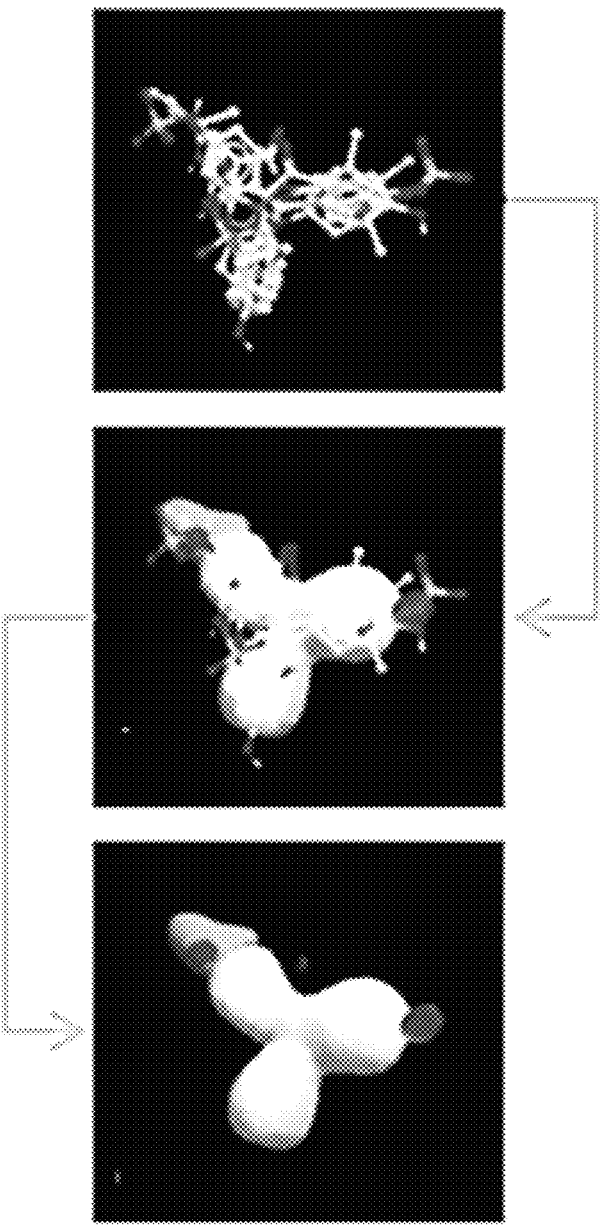
Figure 3C:
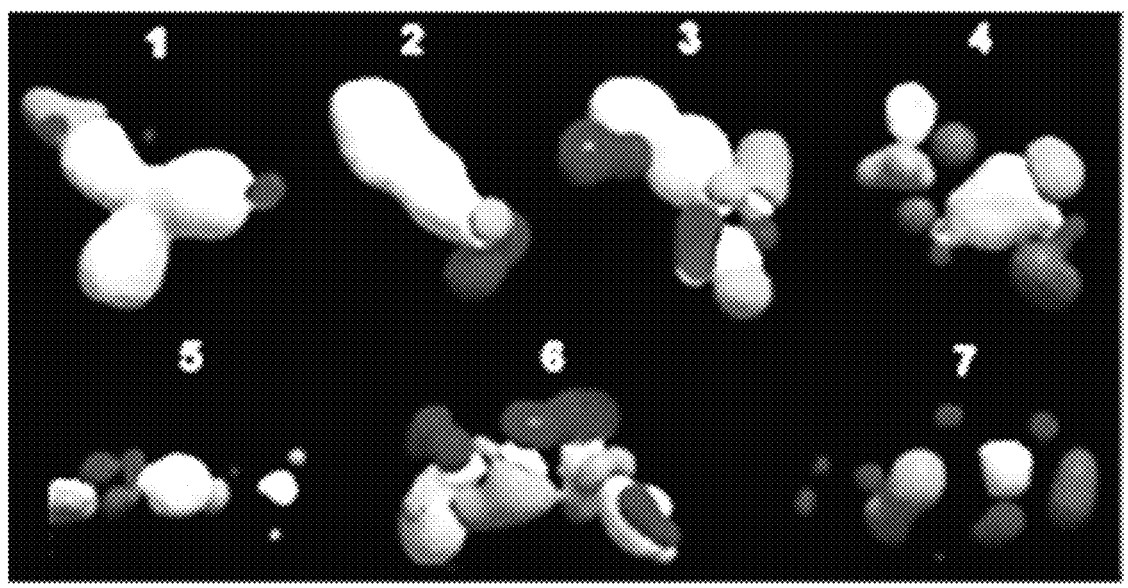
Figures 22A, 22B:
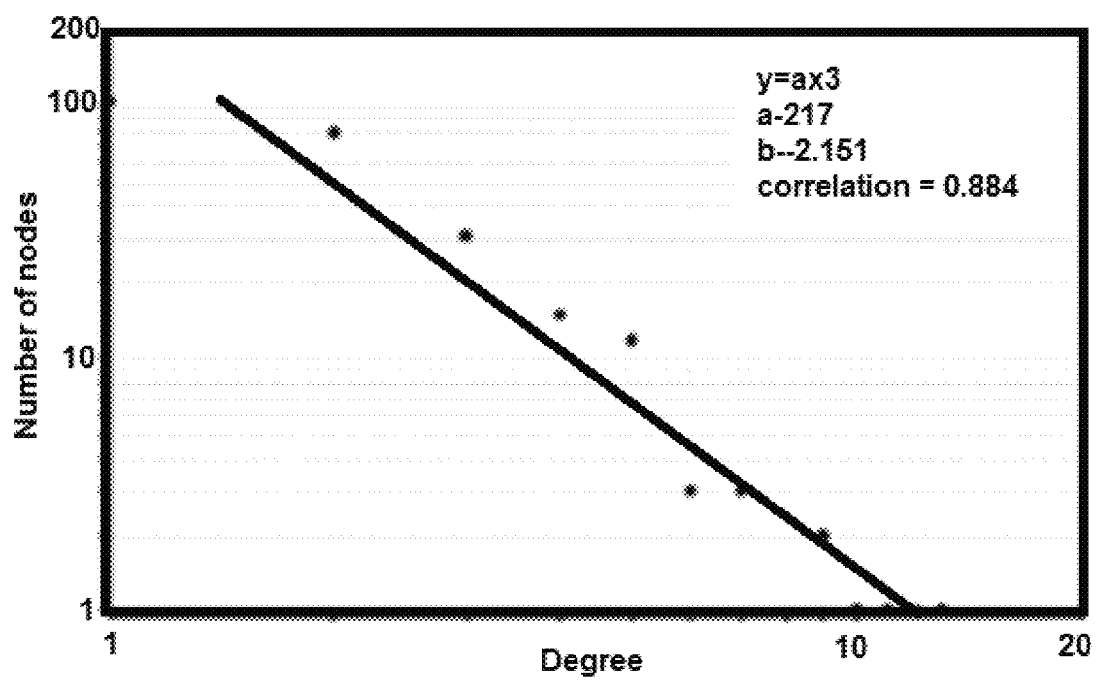
Figures 22C, 22D:
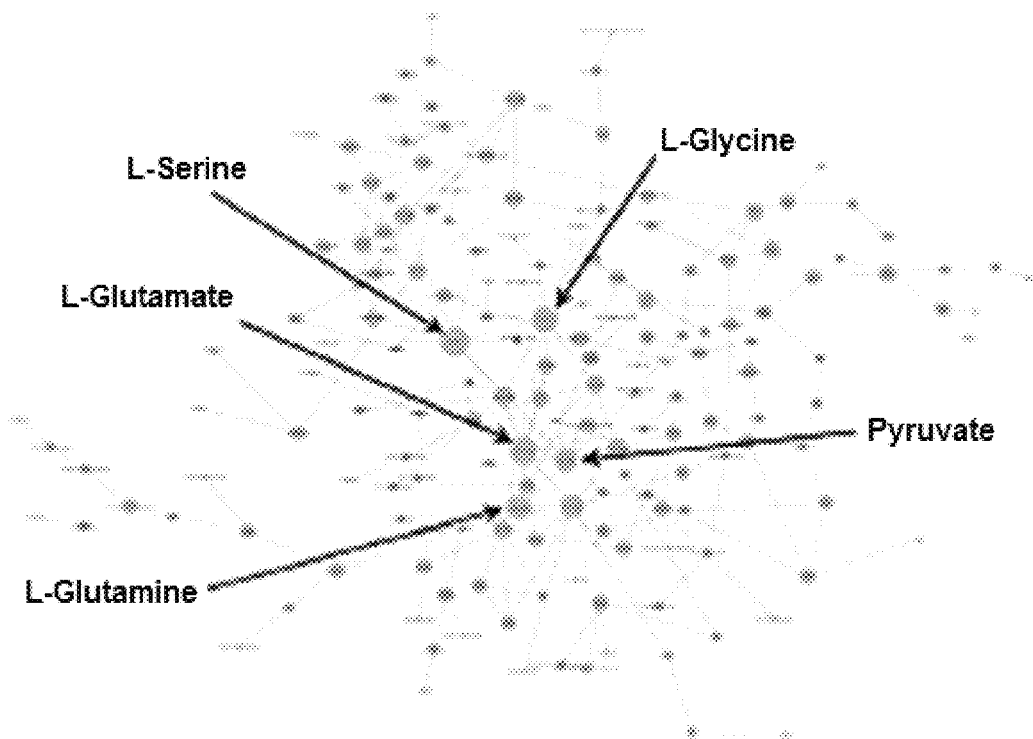

To construct pharmacophore models for OAT1, 61 drugs having a published Km or Ki less than 100 µM for OAT1 were selected as "actives" for model building and model validation; two-thirds of the drugs in this group (41 drugs) were used to build the pharmacophore models (training set), and one third (20 drugs) of the actives was used as a validating set (FIG. 19A). Because the drugs possess diverse chemical structures (consistent with the known multispecific nature of OAT1), they were first clustered into groups using their atomic property fields (APF) (e.g. hydrogen bond donors, hydrogen bond acceptors, SP2 hybridization, lipophilicity, sizes of large atoms, positive and negative charges, etc.) as discriminators. Thus, the training actives were grouped into 7 distinct clusters (FIG. 3A), and pharmacophore models were then built for each cluster based upon the alignment of its members (FIGS. 3B and C). FIG. 3B demonstrates how members of cluster 1 were first aligned, and "pharmacophore model 1" was built to represent the three-dimensional atomic properties shared among the members of that cluster. Then, the pharmacophore models were validated based on the validating set (known positives) and drugs from Drugbank database (serving as true negatives), and a ROC curve was generated (FIG. 22B). The calculated area under curve was 80.58, which supports the utility of these pharmacophores to identify OAT1-interacting compounds.

The 7 pharmacophores (FIG. 3C) were then used as three dimensional chemical space constraints for virtual screening of the predicted molecules that revealed that 74 of the 146 predicted metabolites satisfied the constraints and were therefore predicted to have direct interaction with OAT1. Of these 74 metabolites, 18 are known to have direct interaction with OAT1 based on previous experimental in vitro observations. Thus, compared with the original list of 146 metabolites that had 21 metabolites with kinetic data indicating interaction with OAT1 (prior to pharmacophore filtering), the percentage of metabolites known to have direct interactions was enriched about 2-fold (from 14.4% (21 of 146) to 24.3% (18 of 74) after filtering) and this enrichment in OAT1-interacting metabolites was found to be statistically significant by the hypergeometric test (p<0.01).

Stage 4: Wet-Lab Validation and Identification of Novel-OAT1 Ligands—

Figure 4A:
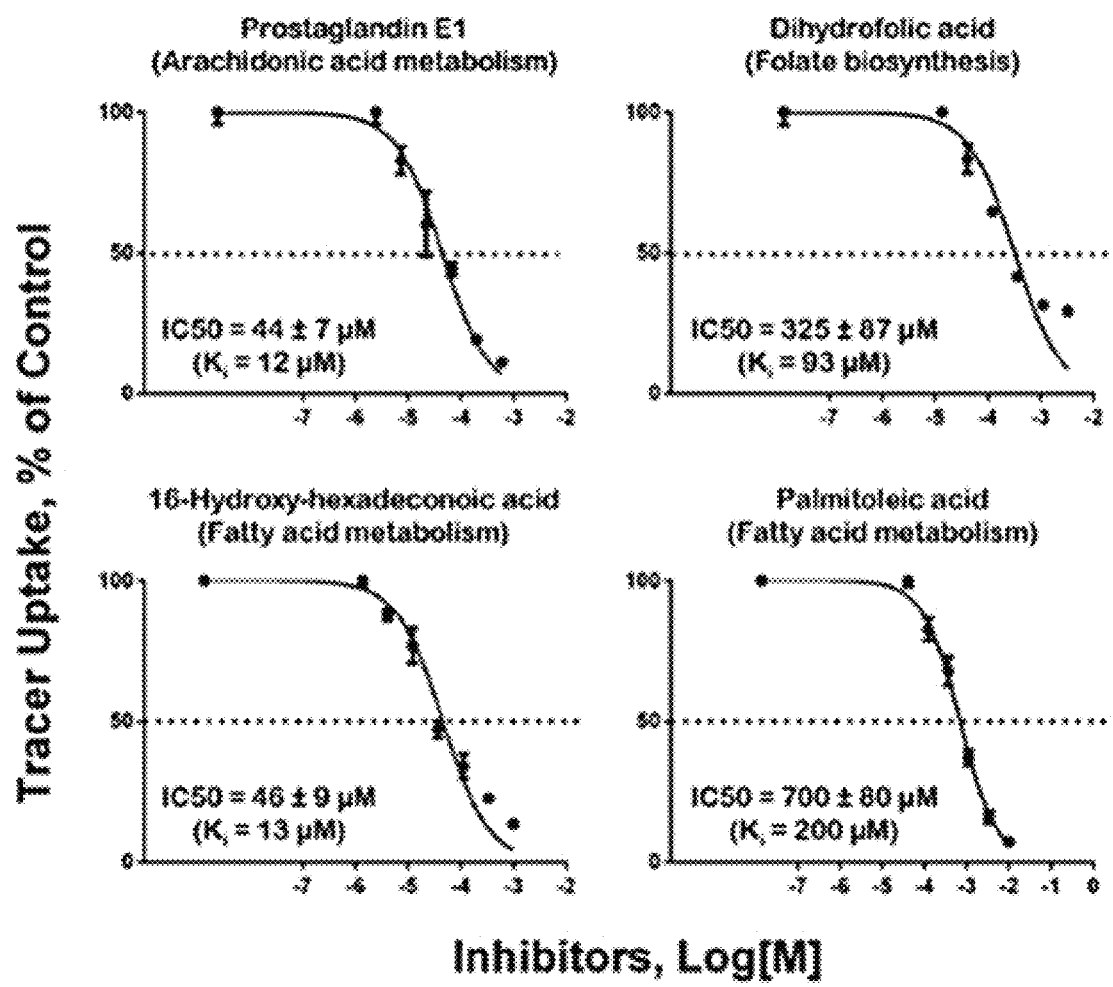

Based on their ability to fit the pharmacophore models, a subset of 8 commercially available metabolites out of the remaining 56 metabolites predicted to directly interact with OAT1 in the pharmacophore screen, but for which there is no wet-lab kinetic data indicating actual interaction with this transporter, were then randomly selected for validation in wet-lab transport assays. Of these 8 metabolites/signaling molecules, four were found to interact with OAT1 in transfected cells (FIG. 4A). These metabolites/signaling molecules were dihydrofolic acid, palmitoleic acid, 16-hydroxyhexadecanoic acid, and prostaglandin E1 with calculated Ki values of 93, 200, 13, and 12 µM, respectively (FIG. 23); values that are well within the documented range for many compounds shown to interact with OAT1. These metabolites are important in whole-body physiology, signaling, and cellular metabolism. For example, prostaglandin E1, an endogenous vasodilator, serves to increase peripheral blood flow, whereas dihydrofolic acid is required to synthesize both purines and pyrimidines. Palmitoleic acid, a long-chained fatty acid serving as a potential lipokine, is important in the regulation of lipid metabolism.

Taken together with the metabolomics and existing kinetic data described above, the number of wet-lab supported metabolites was increased and the application of a hypergeometric statistical test to the overall method for prediction and identification of novel OAT1 metabolites (the combined in silico and in vitro approach), indicates significant enrichment in the number of OAT1-interacting metabolites (p<0.01).

Stage 5: Construction of an OAT1-Centered Metabolic Interaction Network—

Figure 21A:
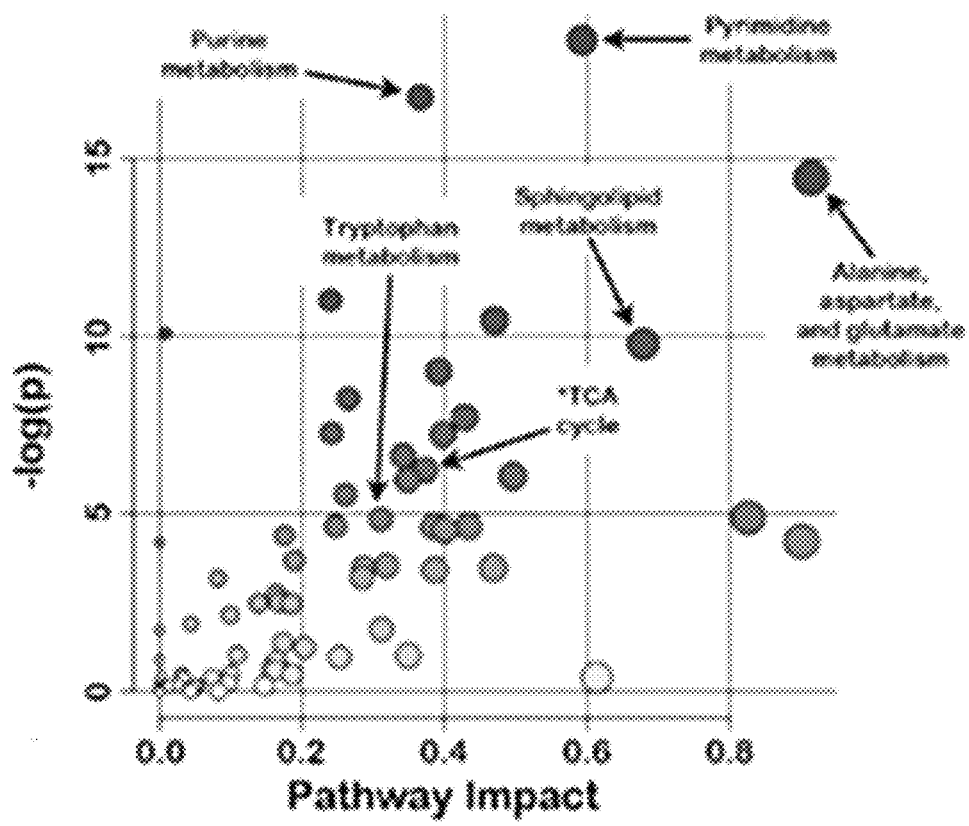
FIG. 21A-B shows pathway enrichment analysis of the OAT1-centered metabolic interaction network identifies several essential biochemical pathways affected by the absence of OAT1. (A) graph of pathway enrichment analysis comparing the −log(p) to the impact on the various pathways for the network metabolites. Some of the affected pathways are indicated with circles based on the p value (darker indicates a lower p value, whereas lighter indicates less significance) and sized based on the impact on the pathway (larger circles have a greater impact). Pathway impact accounts for both the number of affected nodes and its importance with the maximum importance of each pathway being 1. (B) the TCA cycle pathway is shown as an example of an affected pathway as it has the highest percentage of hits with wet-lab support (see Table 5). Affected pathway metabolites are depicted and those with wet-lab support for OAT1 interaction have a border. The number within the rectangle is the KEGG ID for each metabolite, seven metabolites shown are: C00022-pyruvate, C00149-malate, C00042-succinate, C00122-fumarate, C00158-citrate, C00311-isocitrate, C00026-2-oxoglutarate.
Figure 21B:
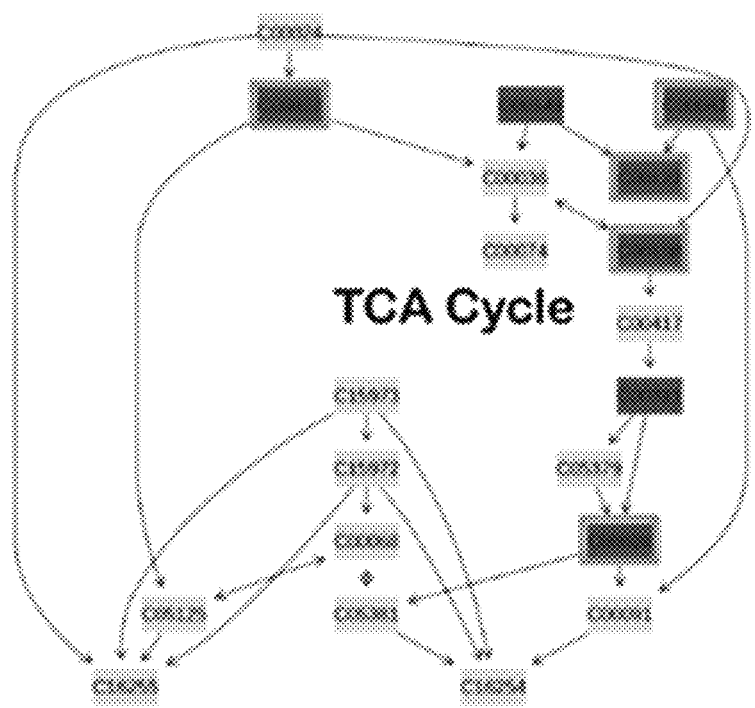

The next phase of this study involved construction and analysis of a substantially validated, confidence ranked OAT1-centered metabolite interaction network (FIGS. 5, 20, and 21). To link OAT1 to multiple metabolic pathways, an interaction network was built based on the results of the aforementioned systems biology/pharmacophore approach and the wet-lab data, using Metscape, a Cytoscape plug-in used to construct and visualize metabolic networks based on the KEGG database. The resulting broader OAT1-centered metabolic network consisted of a total of 253 metabolites, including 176 experimentally validated and/or computationally predicted and 77 "plus-one" (directly connected) metabolites (FIG. 5). Of these 176 metabolites, 73 had wet-lab support for interactions with OAT1 either by in vivo metabolomics from the knock-out or in vitro assays that were performed in this study or published. Moreover, ~3% of the 2272 (i.e. 78/2272) metabolites comprising the MetScape database at the time of analysis were among those for which OAT1-interaction data were available; however, within the 253 metabolites comprising the OAT1-interaction network more than 28% (i.e. 73/253) have been shown to interact with OAT1. This represented a significant enrichment for OAT1-interacting metabolites in the OAT1-centered interaction network (p<0.01). These metabolites were thus placed in the group termed "wet-lab" support and had the highest level of confidence for being part of an OAT1-centered metabolic network based on their ability to interact with OAT1.

Three other groups of metabolites were included, in order of level of confidence. The metabolites with the next level of confidence were those first predicted by GEM and which also passed pharmacophore filters; these were termed "metabolites with high confidence of interacting with OAT1". Metabolites only predicted by GEM (but having structures such that they did not pass the drug-based pharmacophore filters with high confidence) were classified as "metabolites likely to be affected indirectly." Finally, the remaining plus-one metabolites were termed "OAT1-first neighbor compounds" (FIG. 5). The network revealed that, in the revised OAT1-centered metabolite pathways, the majority of metabolites were interconnected to constitute a main component, and there were also a number of small self-connected components (FIG. 5); network parameters were measured and some are shown in FIG. 6. The metabolites within the network participated in more than 20 different canonical metabolic pathways, suggesting the broad importance of OAT1 in metabolism. Pathway enrichment analysis of these 253 metabolites was performed using the online bioinformatics resource, Metaboanalyst. This over representation analysis provides statistical information on the impact of the metabolites on various pathways (Table 5 and FIG. 21). The affected metabolite/signaling pathways included carbohydrate (e.g. Kreb's cycle, galactose metabolism, etc.), lipid (glycosphingolipid metabolism, bile acid biosynthesis, etc.), amino acid (alanine, aspartate and glutamate, etc.), nucleotide (purine and pyrimidine), and cofactor and vitamin (vitamin A, B2, B3, B5, B6, and B9) metabolism (Table 5; FIG. 21).

TABLE 5

Top pathways affected by OAT1 deficiency as determined by pathway analysis and ranked by the number of hits (%) with wet-lab support. The represented metabolic pathways are ranked according to their percentage of hits with wet-lab support. TCA cycle, tyrosine, and tryptophan metabolism are some of the most well validated pathways represented in the network.

| Top pathways | Total | Hits | p Value | FDR | Hits with wet-lab support | Hits with wet-lab support % |
|---|---|---|---|---|---|---|
| TCA cycle | 20 | 7 | 0.001972 | 0.011266 | 5 | 71.4 |
| Tyrosine metabolism | 76 | 17 | 0.000728 | 0.004852 | 10 | 58.8 |

TABLE 5-continued

Top pathways affected by OAT1 deficiency as determined by pathway analysis and ranked by the number of hits (%) with wet-lab support. The represented metabolic pathways are ranked according to their percentage of hits with wet-lab support. TCA cycle, tyrosine, and tryptophan metabolism are some of the most well validated pathways represented in the network.

| Top pathways | Total | Hits | p Value | FDR | Hits with wet-lab support | Hits with wet-lab support % |
|---|---|---|---|---|---|---|
| Alanine, aspartate, and glutamate metabolism | 24 | 12 | 5.34E−07 | 1.42E−05 | 7 | 58.3 |
| Butanoate metabolism | 40 | 12 | 0.000264 | 0.002344 | 7 | 58.3 |
| Arginine and proline metabolism | 77 | 13 | 0.032714 | 0.084423 | 7 | 53.8 |
| Tryptophan metabolism | 79 | 15 | 0.007898 | 0.033253 | 8 | 53.3 |
| Nicotinate and nicotinamide metabolism | 44 | 12 | 0.000697 | 0.004852 | 5 | 41.7 |
| Valine, leucine, and isoleucine degradation | 40 | 10 | 0.003935 | 0.018519 | 4 | 40.0 |
| Nitrogen metabolism | 39 | 13 | 4.24E−05 | 0.00565 | 5 | 38.5 |
| Glyoxylate and dicarboxylate metabolism | 50 | 12 | 0.002356 | 0.012563 | 4 | 33.3 |
| Propanoate metabolism | 35 | 10 | 0.001322 | 0.008134 | 3 | 30.0 |
| Glycine, serine, and threonine metabolism | 48 | 13 | 0.00045 | 0.003598 | 3 | 23.1 |
| Purine metabolism | 92 | 27 | 5.52E−08 | 2.21E−06 | 5 | 18.5 |
| Pyrimidine metabolism | 60 | 22 | 1.11E−08 | 8.85E−07 | 3 | 13.6 |

The most highly represented metabolic pathways having at least 7 metabolites are shown and ranked according to the validation percentage in Table 5 (validation percentage is equal to the number of "wet-lab supported" metabolites of the pathway divided by the total number of metabolites in the pathway). Among these pathways, the two with the highest "hits with wet-lab support" were tyrosine metabolism and TCA cycle (58.8 and 71.4%, respectively). The TCA cycle is noteworthy, because it includes metabolites known to be classical substrates of OAT1, such as α-ketoglutarate, citrate, fumarate, and succinate. Also included among these top-ranked pathways was tryptophan metabolism, which had considerable wet-lab support for 8 of 15 metabolites (53.3%), including anthranilate, xanthurenic acid, kynurenine, and indole-acetic acid, which are also putative uremic toxins associated with chronic kidney disease (CKD).

Network Analysis of the OAT1-Centered Metabolic Network.

NetworkAnalyzer, another Cytoscape plugin, was used to measure the global and local network parameters of the network. The whole network consisted of 32 connected "components" (253 nodes), including one main component (170 nodes), in which the majority of metabolites were interconnected, and 31 other small self-connected components. To determine if our networks were either random or scale-free, degree distribution, P(k), was measured, which calculates the probability of a selected node n having exactly k degrees (degree of a node is equal to the number of links it has to other nodes) (Lacroix et al., 2008). Networks with nodes that follow a Poisson distribution, in which most nodes have almost the same number of degrees, are said to be random networks; in contrast, networks that follow a power law, where $P(k) \sim k^{-Y}$, are called scale-free networks; most biological networks are thought to have a power law distribution with Y ranging between 2 and 3 (Barabasi and Oltvai, 2004). The OAT1-centered metabolic network was found to follow the power law distribution (FIG. 6A) and had Y value of 2.151; thus, our network, like most biological networks, was not random, but was scale-free. In a scale-free network, most nodes have only a limited number of links, and a few nodes have a very large number of links (these highly connected nodes are also called "hubs") (Barabasi and Oltvai, 2004). To identify the hubs, we measured the "degree" of individual nodes to investigate their local impact in the main component of the network since the main component was considerably more complex than the rest of the network. Metabolites with high degree, were found, including pyruvate, L-glutamine, L-glycine, L-glutamate, and L-serine (FIGS. 6B, 6C). Pyruvate is not only known to interact with OAT1 in vitro (Ahn et al., 2011), but it also serves as the precursor for the TCA cycle, which is the classical energy pathway linked with OAT1 function. In addition, the amino acids with high degrees are also important precursors for several metabolic pathways, and their importance in metabolism, as well as in the OAT1-centered network demonstrates, again, the significance of OAT1 in cellular metabolism.

To identify "hub" metabolic pathways, the degree values for metabolites from metabolic pathway having at least 7 metabolites were averaged (FIG. 6D). The main "hub" metabolic pathways (with average degree greater than 3.5) included vitamin B9 (folate) metabolism; urea cycle and metabolism of arginine, proline, glutamate, aspartate and asparagine; glycine, serine, alanine and threonine metabolism; and TCA cycle (FIG. 6D).

Metabolic Pathways Altered in Chronic Kidney Disease (CKD).

CKD causes "uremic syndrome," which affects many metabolic pathways (Ching-Ha Kwan and Beddhu, 2006; Guarnieri et al., 2010) and is thought to be partly due to the accumulation of so-called uremic toxins. OAT1 has been implicated in the metabolic abnormalities associated with diabetic nephropathy (Sharma et al., 2013), and Oat1 levels change in animal models of kidney disease (Komazawa et al., 2013; Liu et al., 2012; Monica Torres et al., 2005; Saito, 2010). Some of the small molecule uremic toxins of greatest clinical concern (e.g. indoxyl sulfate, p-cresol sulfate, kyurenine) are known OAT1 substrates; they also accumulate in Oat1 knockout mice (Wikoff et al., 2011). The recent application of targeted and untargeted metabolomics to patients with CKD and to animal models for this disease has made it possible to produce a list of metabolic alterations associated with CKD (Zhao, 2013). This list includes metabolites involved in key metabolic pathways, uremic toxins, and molecules considered to be biomarkers of CKD. We used this list to generate a putative CKD-associated metabolic network. After trimming, this CKD network contained a total of 322 metabolites.

Overlap of the OAT1-Centered Metabolic Network with the CKD-Associated Network.

As mentioned above, OAT1 has been implicated in CKD. To evaluate the potential role of OAT1 in the metabolic alterations of CKD, the OAT1-centered network was compared with the CKD network (FIG. 7). It was found that the two networks overlapped greatly. While no causality is implied, a role for OAT1 is thus supported in the modulation of many metabolites and metabolic pathways affected in CKD. For example, there were 113 overlapping metabolites between the models (44% of metabolites in the OAT1-centered metabolic network). Among them were metabolites that are both listed as potential uremic toxins and known to directly interact with OAT1 (Deguchi et al., 2004; Wikoff et al., 2011); these included xanthurenate, xanthine, L-citrulline, and hippurate. Apart from the "wet-lab supported" group of metabolites, other overlapping metabolites (e.g. sphinganine, hexadeocanoic, and dopamine) from the OAT1-centered metabolic network were predicted by the GEM reconstruction.

Example 2

Water-soluble probenecid was purchased from Molecular Probes (Eugene, Oreg.). The fluorescent tracers, 5-carboxyfluorescein and 6-carboxyfluorescein, and cationic drugs (loperamide hydrochloride, nebivolol hydrochloride, darifenacin hydrobromide, paliperidone, cisapride monohydrate, and halofantrine hydrochloride) were purchased from Sigma-Aldrich (St. Louis, Mo.).

Selection and Classification of Drugs Interacting with OAT1, OATS, OCT1, and/or OCT2.

A comprehensive literature and internet search was performed to compile a list of pharmaceutical drugs and tracers that interact with any of the four SLC22 transporters investigated in this study. Approximately 250 drugs were analyzed and the inhibition affinity (Ki) and/or the substrate affinity (Km) were used as a measurement of a given drug's interaction with a given transporter. This "interaction affinity" classified drugs as either high-affinity (i.e., Km or Ki≤100 µM), mid affinity (i.e., Km or Ki>100 µM, but ≤1000 µM), low-affinity (i.e., Km or Ki>1000 µM, but ≤2000 µM), or extremely low affinity (i.e., Km or Ki>2000 µM, but ≤12000 µM). Since these transporters share a great deal of similarity and can interact with the same compounds, albeit usually with different affinities, drugs interacting with two or more transporters with similar interaction affinities (i.e., both interact with high affinity) were excluded from the subsequent data mining analysis aimed at defining the physicochemical descriptors that separate OAT1, OAT3, OCT1, and OCT2.

The net charge states of the drugs at physiologic pH (i.e., 7.4) were then determined in the computational environment of ICM software (a commercially available computational chemistry software; Molsoft LLC, San Diego, Calif.). Drugs were considered "cationic" if their net charge was greater than zero, "anionic" if their net charge was less than zero, "neutral" if their net charge was equal to zero and they contained no charged atoms, or "zwitterionic neutral" if their net charge was zero but they contained an equal number of positively charged and negatively charged atoms. However, since it is possible for a drug to have more than one charged species coexisting at a given pH, the percentage of each charge species was determined using pH/concentration curves created using the chemicalize software ([www.] chemicalize.org; ChemAxon, Cambridge, Mass.), and the species percentages were calculated at three different pH values, 7.2, 7.4, and 7.6. Finally, total positive species percentage, total negative species percentage, total neutral species percentage, and total zwitterionic neutral species percentage were calculated for individual charge-species bar diagrams. The results were then plotted.

Collection and Preprocessing for Machine-Learning Analyses.

The pairwise comparison study employed in the machine learning analyses was limited to non-overlapping drugs (i.e., drugs which interacted with high affinity for only one transporter). The attributes to be compared in the machine-learning models were physicochemical properties of the drugs calculated using ICM (Molsoft), and tabulated in Konstanz information miner (KNIME), an open-source workflow platform for machine-learning (Beisken et al., 2013). Using ICM, about 50 physicochemical attributes of the drugs were calculated, including molecular quantum numbers, atom counts, bond counts, polarity counts, and topology counts. KNIME includes extensions capable of collecting data from three notable open source cheminformatics toolkits: RDKIT, Indigo, and CDK. Through the KNIME platform using RDKit, Indigo, and CDK, attributes were added to represent about 100 chemical features for each drug, such as molecular weight, molecular volume, Log P, Log S, polar surface area, etc. In addition to these physicochemical attributes, a class variable was also added to represent the transporter with which a given drug would interact.

After collecting the data, Weka, KNIME, and Excel were used to preprocess the data. Weka (cs.waikato.ac.nz/ml/weka) is an open source collection of machine-learning algorithms developed by the University of Waikato and is bundled together with tools for preprocessing data to make it more easily understood by the machine-learning algorithms. For example, the raw data extracted from KNIME and ICM contained some attributes that were overlapping, empty, or constant, and these were eliminated. The second step was to use Weka's attribute-selection feature, Chi Square Evaluator, to rank the attributes according to their contribution to predicting the class variable. The Chi Square procedure is applied individually to each variable by first binarizing real-valued variables and then testing the expected-minus-observed counts with respect to the class, where the expected counts are assumed to be independent; larger counts result in a higher Chi Square statistic and suggest nonindependence (Agresti and Coull, 1996).

Machine-Learning Analyses.

After the data was compiled and preprocessed, machine-learning algorithms were employed to develop models. In this case, drugs that had a "high affinity" for the transporters OAT1, OAT3, OCT1, and OCT2 were treated as "instances," and the physicochemical properties of the drugs were used as "attributes." Six pairwise comparison studies were conducted: OAT1 versus OCT1, OAT1 versus OCT2, OAT3 versus OCT1, OAT3 versus OCT2, OAT1 versus OAT3, and OCT1 versus OCT2; as described above, in each comparison study, "overlapping" drugs, or ones that displayed high-affinity interaction with both of the transporters being compared, were eliminated from the analysis.

Several Weka machine-learning models were used: decision trees, decision rules, support vector machine, Bayesian models, and neural networks. Classification models that were well validated were obtained by several different techniques, but the preference was for those models that could help explain transporter binding/interaction data. For example, neural network models are a "black box" model, so, although they are not as useful as decision rule or decision tree models for defining distinguishing properties, they are still accurate classifiers. Comparable classification success rates with several different algorithms demonstrate that there is a boundary related to transporter selectivity. Also of note, within a given model, depending on the features of the model selected, different decision trees were generated, probably owing in part to the overlap in molecular characteristics captured by various attributes. Multiple iterations of the algorithms and parameters were explored to arrive at models with the best validation scores.

In a decision tree, each node is a variable, and each branch represents a data split that depends on the value of the variable. An instance of the data determines a path down the tree, which ultimately leads to a leaf node that represents a class prediction. The decision tree is induced by ranking how well each variable can split the data at a decision node (starting with the root), splitting the data, and repeating the process for each branch. As the data gets split more and more, eventually each node mostly reflects one class or the other, and the branching stops. Typically, trees are induced and then lower levels are pruned back to improve performance in a cross-validation procedure. Compared with other techniques, a decision tree is more interpretable because the decisions are easily described.

A random forest is an ensemble of decision trees in which each tree is trained with different bootstrap samples (1000 in this case). The ensemble is averaged together to produce an aggregate classification. The trees are made slightly decorrelated by limiting the choice of variables during tree induction so that different combinations of variables can fill out the tree branches. An additional benefit of the bootstrap is that one can estimate the detrimental effect of variable permutations on predictions for each "left out of bag" sample. That effect is averaged and normalized over all trees, leading to a measure of variable importance. Because a decision tree is nonlinear in the way it partitions the input, the variable importance is potentially a measure of both interaction and main effects (Svetnik et al., 2003).

Statistical Analysis.

In addition to the machine-learning approach, statistical tests were used to study the significance of the calculated differences between ligand transporter interactions. In each of the pairwise comparison studies, t tests were performed on the physiologic properties to determine if the differences in the mean values for each were statistically significant between the two groups of drugs. Then, the physiologic properties were ranked according to their P values.

Creation of Pharmacophore Hypotheses.

Pharmacophore models were built in ICM, which performed clustering, alignment, and pharmacophore building on the basis of the atomic property field (APF) of the drug. APF considers the three-dimensional representation of atomic properties, such as hydrogen bond donors, hydrogen bond acceptors, SP2 hybridization, lipophilicity, size of large atoms, and positive and negative charges (Totrov, 2008). High affinity drugs were chosen as "actives." Since the actives were diverse in their three dimensional molecular structures, hierarchical clustering of actives on the basis of APF was first done to separate them into groups. Actives among the each group were then aligned, and a pharmacophore model was generated from the aligned drugs. To be included, each group needed to comprise a minimum of three drugs with dissimilarity score less than or equal to 0.25. The dissimilarity score is an indication of how similar two compounds are in APF and ranges from 0 to 1, where 0=similarity and 1=dissimilarity. Thus, clusters containing drugs that were too dissimilar would not be considered for pharmacophore model generation. APF properties were determined for each pharmacophore model using ICM, and the vectors of each APF property across all the models were added to calculate the total for that property. More extensive descriptions of this type of approach can be found elsewhere (Khan et al., 2012).

In Silico Screening and Uptake Assays.

Pharmacophore models were then used to virtually screen the Drug Bank database with the ICM computational software. Some top hits were selected for further testing in an in vitro transport/uptake assay for interaction with selected transporters. Uptake assays, with probenecid serving as a negative control, were performed using Chinese hamster ovary cells constitutively expressing mouse Oat3 or Oat1, as previously described (Ahn et al., 2009; Wu et al., 2013, 2015; Zhu et al., 2015).

The overall goal was to determine whether a formal systematic analysis of the physicochemical descriptors of drugs that interact with SLC22 transporters could: 1) identify properties, other than charge, that would help in predicting whether a ligand interacts with an OAT or OCT, and 2) uncover additional molecular properties of ligands predictive for interaction with prototypical members of these subfamilies (OAT1 versus OAT3 and OCT1 versus OCT2). A literature search identified a large number of pharmaceutical drugs and tracers with the ability to interact with OAT1, OAT3, OCT1, and OCT2 (i.e., 103, 105, 96, and 81, respectively) at all affinity levels (~5 µM to 5 mM); unless otherwise specified, machine-learning analysis, statistical analysis, and pharmacophore modeling were performed using drugs interacting with the transporters in the "high-affinity" range (i.e., ≤100 µM).

Because there is only limited direct transport data (Km) for these transporters compared with the amount of inhibition data (Ki), the analyses (Ki combined with Km) perforce is weighted toward inhibition data. The literature seems to assume competitive inhibition with a transported substrate (e.g., labeled para-aminohippurate or triethanolamine), but in nearly all cases the type of inhibition is not formally established by accepted biochemical criteria. This appears to be a general issue for most, if not all, solute carriers and ABC drug transporters (Matsson and Bergstrom, 2015). Nevertheless, the decision tree analyses described below was also carried out for those drugs with inhibition (Ki) data alone (excluding those drugs that had Km data), and generally similar results were obtained for these comparatively large datasets. The analysis was also attempted on the much smaller sets of drugs for which Km data were available; although a trend similar to the "Ki plus Km analysis" and the "Ki analysis" was often seen, there did not appear to be large enough samples to achieve clear results.

OAT3 has Greater Capacity to Interact with Drugs of Positively-Charged Species and Zwitterionic-Neutral Species.

Figure 11A:
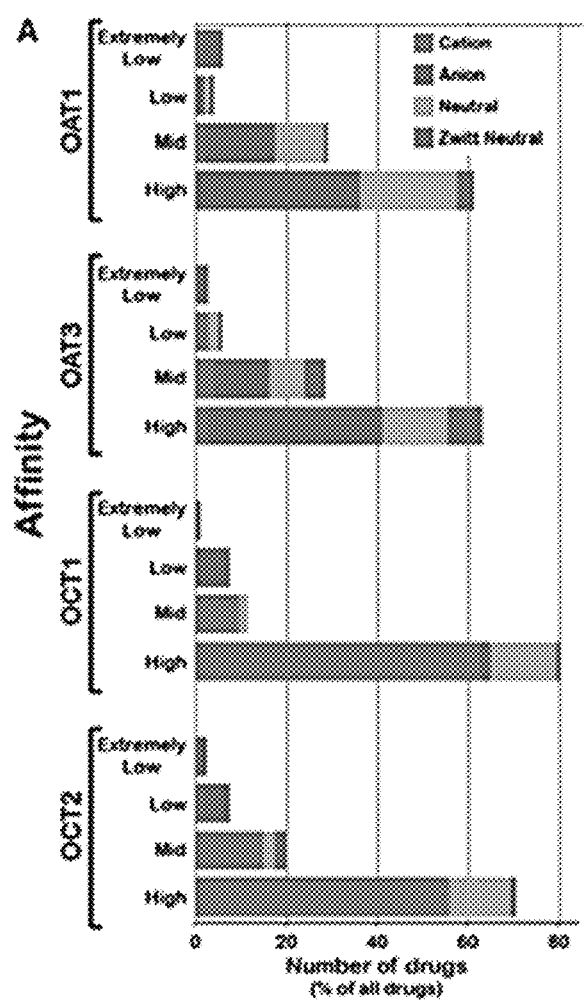
FIG. 11A-C shows drug transport characteristics for select drug transporters. (A) The distribution of charge states for pharmaceuticals that interacted with each of the transporters at various binding affinity ranges. The charge states of the pharmaceuticals were defined by considering the number of positive charges and negative charges calculated in ICM at the environment of pH=7.4. The charge states are scaled according to the legend in the upper right-hand corner of the graph. (B) The charge-species composition diagrams for the transporters. The charge-species composition for individual pharmaceuticals was measured on the basis of the pH/concentration curves found in chemicalize.org (an online compound database supported by ChemAxon), which were then grouped according to the transporters with which the pharmaceuticals interacted. The diagrams could indicate the capability of the transporters to interact with various charge species. The charge states are colored as defined in the legend in A. (C, D) Summary of the total percentage of various charge species for each transporter on the basis of the results of charge-species composition diagrams. The potential capability of OAT3 to interact with positively charged and zwitterionic species (arrow) was thereby clarified.
Figure 11B:
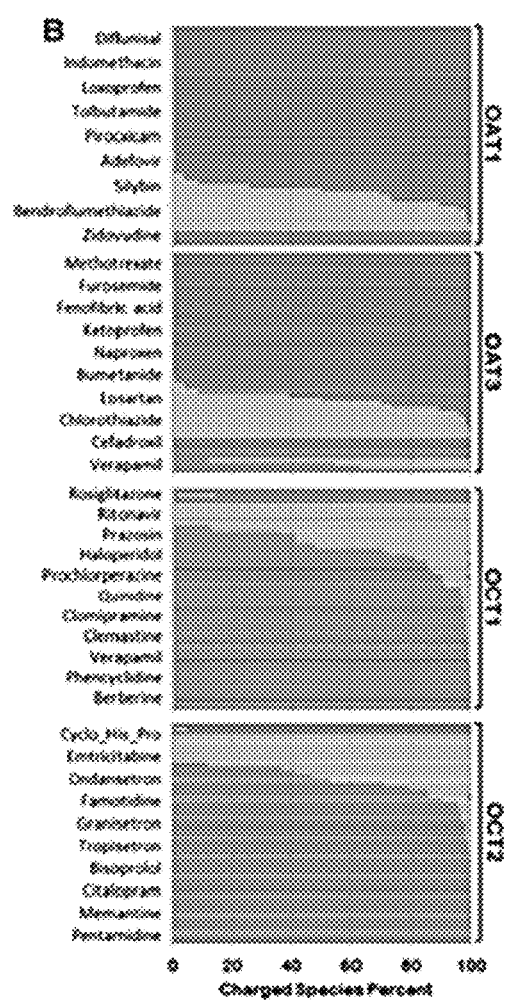
Figure 11C:
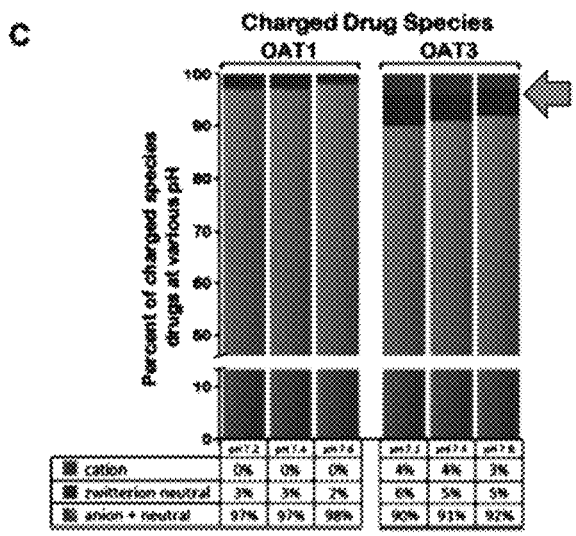
Figure 11D:
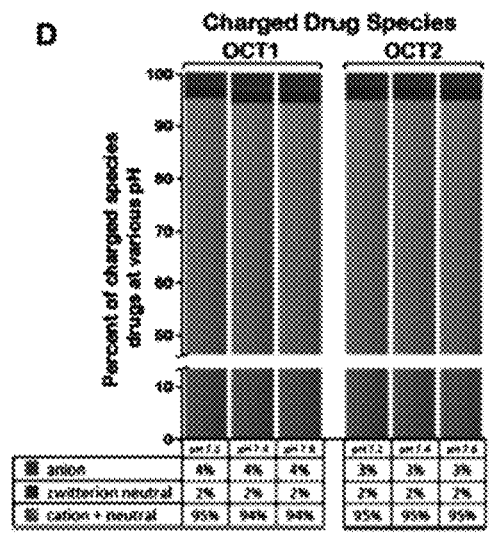

On the basis of the charge-species bar diagrams for individual transporters at pH 7.4 (FIGS. 11A and B), it was noted that the charged-species with which OAT1 and OAT3 mainly interacted were negatively charged (i.e., anionic), whereas OCT1 and OCT2 mainly interacted with positively charged species (i.e., cationic). Although the next most prevalent charged species with which both OATs and OCTs interacted were the neutral species, all four transporters interacted with zwitterionic-neutral species as well (FIG. 11). Notably, OAT3 (compared with OAT1) exhibited a greater ability to interact with zwitterionic-neutral species, as well as those with a charge opposite to that suggested by the name "organic anion transporter" (i.e., organic cations) (FIG. 11). At physiologic pH (i.e., pH 7.4), OAT1 does not interact with any positively charged species with high affinity; in contrast, OAT3 was able to interact with positively charged species at all affinities (which constituted 3.55% of species with which OAT3 interacts) (FIG. 11C). Both OCT1 and OCT2 interacted with negatively charged species, and the total negatively charged species percentages were 3.80% and 3.17%, respectively (FIG. 11D). Finally, the four transporters interacted with zwitterionic-neutral species to varying degrees; the total zwitterionic-neutral species percentages for OAT1, OAT3, OCT1, and OCT2 were the following: 2.75%, 5.44%, 1.78%, and 2.15%, respectively (FIG. 11). Thus, among these SLC22 transporters, OAT3 had the greatest ability to interact with zwitterionic-neutral species. To determine how well individual transporters interacted with "oppositely charged" and zwitterionic-neutral species together, the total percentages of "oppositely charged" species percentage plus zwitterionic-neutral species percentage for each transporter were explored (FIGS. 11 C and D). Among the four transporters, OAT3 had a much higher total percentage than the rest of the transporters (the value for OAT3 was 8.98%, whereas the values for OAT1, OCT1, and OCT2 were 2.75%, 5.58%, and 5.33%, respectively) (FIG. 11). This began to suggest to that, although OCT1 and OCT2 may be somewhat similar in their ligand specificities, OAT3 might be quite different than OAT1 especially with respect to the ability to interact with cations and zwitterions and may have more similarity (in terms of ligand preference) to OCTs than previously appreciated. This hypothesis was more formally explored in the studies below.

Effect of pH on the Ability of Transporters to Interact with Charged and Zwitterionic Neutral Drugs.

In addition to analyzing pH 7.4, analysis was performed on varying the pH of the solution in silico might change the composition of charged species with which each of the transporters interacted. At different pH levels the percent composition of charged species for drugs considered to be anionic, cationic, or zwitterionic at pH 7.4 would be expected to vary. In a more acidic environment, drugs would be protonated and contain more positively charged species, whereas in a more basic environment, drugs would be deprotonated and contain more negatively charged species. This would affect the percent composition of the charged species for a particular drug (anion/cation/zwitterion) with which individual transporters potentially interacted at a particular pH (FIGS. 11C and D). The sum of the positively charged species percentage and zwitterionic-neutral species percentage for drugs that interact with the organic anion transporters OAT1 and OAT3 increased as pH decreased, and the sum of negatively charged and zwitterionic species of the organic cation transporters, OCT1 and OCT2, increased when pH shifted toward the basic direction. In addition, it was found that OAT3-interacting drugs (compared with drugs interacting with OAT1, OCT1, and OCT2) probably changed most dramatically throughout the pH range of 7.2-7.6; when pH was either lowered or increased, the sum of the total positively charged and zwitterionic-neutral species for OAT3-interacting drugs changed from 8.31% to 9.93% as the pH was lowered from 7.6 to 7.2. In contrast, the sum of those values for OAT1, OCT1, and OCT2 changed minimally (FIGS. 11C and D).

Ligand Overlap Between OAT1 and OAT3 and Between OCT1 and OCT2.

Figure 12:
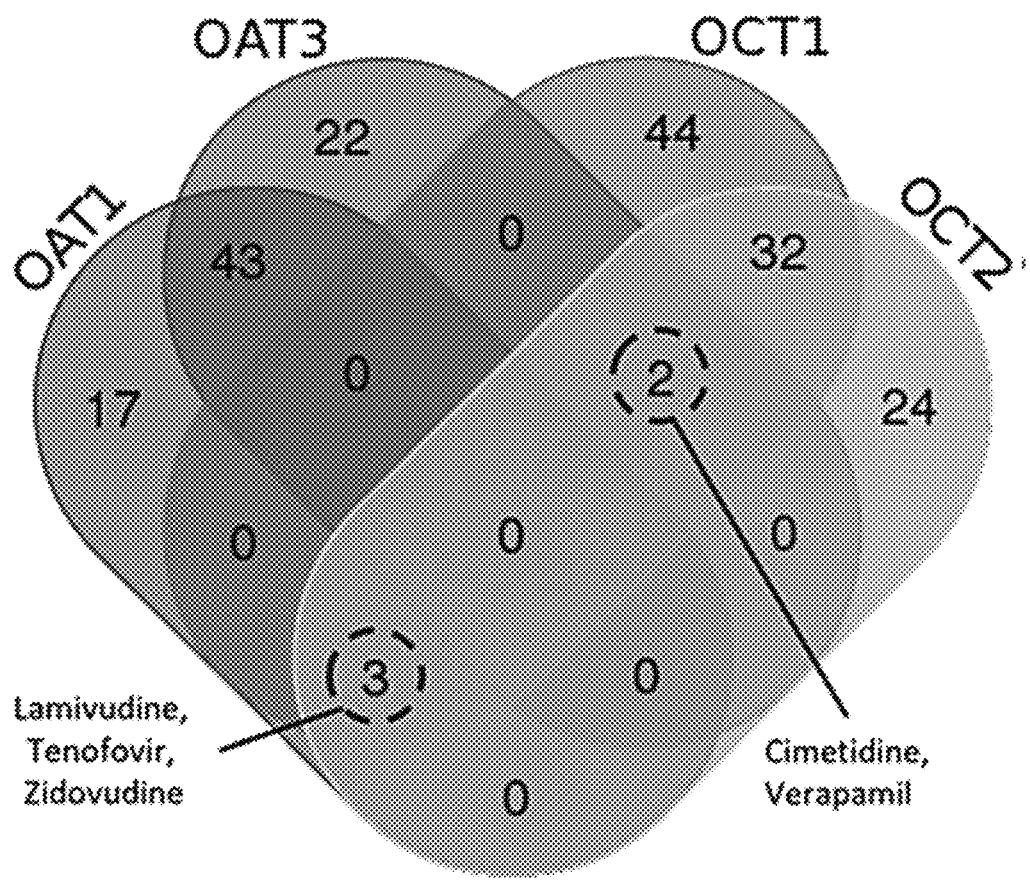
FIG. 12 shows substrate overlap among transporters. The Venn diagram demonstrates the substrate specificity and substrate multi-specificity between the transporters. Drugs found to be overlapping between the various transporters were excluded for the subsequent machine-learning analysis. Note: Although cimetidine and verapamil can bind OAT1 as well (Ahn et al., 2009), the affinity is roughly 10-fold less compared to OAT3.

OAT1 and OAT3 were found to share a number of high-affinity ligands with ~50% of the drugs showing affinities ≤100 µM for both organic anion transporters; likewise, OCT1 and OCT2 also shared many high-affinity ligands, with ~35% of these drugs displaying high-affinity interactions for both organic cation transporters (FIG. 12). Comparisons of OAT high-affinity ligands with those of the OCTs revealed much less overlap, with only ~1.8% of OAT1 and ~1.2% of OAT3 high-affinity drugs also being able to interact with the organic cation transporters at affinities ≤100 µM (FIG. 12), which is consistent with known ligand differences between OATs and OCTs. To identify subtle differences in ligand specificity between transporters, the overlapping drugs (i.e., those interacting with two transporter with high affinity) were excluded from the subsequent data-mining analysis aimed at defining the physicochemical descriptors that separate OAT1, OAT3, OCT1, and OCT2.

Machine-Learning Analysis: Results of Exemplary Models for OAT1 Versus OCT1.

A number of machine-learning approaches were initially applied. Although comparable results were generally obtained, decision trees developed using the J48 algorithm and random forest are discussed in detail for all the pairwise comparisons. Since in contrast to some of the other approaches, which are more like "black boxes" (e.g., neural networks), these models not only classified the data well, but provided a very logical way to demonstrate how physicochemical properties of the ligands affect the binding interaction between ligands and transporters. Of note, comparable classification success rates were obtained using different approaches, which suggests analyzable boundaries related to transporter selectivity.

Differences in Substrate Specificity are More Probably Between OAT1 and OAT3 than Between OCT1 and OCT2.

Table 6 shows the summary of weighted-average receiver operating characteristic (ROC) areas for the six decision tree models on the basis of high-affinity drugs when 10-fold cross validation is performed. These were: OAT1/OCT1, OAT1/OCT2, OAT3/OCT1, OAT3/OCT2, OAT1/OAT3, and OCT1/OCT2. Most decision tree models were well validated, and only two trees had ROC areas less than 0.80, which were the trees for OAT1/OAT3 and OCT1/OCT2. This was probably owing to the fact that ligands for the two OATs and two OCTs were highly similar, and it is difficult to build a decision tree model to identify and predict differences. Nevertheless, the ROC areas for OAT1/OAT3 was 0.795, and that for OCT1/OCT2 was 0.639 (Table 6), indicating that the functional differences between OAT1 and OAT3 were more easily discriminated than those between OCT1 and OCT2. This is an important point for the analyses that follow.

TABLE 6

Weighted-average ROC areas: performance validation of various decision tree analyses.

| | High-Affinity Drugs | | | | Mid-Affinity Drugs | |
| --- | --- | --- | --- | --- | --- | --- |
| | Charge Included | | Charge Excluded | | Charge Included as an Attribute | |
| Transporters Compared | Correctly Classified | ROC Area | Correctly Classified | ROC Area | Correctly Classified | ROC Area |
| OAT1/OCT1 | 86.57% | 0.905 | 80.60% | 0.823 | 82.50% | 0.874 |
| OAT1/OCT2 | 83.33% | 0.932 | 78.95% | 0.835 | 82.22% | 0.868 |
| OAT3/OCT1 | 86.33% | 0.880 | 77.70% | 0.764 | 80.00% | 0.880 |
| OAT3/OCT2 | 93.28% | 0.932 | 72.27% | 0.774 | 70.83% | 0.779 |

TABLE 6-continued

Weighted-average ROC areas: performance validation of various decision tree analyses.

| | High-Affinity Drugs | | | | Mid-Affinity Drugs | |
| --- | --- | --- | --- | --- | --- | --- |
| | Charge Included | | Charge Excluded | | Charge Included as an Attribute | |
| Transporters Compared | Correctly Classified | ROC Area | Correctly Classified | ROC Area | Correctly Classified | ROC Area |
| OAT1/OAT3 | 69.77% | 0.795 | — | — | 86.37% | 0.722 |
| OCT1/OCT2[a] | 66.67% | 0.639 | — | — | 45.45% | 0.450 |

The table summarizes the results using 10-fold cross-validation of machine-learning decision tree models for: 1) high-affinity drugs (with affinity less than 100 µM), 2) high-affinity drugs without using charge as an attribute, and 3) mid-affinity drugs (with affinity between 100 and 1000 µM).
[a]Note the poor results in the OCT1/OCT2 analysis are probably attributable to a small data set of six and five instances. —, results for OAT1/OAT3 and OCT1/OCT2 were inconclusive when charge was excluded.

Substrate Preferences Between OATs and OCTs Appear to be Mostly Attributable to Charge.

When an OAT was compared with an OCT in decision tree analysis, it was found that the first two physicochemical attributes that separated an OAT from an OCT were the number of negative (nof_negCharge) and positive charges (nof_posCharge) (FIG. 13). This is consistent with previous experimental data across mammalian species for many OAT1 and OCT1 ligands that include not only drugs, but also metabolites and toxins. Drugs that had the "number of negative charge greater than zero" were classified as OAT-interacting; in contrast, drugs that had the "number of positive charge greater than zero" interacted with OCTs (FIG. 13). Although this is compatible with the simple view that OATs transport anions and OCTs transport cations, as describe elsewhere, a more complex picture emerged with further analysis. For example, even with pairwise comparisons, after charge, the next determinant attribute seen in most trees was SP3 character: Those drugs with greater SP3 values are classified as OCT drugs. This suggested that it was more probable that drugs with more three-dimensional and less planar character would turn out to be OCT ligands.

Figure 14:
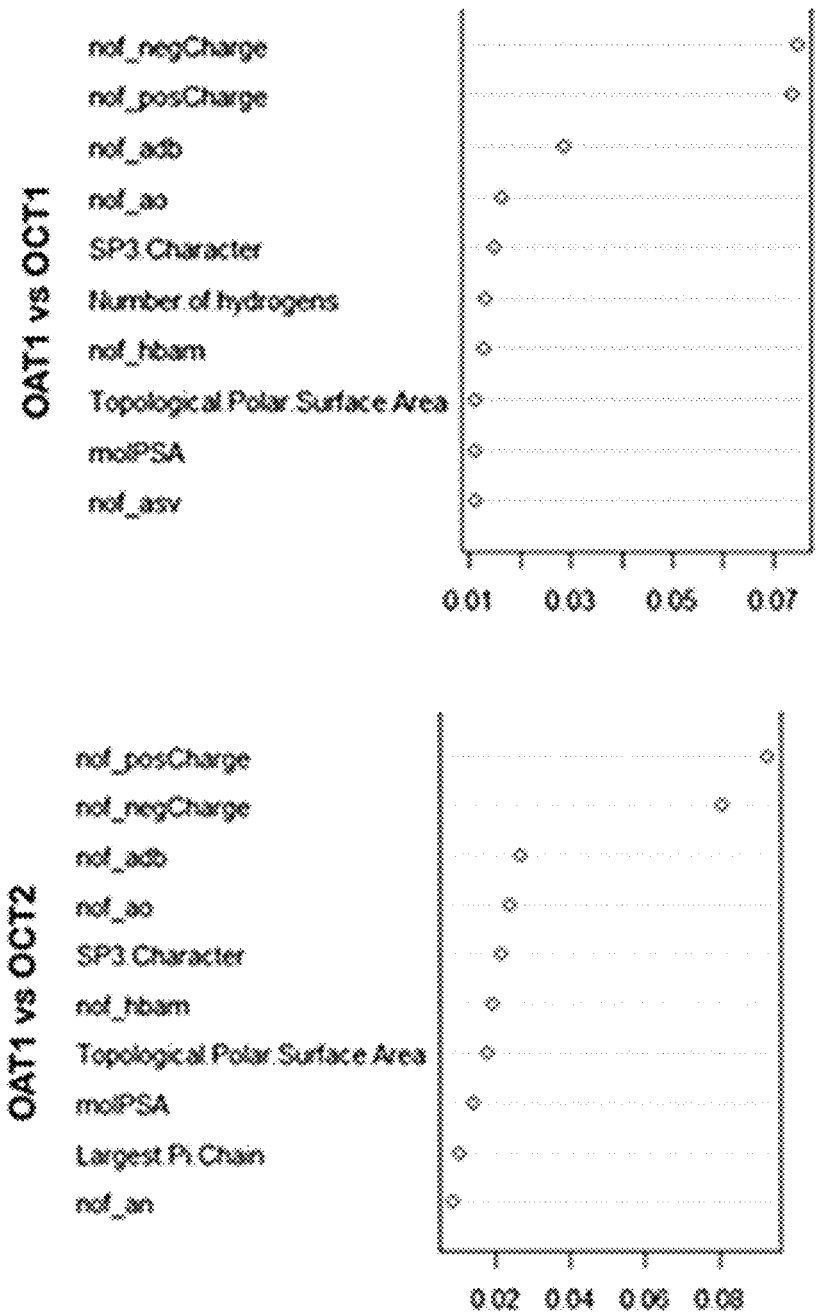
FIG. 14 shows results on the basis of the random forest analyses. Variable importance plots showing comparisons for drug attributes predicting interaction with transporters. Importance of attributes are ranked from the upper right of the plot (most important) to the lower left (least important). As discussed in the text, these results are highly comparable to the results from decision trees.
Figure 14:
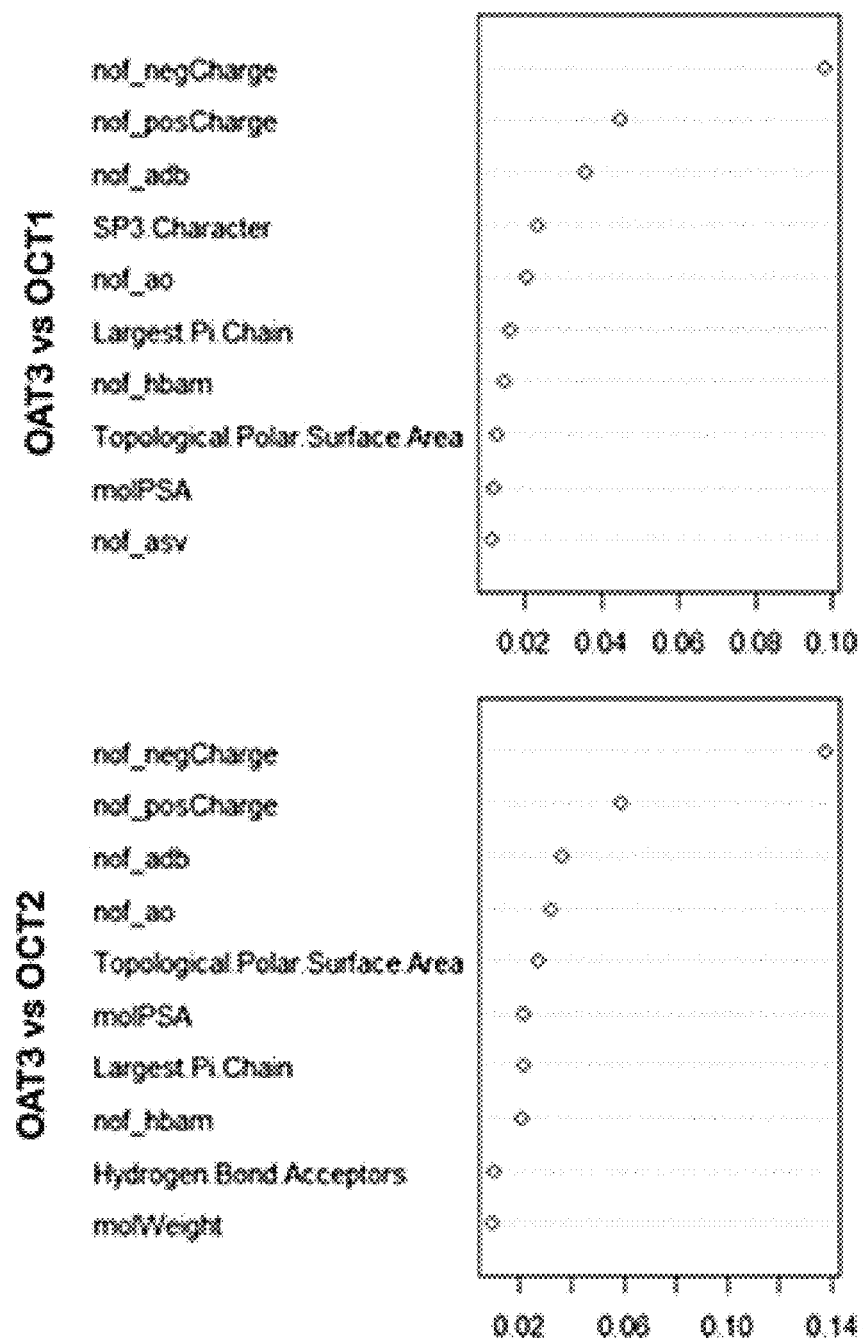
Figure 14:
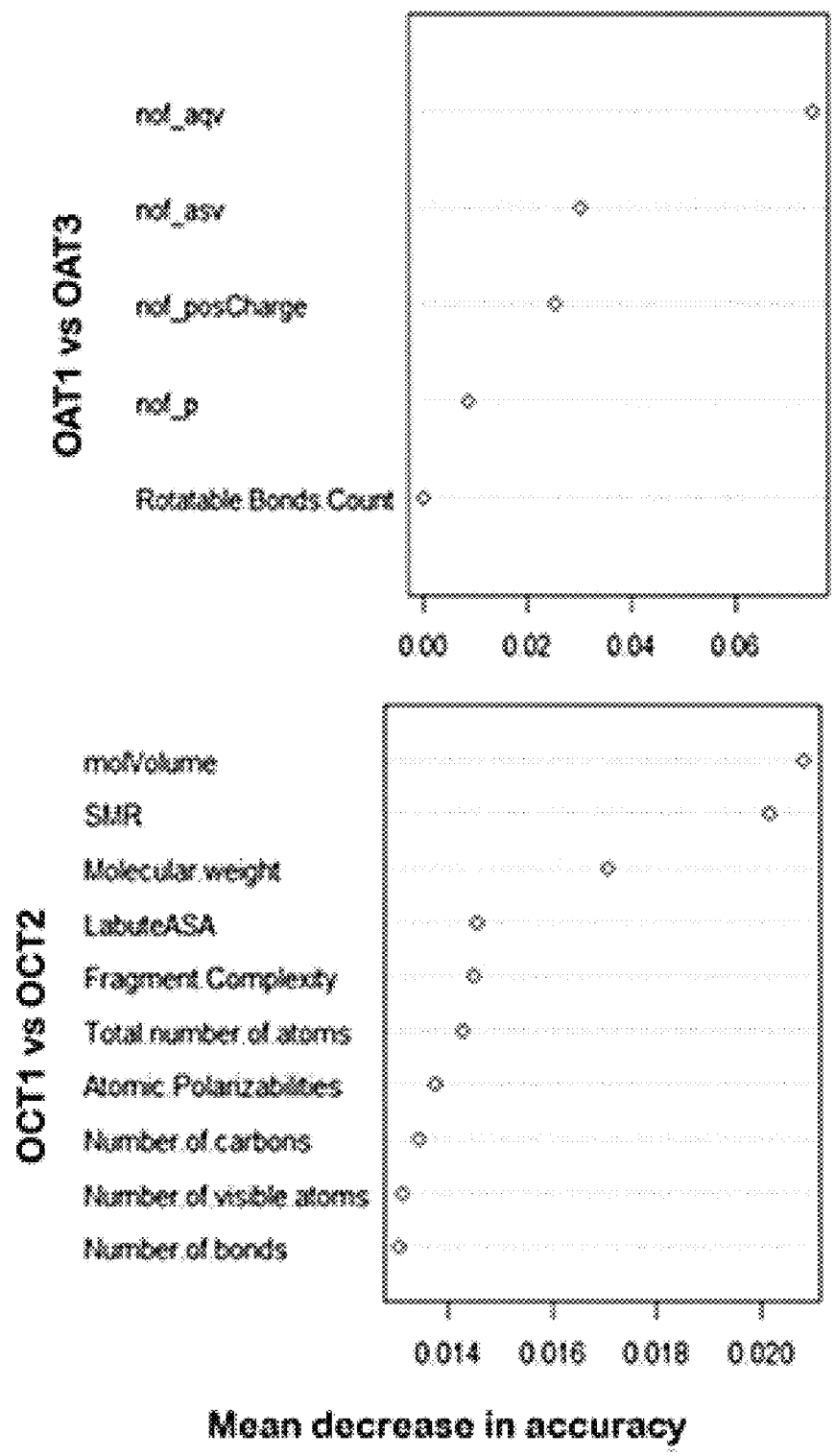
Figure 15A:
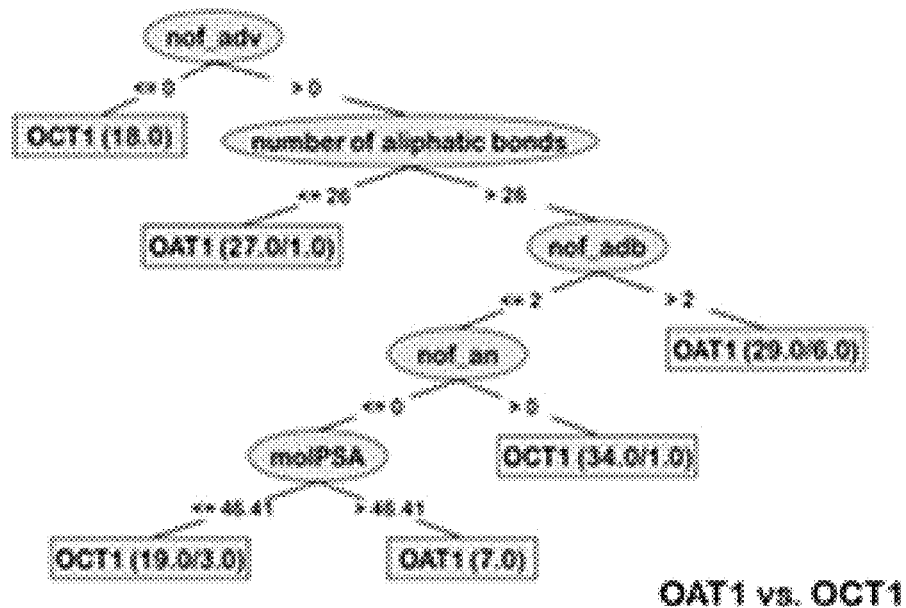
FIG. 15A-D shows decision trees excluding charge properties. The attributes of positive and negative charge were excluded in the building of the model so as to identify other important properties that potentially segregate OAT and OCT drugs. Again, it was found that some charge-associated attributes and the SP3 character were key determinants.
Figure 15B:
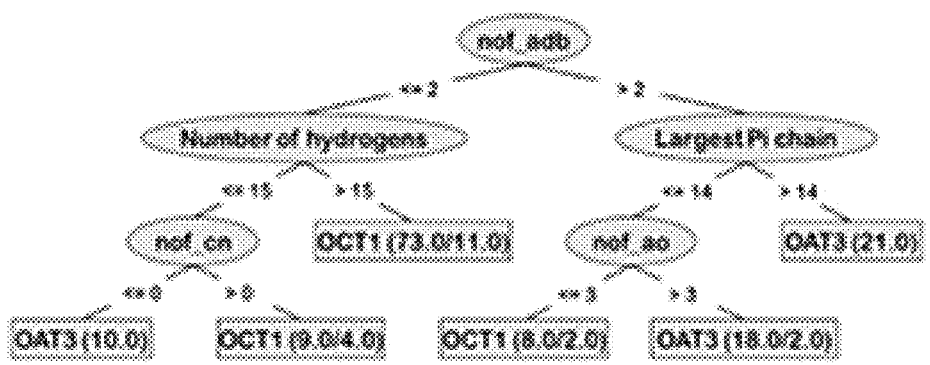
Figure 15C:
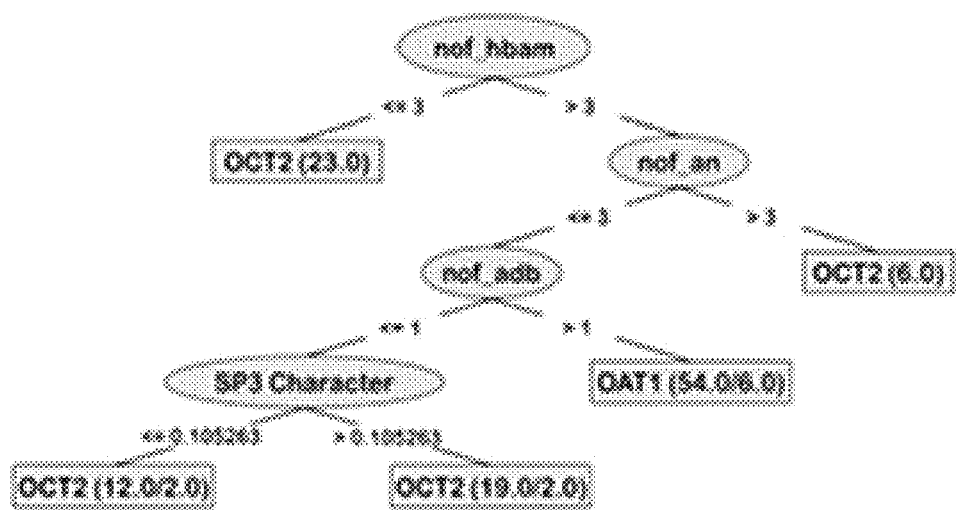
Figure 15D:
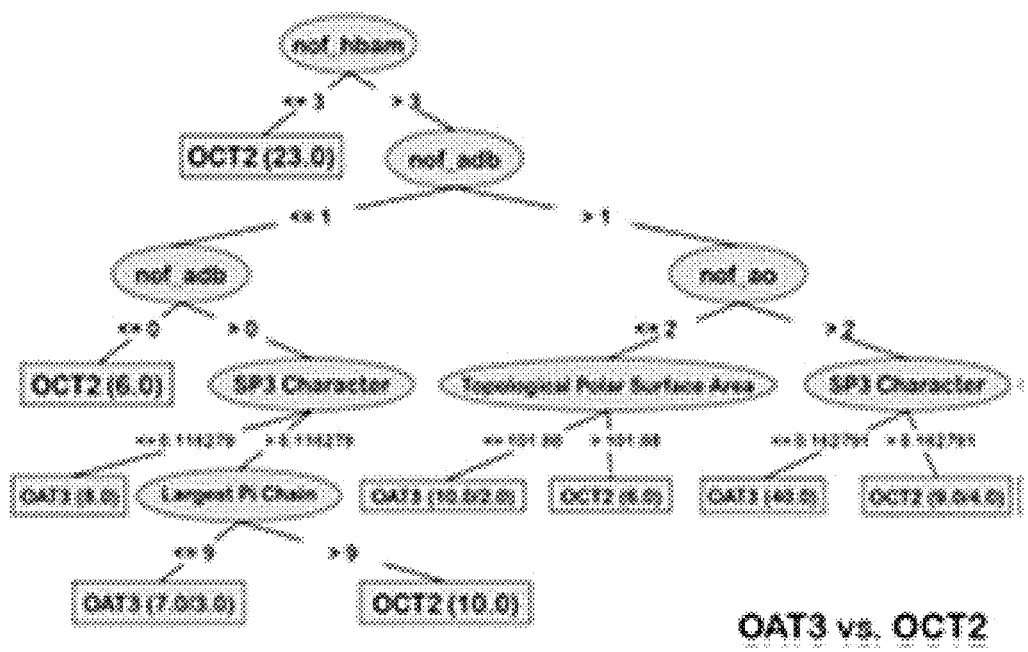
Figure 16A:
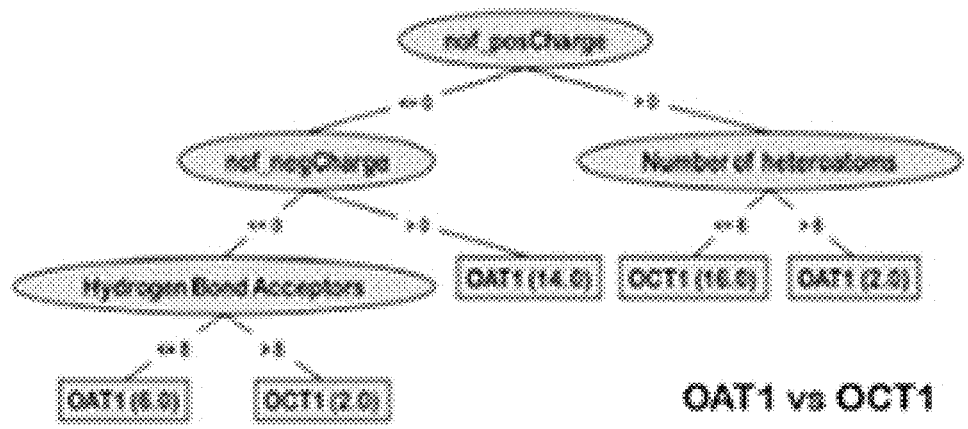
FIG. 16A-F shows the decision trees constructed with drugs that interact with the transporters at mid-affinity range (between 100 and 1000 mM). The trees show that, in the mid-affinity range, the main differences between OAT- and OCT-interacting drugs were still attributable to charges, but to a lesser degree than drugs in the high-affinity range.
Figure 16B:
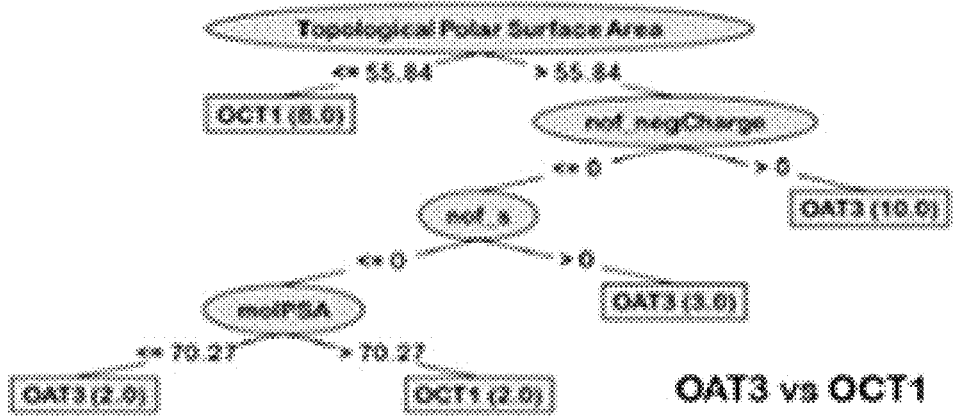
Figure 16C:
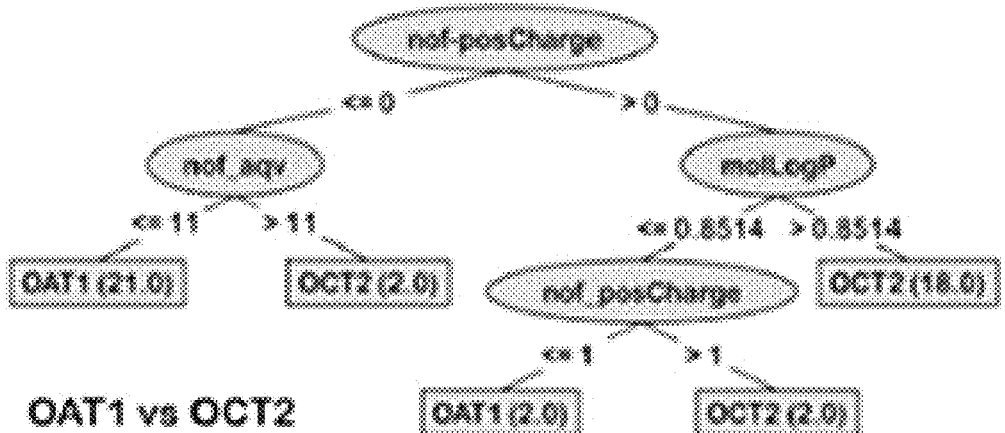
Figure 16D:
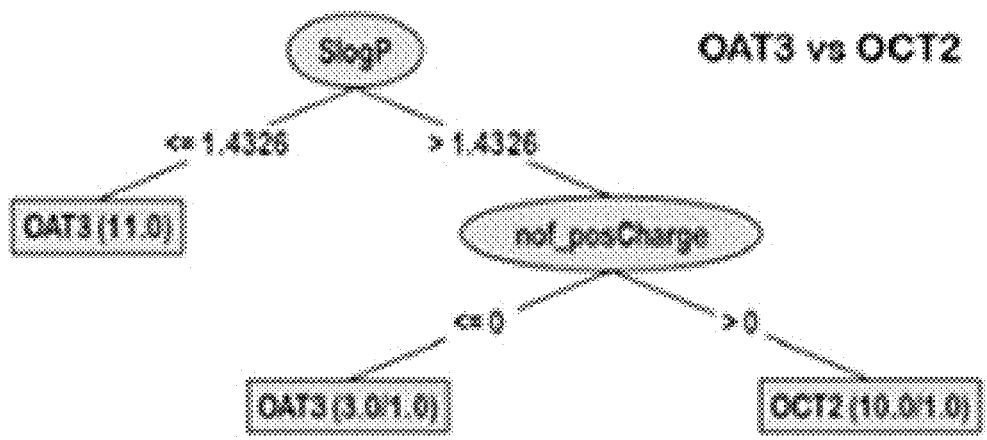
Figure 16E:
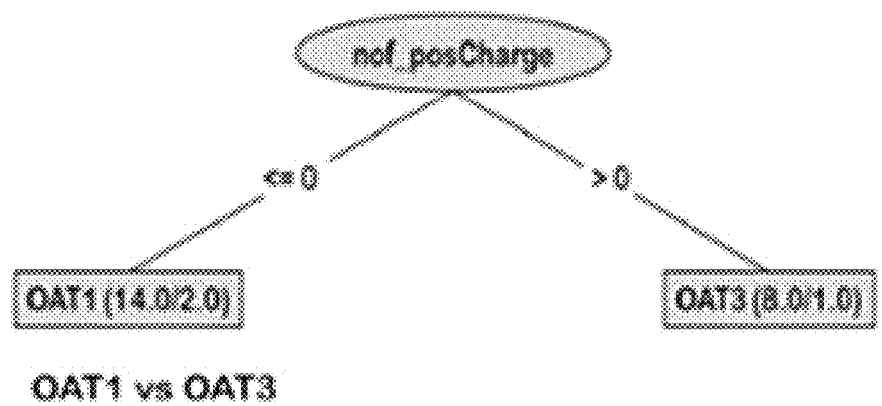
Figure 16F:
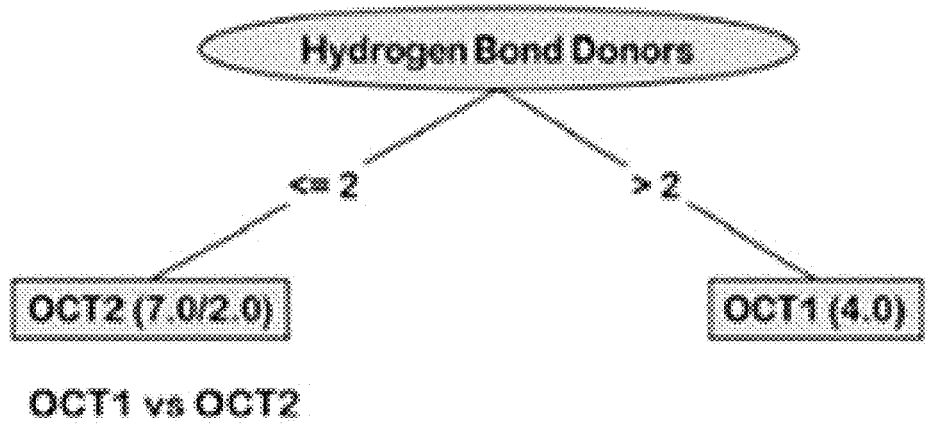

Random forest models were also used as an independent classification approach. In the variable importance plots derived from the random forest model for the pairwise OAT and OCT comparisons, the charge state information was also found to dominate in the ranking (FIG. 14). This supports the notion that the higher nodes in the decision tree are robustly important for classification across the bootstrap samples in the random forest. In addition, the variables found to be most important after the charge state were the number of acyclic double bonds (adb), acyclic oxygens (ao), followed by the "SP3 character." After five or six variables, the importance levels drop off and little is gained by considering additional variables. For the pairwise comparison between OATs, the results also confirm and justify the decision tree interpretation. However, for OCT1 versus OCT 2, the results are not aligned, which is not surprising given that the classification performance is poor (FIG. 14).

Exclusion of Charge Reveals Potential Role of Physicochemical Properties Other than Charge in Substrate Preference Differences.

The random forest models pointed to the potential role, in addition to charge, that other physicochemical features of the high-affinity drugs might play in separating OAT-interacting drugs from OCT interacting drugs. Therefore, decision trees were constructed that excluded the properties of positive and negative charge (FIG. 15). The resulting trees split on a variety of other properties; the number of acyclic double bonds ("adb"), number of acyclic oxygens ("ao"), number of acyclic nitrogens ("an"), and the "SP3 character" were dominant.

In the OAT1/OCT1 tree, the first attribute that split was "adv" (acyclic divalent nodes); drugs that had zero "adv" were classified as OCT1 drugs. The next attribute was "number of aliphatic bonds," and drugs with the greater number of aliphatic bonds were classified as OCT1 drugs. When we examined the three other OAT versus OCT trees, they followed trends similar to the OAT1/OCT1 tree; OCT ligands generally had a higher number of "an" than OAT ligands, and OAT ligands had higher numbers of "adb" and "ao" than did OCT ligands. Interestingly, statistics from the accuracy of these decision tree models (which excluded charge) were not as strong as ones including charge but were still reasonable (Table 5). In addition, the attributes "ao," "adb," and "SP3 character" were confirmed as important attributes in the t test statistical analysis (below and Table 7).

TABLE 7

| Pairwise Comparison | Number of Attributes, by P Value | | | Top Eight Attributes Ranked by P Values | | | |
| --- | --- | --- | --- | --- | --- | --- | --- |
| | <0.005 | <0.01 | <0.05 | | | | |
| OAT1 versus OCT1 | 27 | 29 | 37 | nof_posCharge (P = 5.95E−23) | nof_negCharge (P = 4.92E−13) | nof_adb (P = 2.4E−12) | nof_ao (P = 3.17E−09) |
| OAT3 versus OCT1 | 17 | 18 | 23 | nof_negCharge (P = 1.10E−16) | nof_posCharge (P = 2.44E−15) | nof_adb (P= 4.95E−13) | nof_ao (P = 3.07E−10) |
| OAT1 versus OCT2 | 16 | 21 | 28 | nof_posCharge (P = 1.45E−19) | nof_negCharge (P = 1.31E−13) | nof_adb (P = 1.52E−11) | nof_ao (P = 1.15E−10) |
| OAT3 versus OCT2 | 17 | 20 | 27 | nof_negCharge (P = 3.52E−17) | nof_posCharge (P = 8.12E−14) | nof_ao (P= 1.71E−11) | nof_adb (P = 3.24E−11) |
| OAT1 versus OAT3 | 1 | 2 | 18 | nof_aqv (P = 0.00257) | nof_posCharge (P = 0.00586) | nof_asv (P = 0.01339) | nof_asb (P = 0.01364 |
| OCT1 Versus OCT2 | 6 | 12 | 30 | nof_s (P = 0.00171) | molWeight (P = 0.00382) | LabuteASA (P = 0.00451) | Number of heavy atoms (P = 0.00495) |

TABLE 7-continued

| Pairwise Comparison | Top Eight Attributes Ranked by P Values | | | |
|---|---|---|---|---|
| OAT1 versus OCT1 | nof_hbam (P = 2.25E−08) | SP3 Character (P = 1.34E−07) | Number of hydrogens (P = 7.90E−07) | nof_asv (P = 1.11E−06) |
| OAT3 versus OCT1 | nof_hbam (P = 7.08E−09) | molPSA (P = 1.35E−06) | SP3 Character (P = 2.7E−06) | Topological polar surface area (P = 3.63E−06) |
| OAT1 versus OCT2 | nof_hbam (P = 1.08E−09) | SP3 Character (P = 4.59E−07) | molPSA (P = 8.03E−07) | nof_adv (P = 1.64E−06) |
| OAT3 versus OCT2 | nof_hbam (P = 1.27E−09) | Hydrogen Bond Acceptors (P = 1.03E−06) | molPSA (P = 1.32953E−06) | nof_adv (P = 1.66E−06) |
| OAT1 versus OAT3 | nof_rbc (P = 0.01432) | molVolume (P = 0.01828) | Fragment Complexity (P = 0.01924) | Number of hydrogens (P = 0.01960) |
| OCT1 Versus OCT2 | SMR (P = 0.00497) | nof_hac (P = 0.00514) | Vertex adjacency information magnitude (P = 0.00527) | nof_rings6 (P = 0.00545) |

Pairwise Comparison Between OAT1 and OAT3 Reveals Differences Between the Two OATs.

Figure 13A:
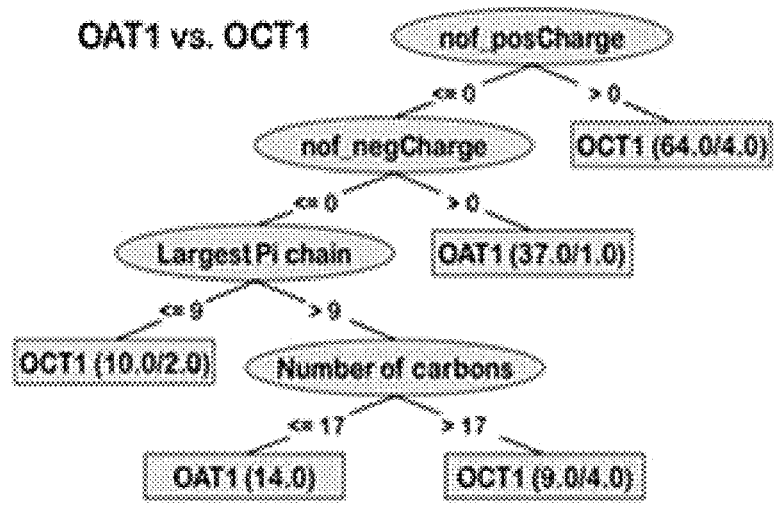
FIG. 13A-F shows various decision trees generated on the basis of those drugs interacting with the transporters with high-affinity (i.e., ≤100 µM). The decision trees show that the main difference between OATs and OCTs are attributable to charge and charge-associated properties. Besides charge, the three-dimensionality versus planarity of the drug, indicated by SP3 character, was found to be another important factor in separating OAT and OCT drugs. In addition, some differences were found between two OATs, specifically in number of aqv, p, and pos Charge (these attributes are further explained below).
Figure 13B:
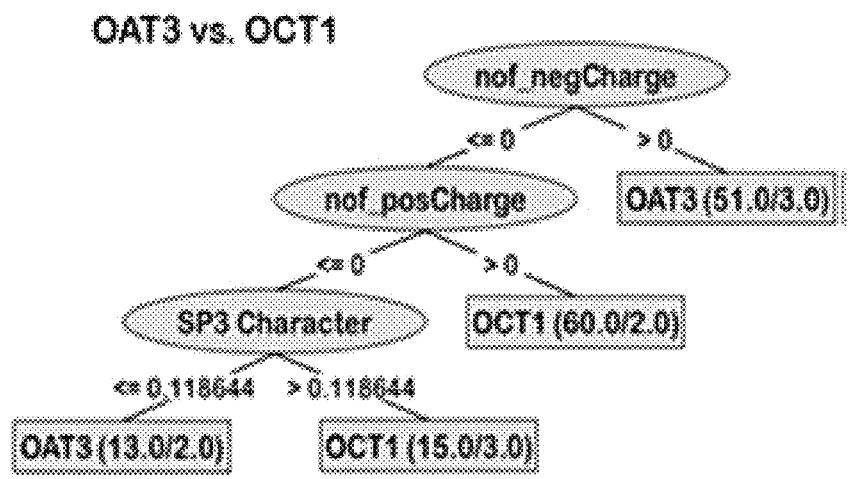
Figure 13C:
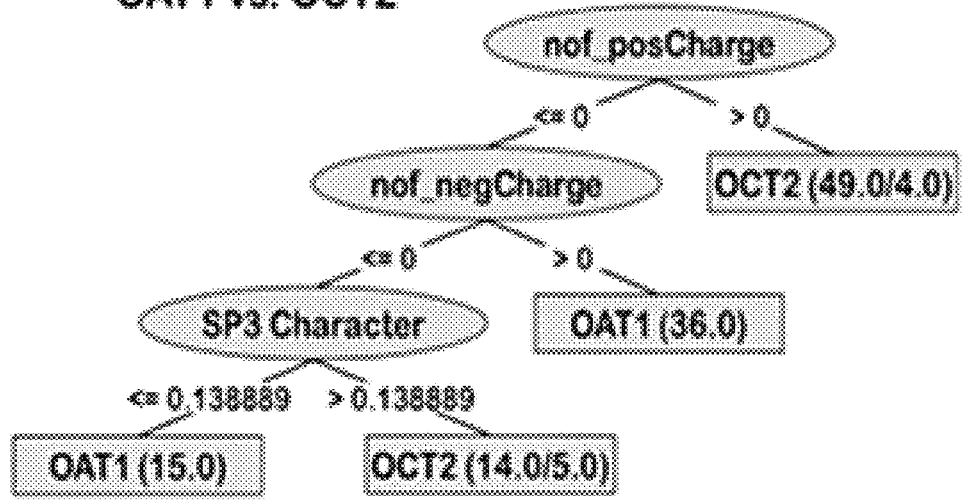
Figure 13D:
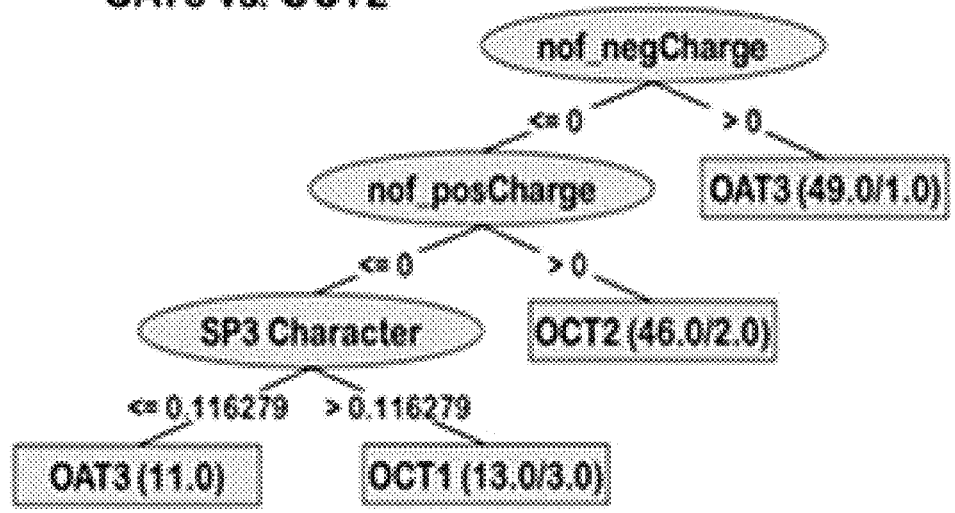
Figure 13E:
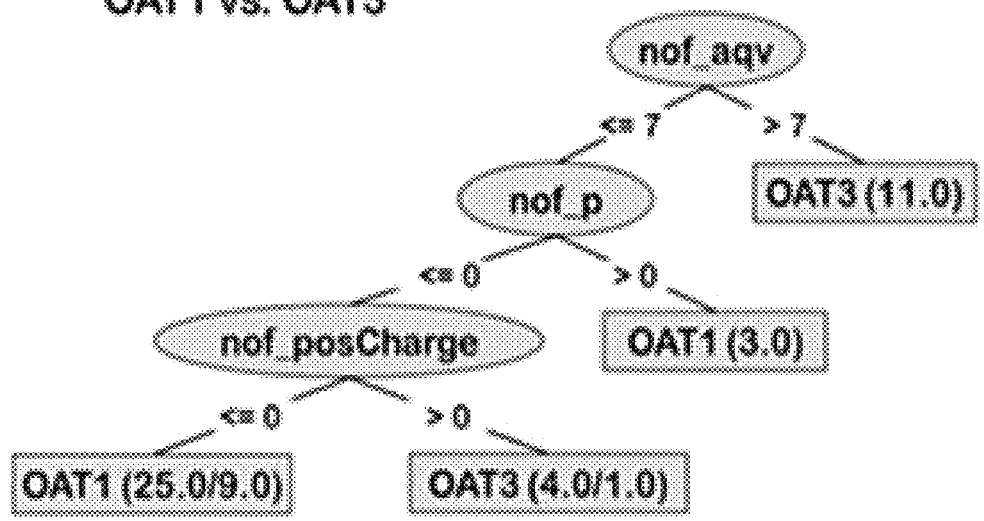
Figure 13F:
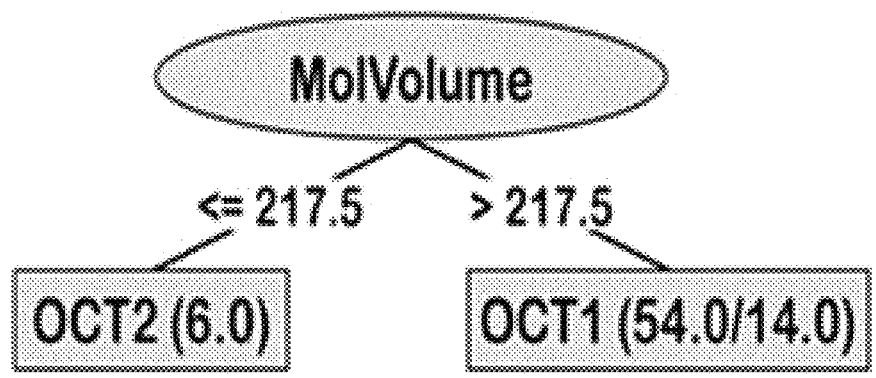

When OAT1 and OAT3 were compared (FIG. 13E), the first attribute separating OAT1 and OAT3 ligands was the number of acyclic tetravalent nodes ("aqv"). Drugs that have the greater number of acyclic tetravalent nodes tended to be classified as interacting with OAT3. The next attribute separating the OAT ligands was the number of phosphorous atoms ("p"). Drugs that had at least one or more phosphorus atoms tended to be classified as OAT1-interacting. A third attribute that emerged from these comparisons of OAT1 and OAT3 ligands was the number of positive charges; drugs with a positive charge were associated with an OAT3 classification (FIG. 13E). In contrast to the comparison of the two OATs, the model generated for comparison of the two OCTs had poor validation performance; it appears that OCT ligands are too similar to be distinguished by the approaches we used; hence, the results for that decision tree model will not be discussed further.

Statistical Analysis Confirmed the Machine-Learning Analyses.

When performing t test analyses on individual attributes for each pairwise transporter comparison, we identified a number of attributes as statistically different between ligands interacting with each pair of transporters. The attributes that had the lowest P values for each comparison are summarized in Table 7 and are consistent with the machine-learning analyses. The two properties that had the lowest P values were the "number of positive charge" and the "number of negative charge," corresponding to the results from the machine-learning analyses. After positive and negative charge, the next attributes that came out from the ranking were numbers of acyclic double bond ("adb"), acyclic oxygen ("ao"), hydrogen bond acceptor site ("hbam"), and SP3 character (Table 7). For the pairwise comparison of the two OATs, the two properties seen in the OAT1/OAT3 decision tree [i.e., the "number of acyclic tetravalent nodes" ("aqv") and "number of positive charges"] were also found to have the lowest P values in the ranking. Again, the results from both decision trees and random forest are consistent with the statistical analysis.

Explanation of Properties Found to be Relevant in Results.

As described above, on the basis of the results of machine-learning and statistical tests, it was shown that ligands of the OATs (either OAT1 or OAT3) generally had higher numbers of negative charge, acyclic double bonds, acyclic oxygen, and hydrogen bond acceptor sites than an OCT ligand (either OCT1 or OCT2). These properties tend to be associated with the anionic propensity. For example, most acyclic double bonds within the structures were in the forms of carbonyl (C5C), thial (S5C), sulfoxide (S5O), and the electronegative oxygen and sulfur within these double bonds are prominent hydrogen bond accepting sites. The "number of acyclic oxygen" is another property that expresses the anionic propensity, as the acyclic oxygen also serves as a potential hydrogen bond accepting site.

Importantly, in addition to having differences in properties associated with charges and ionization, ligands of OCTs and OATs are different in geometry-related properties, particularly with respect to the SP3 character value. SP3 character is defined as the number of SP3-hybridized carbons divided by the total number of atoms; it is one measure of the degree of three-dimensionality of a compound. If a drug has a higher SP3 character value, it is more three-dimensional; likewise, a lower SP3 character value is taken to imply that the drug is more planar (Lovering et al., 2009; Over et al., 2014). In machine-learning models and statistical analyses, drugs with a stronger affinity for the OCTs had a greater SP3 character value than those with a stronger affinity for the OATs, supporting the view that the "OCT-interacting drugs" are more three-dimensional than "OAT-interacting drugs." As measured by SP3 character, compared with most other drugs in the data set, amantadine, nandrolone, and atropine are three OCT drugs that have highly three-dimensional structures, each with a SP3 character value of 0.357, 0.326, and 0.227, respectively. On the other hand, OAT drugs have much lower values of SP3 character, with none of the OAT drugs having SP3 character values greater than 0.300.

Some differences are also observed among the ligands of the two OATs; OAT3 tended to interact with drugs that have more acyclic tetravalent nodes and more positive charges, whereas OAT1 tended to interact with those that have more phosphorus atoms. An acyclic tetravalent node usually is composed of a carbon-forming tetravalent bond with four elements. In the decision tree model, 11 drugs were classified as OAT3 drugs from this node; among them were verapamil, pravastatin, enalapril, and methotrexate, and along with the higher number of acyclic tetravalent nodes, these drugs have longer and more hydrophobic chains. The next attribute separating OAT1 and OAT3 ligands was the number of phosphorous atoms ("p"). Drugs that had at least one or more phosphorus atoms were classified as interacting with OAT1; the three drugs in this category were cidofovir, tenofovir, and adefovir. The chemical structures of these drugs showed that the phosphorus atoms were in phosphate groups. Since the phosphate groups contain several oxygen atoms binding with phosphorus—some of which were deprotonated at the normal pH range—the phosphate group is highly anionic. Thus, the number of phosphorus atoms was directly correlated with the anionic propensity. In summary, even though both OAT1 and OAT3 were found to have functional overlap, there were some differences between their ligands identified in our analyses. OAT3 preferred to interact with drugs with more positive charge and long hydrophobic chains, and OAT1 ligands tended to be more anionic than OAT3.

Analysis of Mid-Affinity Drugs Supports the Results of High-Affinity Drugs.

Figure 17A:
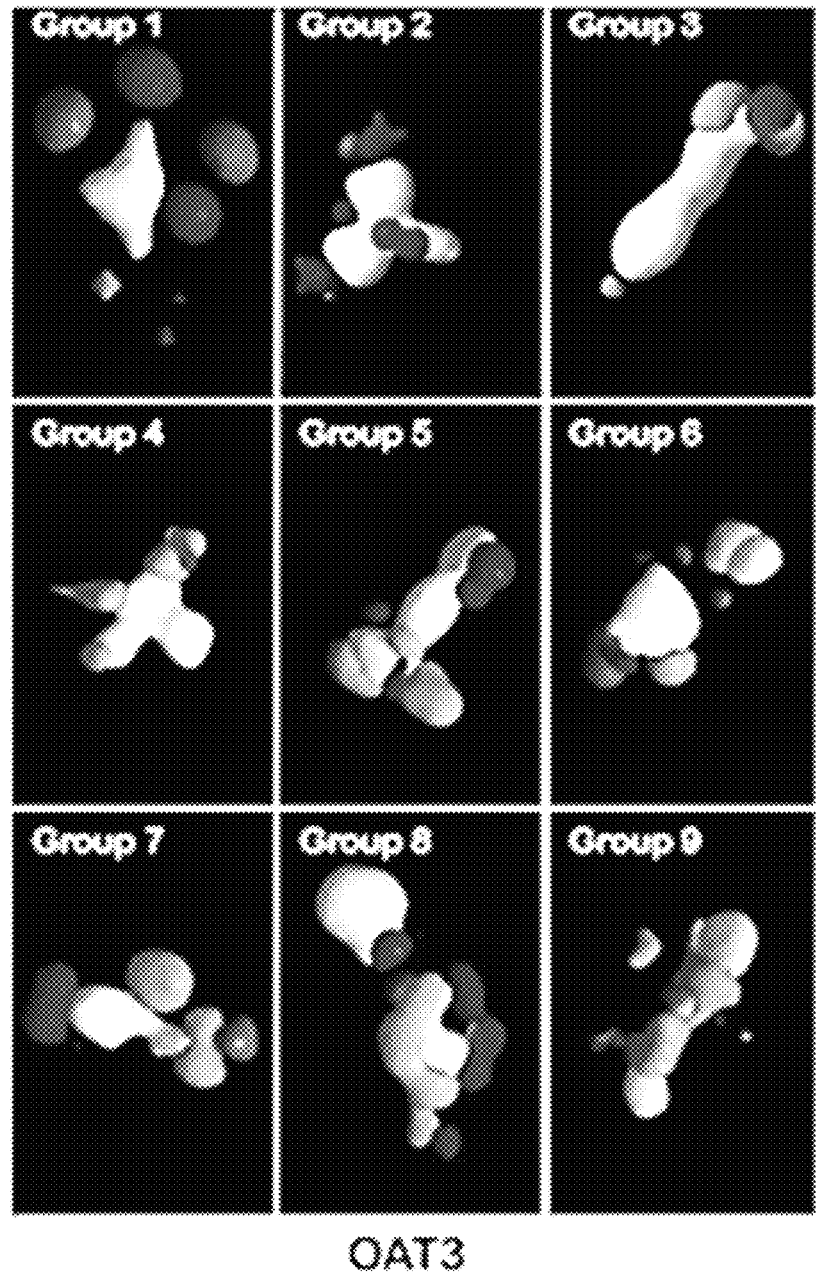
FIG. 17A-C shows pharmacophore models for OAT3, OCT1, and OCT2. Since the drugs interacting with each transporter were diverse in their three-dimensional structures, the drugs were clustered into groups on the basis of APF. The drugs within the same clustering groups were then aligned, and pharmacophore models for each group were created. In the pharmacophore models, different hades represent various APF properties: hydrogen bond donor; hydrogen bond acceptor; aromaticity; hydrophobicity; negative charges; positive charges. The OAT3 models and OCT1 models are found to be distinctive. With one notable exception, the OAT3 models for each group contained more characteristics of negative charges, electronegativity, and hydrogen bond acceptors, and vice versa for OCT1 models. However, the OAT3 model derived from group 9 was an exception as it contained several characteristics found largely in models from OCT groups.
Figure 17B:
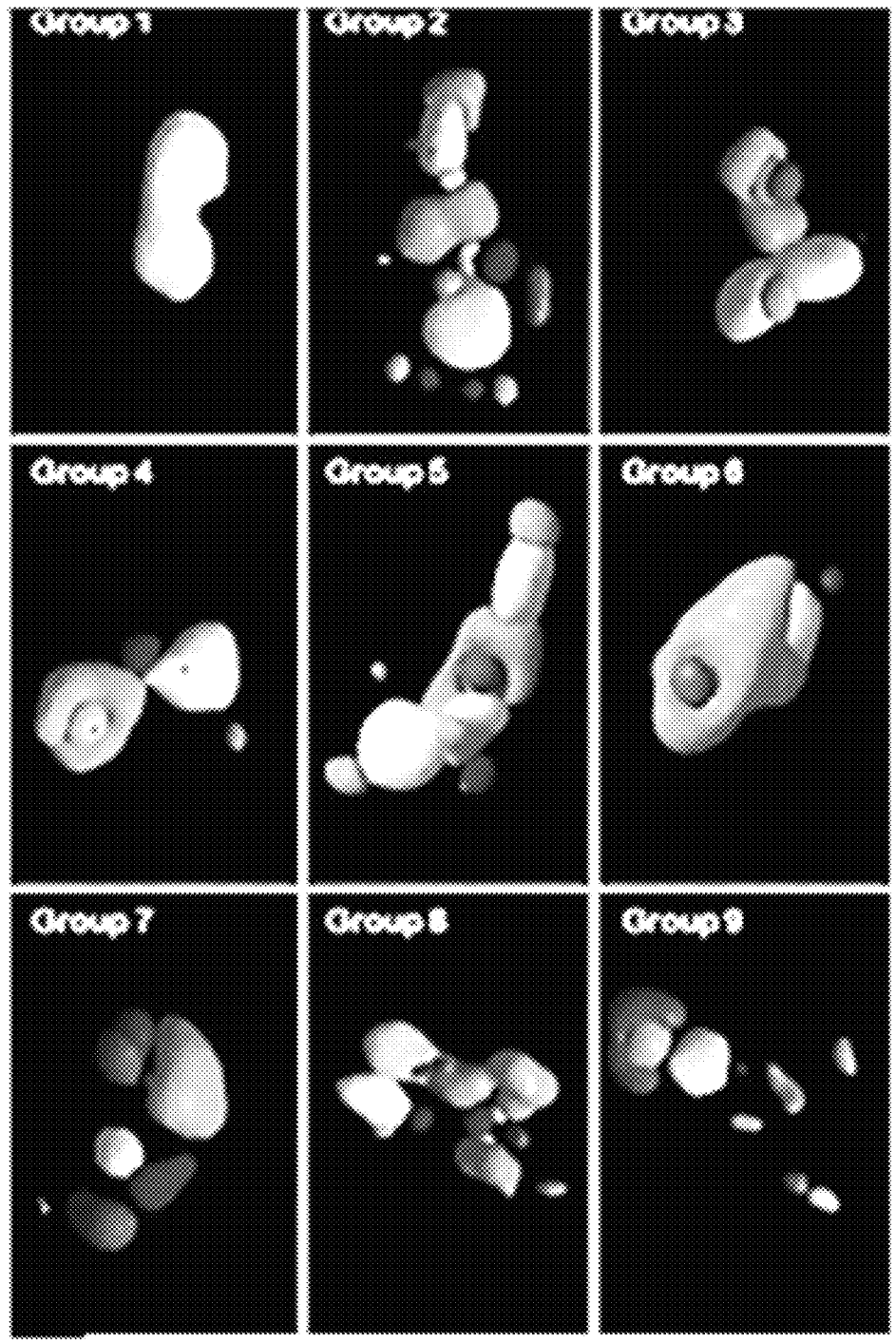
Figure 17C:
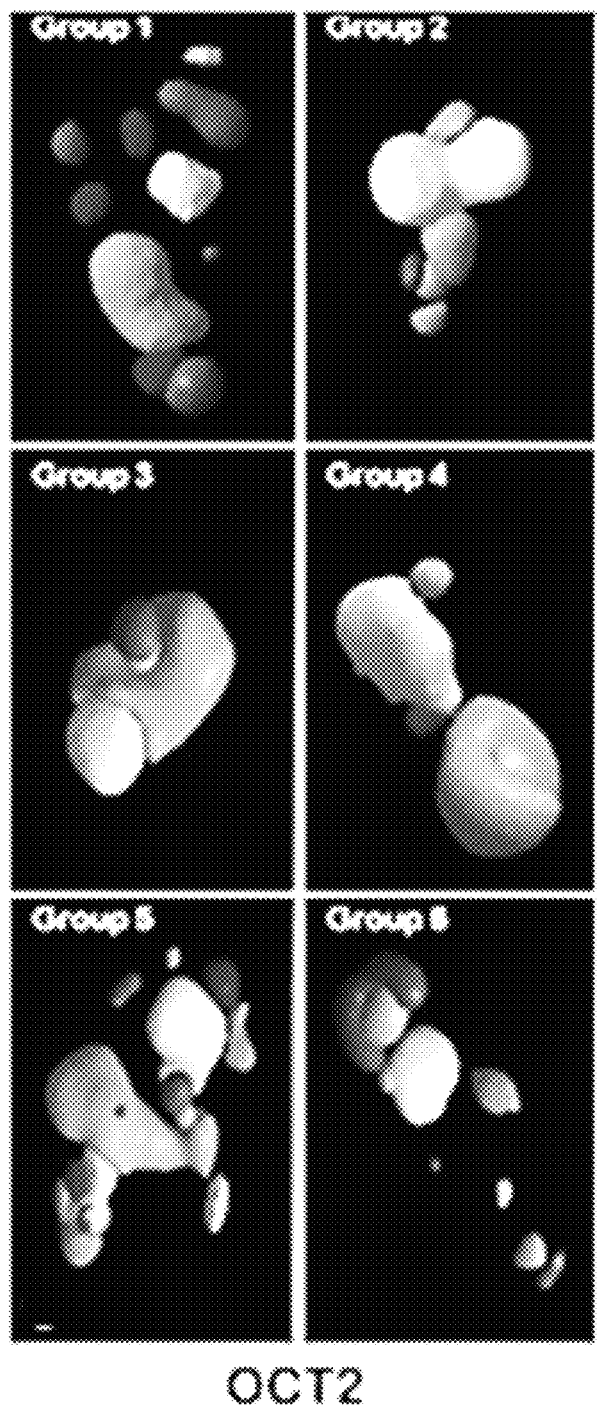

Well described OAT ligands verified in vivo in knockouts include many compounds with an affinity greater than 100 mM (Eraly et al., 2006; Vallon et al., 2008a; Wikoff et al., 2011; Wu et al., 2013). Thus, in addition to understanding three-dimensional space (FIG. 17). The models showed that OAT3 and OCTs interacted with drugs that had hydrophobic and aromatic centers. However, a slight difference in compound backbone appeared, as the hydrophobic chains for OCT1 and OCT2 models would sometimes enclose cationic spheres (seen in OCT1 pharmacophore models 3, 4, 5, and 6), which is not observed in most OAT3 models. Overall, models of OAT3-interacting ligands were more anionic, and models of OCT-interacting ligands were more cationic. This can also be seen from Table 8, which shows the quantitative measurements of the seven properties for individual models; as measured by the mean, the table shows that ligands of the OATs had higher "hydrogen bond acceptors" and higher "negative charges"; in contrast, ligands of the OCTs had higher "hydrogen bond donors" and higher "positive charges."

TABLE 8

Quantitative APF property measurements:

| Transporter | Pharma-cophore Model | Hydrogen Bond Donors | Hydrogen Bond Acceptors | Sp2 Hybridization | Lipophilic | Size (large) | Charge Positive | Charge Negative | Electro Positive | Electro Negative | Overall Space |
|---|---|---|---|---|---|---|---|---|---|---|---|
| OAT3 | 1 | 143.204 | 154.117 | 839.695 | 101.509 | 213.651 | 0 | 0 | 219.724 | −117.099 | 47124 |
| | 2 | 68.1087 | 484.381 | 1560.94 | 628.674 | 773.567 | 0 | −230.93 | 587.804 | −289.52 | 82173 |
| | 3 | 7.92777 | 175.642 | 1009.03 | 493.385 | 636.479 | 6.5641 | −193.954 | 529.816 | −102.394 | 80496 |
| | 4 | 88.2388 | 189.237 | 1441.67 | 925.382 | 1058.15 | 0 | −138.558 | 964.06 | −140.411 | 98000 |
| | 5 | 35.8698 | 387.069 | 1795.93 | 923.052 | 1148.9 | 0 | −197.94 | 997.226 | −151.581 | 120744 |
| | 6 | 220.122 | 169.155 | 894.646 | 580.978 | 656.921 | 0 | −38.4882 | 588.515 | −325.512 | 68894 |
| | 7 | 197.147 | 244.087 | 881.089 | 588.426 | 752.08 | 57.7324 | −173.197 | 773.25 | −176.682 | 66934 |
| | 8 | 123.888 | 427.116 | 1445.62 | 664.117 | 934.116 | 0 | −181.445 | 686.311 | −246.443 | 116550 |
| | >9$^a$ | 66.121 | 252.657 | 850.408 | 1164.04 | 1358.78 | 73.3308 | −175.956 | 1331.36 | −99.7383 | 149940 |
| OCT1 | 1 | 48.1776 | 31.481 | 1056.59 | 570.64 | 704.827 | 102.635 | 0 | 823.36 | −23.6894 | 115248 |
| | 2 | 90.1057 | 195.495 | 1020.17 | 716.752 | 937.243 | 46.1859 | 0 | 829.391 | −75.0204 | 92752 |
| | 3 | 69.2848 | 32.1592 | 845.243 | 830.424 | 951.403 | 110.846 | 0 | 997.719 | −20.1164 | 134160 |
| | 4 | 74.3945 | 95.9579 | 670.303 | 748.842 | 882.211 | 115.463 | 0 | 979.179 | −55.4399 | 93240 |
| | >5 | 80.1732 | 150.189 | 951.337 | 1241.55 | 1355.43 | 115.463 | 0 | 1323.47 | −66.1869 | 110124 |
| | >6 | 77.3553 | 68.1684 | 211.241 | 806.307 | 962.966 | 69.2789 | 0 | 1106.73 | −21.3618 | 80360 |
| | 7 | 216.391 | 229.452 | 556.192 | 339.69 | 456.407 | 17.6656 | −56.1539 | 503.882 | −61.367 | 62700 |
| | 8 | 193.59 | 217.192 | 1639.75 | 1511.09 | 1730.88 | 46.1859 | 0 | 1827.44 | −80.0704 | 164683 |
| | 9 | 554.411 | 58.0202 | 1109.79 | 377.711 | 472.479 | 346.304 | 0 | 887.07 | −48.0251 | 105408 |
| OCT2 | 1 | 211.184 | 222.252 | 622.403 | 345.852 | 501.321 | 23.0927 | −69.2787 | 498.707 | −75.3364 | 115248 |
| | 2 | 68.8116 | 29.6212 | 918.07 | 778.429 | 890.004 | 98.145 | 0 | 946.223 | −7.10932 | 92752 |
| | 3 | 101.393 | 47.913 | 287.96 | 825.327 | 881.816 | 79.382 | 0 | 992.614 | −23.1909 | 134100 |
| | 4 | 82.6908 | 86.1924 | 667.67 | 738.494 | 867.966 | 128.201 | 0 | 977.612 | −49.6171 | 93240 |
| | 5 | 133.952 | 214.602 | 1024.3 | 1156.25 | 1402.03 | 76.9765 | 0 | 1347.41 | −64.4699 | 110134 |
| | 6 | 502 | 39.793 | 1078.9 | 352.868 | 453.107 | 269.418 | 0 | 826.522 | −24.6827 | 80360 |

$^a$OAT3 pharmacore model 9 (arrowhead) was found to have higher value of positive charge and electropositive charge than the rest of OAT3 pharmacophore models. The APF property values of this model were also found to be comparable with several OCT1 models, such as OCT1 models 5 and 6 (arrowheads).

the molecular interactions between transporters and drugs that bind with high affinity (≤100 μM), experiments were performed to study how OAT1, OAT3, OCT1, and OCT2 interact with drugs in the mid-affinity range (100-1000 μM). The decision trees constructed with mid-affinity drugs (FIG. 16) demonstrate that major factors involved in classifying a drug as an OAT or an OCT substrate were the result of charge, as in the high-affinity group. But the separation was less impressive than for the high-affinity (<100 μM) drugs. The decision tree comparing OAT1 and OAT3 in the mid-affinity range had only one node, which split on positive charge (FIG. 16). Drugs with a positive charge generally classified as OAT3-interacting.

Three-Dimensional Pharmacophore Models Showed Structural Similarities Corresponding to the Overlap in Functions for OATs and for OCTs.

Since it was found that OAT3 ligands also possessed some cationic characteristics, on the basis of the machine-learning analyses, pharmacophore models for OAT3-, OCT1-, and OCT2-interacting drugs were built to compare the functional similarities/differences between the OAT and the OCTs in The Pharmacophore Models Revealed Structural Similarities Between Ligands of OAT3 and OCT1.

Even though the majority of pharmacophore models for ligands of OAT3 had similar features, there was one clear exception, the pharmacophore model formed on the basis of group 9 for OAT3 (FIG. 17). Unlike other OAT ligand models, this model contained a hydrophobic chain that tended to enclose a sphere enriched with hydrogen bond donors and positive charges, which was a pattern shared among many OCT1 and OCT2 ligand models. Thus, this model (OAT3 pharmacophore model 9) was found to be very OCT-like, and the quantitative APF measurement of this model was found to have greater values of "positive charges" and "electropositive charges."

Interestingly, the list of drugs used to construct this model from group 9 for OAT3 was found to be highly similar to the list of drugs that was independently separated on the basis of the first attribute or node in the OAT1/OAT3 decision tree (FIG. 13). Out of the nine drugs used to construct the pharmacophore model, six of them contained more than seven acyclic tetravalent nodes and were classified as "OAT3" drugs in the decision tree. This is important since it demonstrates that the results from the decision trees and the pharmacophore models identified the same differences found between ligands of OAT1 and OAT3, and the differences were attributable to the apparent capability of OAT3 to interact with OCT-like substrates.

Experimental Validation of in Silico Screening Results Identified New Cationic Drugs that Preferentially Interact with OAT3 but not OAT1.

Figure 18:
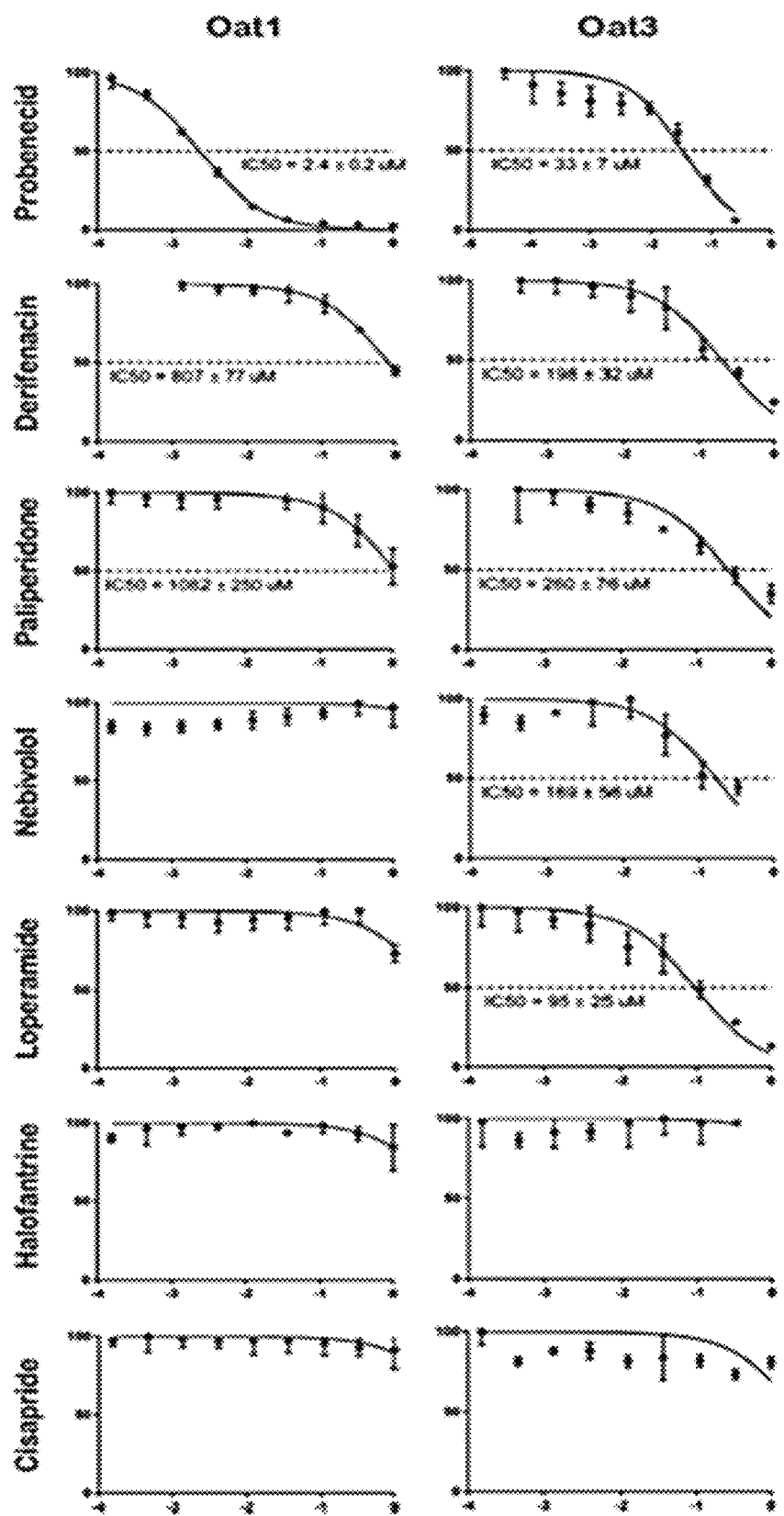
FIG. 18 shows uptake inhibition assay on the basis of the virtual screening of the OAT3 pharmacophore model from group 9 (i.e., cationic pharmacophore) against the DrugBank database. For OAT1 inhibition assay, 10 mM 6-carboxyfluorescein was used as fluorescent tracer, and for OAT3 assay, 20 mM 5-carboxyfluorescein was used.

The finding that OAT3 prefers more cationic substrates than does OAT1 was thus consistent in decision tree and random forest analyses, and there was one (cationic) OAT3 pharmacophore model that was strikingly similar to OCT pharmacophore models. Thus, with the idea of trying to validate this experimentally, the OAT3 cationic model was used for virtual screening in silico. Using the pharmacophore model on the basis of group 9 of the OAT3 substrates, a virtual screen of the Drug Bank database identified potential new OAT3 cationic ligands. Six top hits were selected for further wet laboratory validation. These hits were then tested for their ability to interact selectively with OAT3 using wet laboratory transport assays in OAT1-expressing or OAT3-expressing cells. Four of the ligands were found to interact with OAT3, with strong inhibition of tracer uptake. In marked contrast, when these six cationic drugs were tested in the OAT1 uptake assay, it was found that only two of them inhibited OAT1 function, and, importantly, with a much lower affinity (FIG. 18). The preference of these compounds for interaction with OAT3, but not OAT1, not only supports the validity of the pharmacophore model (model 9) but it is consistent with the machine-learning analysis indicating the capability of OAT3 to interact with cationic drugs. The measured $IC_{50}$ values of tested compounds against OAT1 and OAT3 are summarized in Table 9.

TABLE 9

IC50 values of cationic drugs tested for interaction with OAT1 and OAT3:

| | $IC_{50}$ (μM) | |
|---|---|---|
| Drug Name | OAT1 | OAT3 |
| Probenecid[a] | 2.4 | 33 |
| Darifenacin | 807 | 198 |
| Paliperidone | 1082 | 260 |
| Loperamide | No significant inhibition | 95 |
| Nebivolol | No significant inhibition | 169 |
| Halofantrine | No inhibition | No inhibition |
| Cisapride | No inhibition | No ihhibition |

The data for probenecid uptake inhibition is shown as control.

Example 3

Animals—

Animals were handled in accordance with the Institutional Guidelines on the Use of Live Animals for Research; all experiments involving the use of animals were also conducted in accordance with the Institutional Guidelines on the Use of Live Animals for Research. Adult (n=3) wildtype, Oat3-deficient male mice received a single, daily intraperitoneal (i.p.) injection of either 200 mg/kg water-soluble probenecid (Invitrogen, Carlsbad, Calif.) [0.02 mg/μL in PBS (10 μL/g of body weight)] or PBS (sham-treated control) for three days. The animals were housed separately under a 12-h light-dark cycle and were provided access to food (standard diet) and water ad libitum. On day three, two hours before samples were taken, the mice were given a final i.p. injection of either probenecid or PBS. Two hours after this last treatment, blood was collected and plasma was isolated and stored at −80° C. until analysis was carried out.

Metabolomic Analysis—

Plasma and spontaneous urine samples (at the time of blood collection) from adult male and female wild-type (WT) control and Oat3-deficient mice (n=3) were obtained and individual, unpooled samples were stored at −80° C. until utilized. All samples were shipped together on dry-ice to Metabolon (Durham, N.C.) for preparation and metabolomic profiling analysis {Evans, 2009 #8083; Ohta, 2009 #8084}. Briefly, samples were prepared using the automated MicroLab STAR® system (Hamilton, Reno, Nev.) and subjected to ultrahigh performance liquid chromatography-tandem mass spectroscopy (UPLC-MS/MS) utilizing an ACQUITY ultra-performance liquid chromatography (UPLC) (Waters, Milford, Mass.) and a Q-Exactive high resolution/accurate mass spectrometer interfaced with a heated electrospray ionization (HESI-II) source and Orbitrap mass analyzer operated at 35,000 mass resolution (Thermo Scientific, Waltham, Mass.).

Compound Identification, Quantification, and Data Curation and Statistics—

Metabolites with missing intensity scores, indicating low levels of the metabolite in the sample, were imputed with the minimum value for the study following rescaling of the biochemicals to set the median equal to 1. Raw data was extracted, peak-identified and QC processed using Metabolon's hardware and software. Metabolites were identified by automated comparison of the ion features in the experimental samples to a reference library of chemical standard entries that included retention time, molecular weight (m/z), preferred adducts, and in-source fragments as well as associated MS spectra and curated by visual inspection for quality control using software developed at Metabolon {Evans, 2009 #8083; Ohta, 2009 #8084. Peaks were quantified using area-under-the-curve. Principal component analysis was used to detect outlying samples. Partial least squares discriminant analysis was used for assessment of separatability of the samples. Two-way ANOVA testing was used to calculate the p-values and an estimate of the false discovery rate (q-value) was calculated to take into account the multiple comparisons that occur in metabolomic studies. A metabolite was considered to be statistically different when p<0.05 and q<0.10. 150 of the most significant metabolites were included in a heat map using metabolite-level normalized data.

Statistical Analysis of Chemicophysical Properties of Metabolites—

T-tests were performed on the chemicophysical properties to determine if the differences in the mean values for each were statistically significant between two groups of metabolites and these chemicophysical properties were ranked according to their p-values.

To characterize the differential plasma metabolite profiles of Oat3KO mice compared to wild type controls, metabolomics profiling was performed using a Waters ACQUITY ultra-performance liquid chromatography (UPLC) and high resolution/accurate mass spectrometer. A total of 611 compounds (biochemicals) of known identity in the plasma were identified and detected across both groups. Following log transformation (base 10) and imputation of any missing values with the minimum observed value, ANOVA contrasts were used to identify biochemicals differing significantly between the Oat3KO and wildtype animals. An estimate of the false discovery rate (q-value; q<0.10 is an indication of high confidence in a result) was also calculated. In the plasma of Oat3KO mice, a total of 137 biochemicals (~22% of all the metabolites detected) were found to be significantly altered with p≤0.05 and a q≤0.1. Of these biochemicals, 50 were significantly increased and 87 metabolites were significantly decreased compared to the wild type controls ($p \leq 0.05$; $q \leq 0.1$). In addition, 60 biochemicals exhibited trends toward significant difference between the two groups ($0.05 < p < 0.10$).

While the application of principal component analysis (PCA) to determine separation of individual samples as a function of the plasma metabolome revealed some overlap between Oat3KO and wildtype mice, partial least squares discriminant analysis (PLS-DA), which can be used to maximize the separation among sample groups and target putative biomarkers for metabolomics studies (if PCA is not successful in showing the subtle differences) revealed a clear separation of knockout and wildtype groups based on their metabolite profile (N=3 per group). These metabolite alterations were further discriminated in a Z-score plot by plotting the intensities in the Oat3KO samples relative to their distribution in the wild-type control—in this type of plot, each dot represents 1 observation of 1 metabolite which were organized by major metabolic pathway. The magnitude of the intensity difference represents the number of standard deviations above (positive value) or below (negative value) the average value of the control group observation.

Using random forest (RF) analysis, the relative contribution of each variable was determined using the variable importance in projection (VIP) score, and the 30 most important metabolites for the classification scheme were identified. As described above, deletion of Oat3 reduced the clearance and distribution of numerous endogenous metabolites belonging to several different biochemical pathways. To understand the functional role of these metabolite alterations in the plasma of Oat3KO mice, a pathway set enrichment analysis was performed.

Among the most highly affected biochemical pathways were those with metabolites comprising the xenobiotic, amino acid and lipid superpathways.

Altered Xenobiotic Metabolism in Oat3KO Mice.

Of the 611 biochemicals detectable in this metabolomics analysis, 55 of them (~9%) are in the xenobiotic superpathway. Of these 55 biochemicals, 15 of them (~27%) were significantly altered in the plasma of the Oat3KO of which 14 (93.3%) were found to accumulate in the plasma of the Oat3KO mouse and included the sub-pathways involved in the metabolism of drugs, chemicals, benzoate and food components. The biochemical displaying the greatest level of accumulation was equol glucuronide, which was increased more than 42-fold in the Oat3KO (FIG. 3). Equol, a metabolite of the soy isoflavone, daidzein, is produced by the gut microbiome and metabolized to equol glucuronide by UDP-glucuronosyltransferases (UGTs)—phase II drug metabolizing enzymes in the liver. In most species, including humans, circulating equol metabolites are generally present as glucuronidated conjugates, although monosulfated forms can also be identified. Interestingly, equol sulfate was also increased more than 7-fold in the Oat3KO. In addition to equol, other biochemicals, including those belonging to metabolic pathways involved in the metabolism of benzoate, were also significantly increased in the plasma of the Oat3KO. Benzoate, a simple carboxylic acid, is produced in the gut from the digestion of dietary aromatic compounds (e.g., polyphenols, purines, and aromatic organic acids and amino acids). Thus, these benzoate metabolism-associated biochemicals are also derived from the gut microbiome.

Altered Amino Acid Pathways in Oat3KO Mice.

In addition to the xenobiotic super pathway, deletion of Oat3 also resulted in changes in the plasma levels for a number of metabolites belonging to several different pathways involved in the metabolism of amino acids. For example, 168 out of the 611 biochemicals (~27.5%) are found in the amino acid superpathway. Of these 168 biochemicals, 30 (~18%) were significantly altered in the plasma of the Oat3KO. Among those metabolites with the highest levels of plasma accumulation in the Oat3KO were biochemicals comprising the metabolism of phenylalanine and tyrosine pathway, as well as those comprising the tryptophan metabolism pathway.

For example, 6 (24%) of the biochemicals found in the metabolism of phenylalanine and tyrosine pathway were significantly increased in the Oat3KO, including gentisate, phenyllactate (PLA), p-cresol sulfate, p-cresol-glucuronide, phenol sulfate and 3-(3-hydroxyphenyl)propionate sulfate. Phenylalanine is an essential amino acid and the precursor of tyrosine and both of these amino acids share a common pathway of degradation which occurs in liver.

Tryptophan is also an essential amino acid which is absorbed from the gut and entered the circulation via transporters expressed on the enterocytes. Approximately 95% of ingested tryptophan will be metabolized in the liver via the kynurenine pathway. Another 1-2% of it will be converted to serotonin, a neurotransmitter produced mainly by the enterochromaffin cells of the gut, as well as by the pineal gland. A small fraction of ingested tryptophan is excreted unchanged in urine, while ~5% of ingested tryptophan will undergo degradation by the gut microbiome yielding indole, indican, and indole acid derivatives. Metabolites from these various tryptophan metabolic pathways accumulate in the plasma of the Oat3KO, including N-acetylkynurenine, serotonin, indoleacetate, indolelactate, 3-indoxyl sulfate, indole-3-carboxylic acid, and N-acetyltryptophan. Taken together, the data would appear to indicate that a number of metabolites comprising both the tryptophan metabolism pathway as well as the phenylalanine and tyrosine metabolism pathway are subsequently excreted by the kidney, providing another link to the gut-liver-kidney axis.

Altered Lipid Metabolism in Oat3ko Mice: Bile Acid Metabolism.

The majority of altered lipid metabolites were actually up in the plasma of wild-type mice compared to Oat3KOs, especially those lipids belonging to the phospholipid and sphingolipid metabolic pathways. Phospholipids, sphingolipids and lysolipids are the principal components of lipid bilayers in cell membranes and these findings may reflect reductions in cell membrane remodeling in the Oat3KO compared to the wildtype. Nevertheless, some lipid metabolites were found to accumulate in the plasma of Oat3KO mice, including components of primary and secondary bile metabolism. For example, cholate, a primary bile acid metabolite, was increased almost 160-fold in the plasma of the Oat3KO, while another primary bile acid metabolite, beta-muricholate was increased over 24-fold. Interestingly, several other primary bile acids, including taurocholate, glycocholate, chenodeoxycholate, tauro-beta-muricholate, and taurochenodeoxycholate were also increased (almost 30-fold in the case of taurochenodeoxycholate), although the increases did not reach statistical significance. In addition, a number of secondary bile acid metabolites were also significantly increased, including 7-ketodeoxycholate, deoxycholate, and ursodeoxycholate (again several other secondary bile acid metabolites were increased over ten-fold, including tauroursodeoxycholate, taurodeoxycholate, taurohyodeoxycholic acid—although statistical significance was not achieved). Nevertheless, the data clearly indicates dramatic effects on primary and secondary bile acid metabolism in the Oat3KO.

Fatty acid metabolites were also altered in the Oat3KO, in this case, both monohydroxy and dicarboxylate forms, including sebacate (decanedioate), tetradecanedioate, 3-hydroxyhexanoate, and 2-hydroxydecanoate.

Characterization of OAT3 Interacting Metabolites.

Statistical analysis was performed on the physicochemical descriptors of ~250 drugs known to interact with one or more SLC22 "drug" transporter, including OAT1 and OAT3 in order to investigate the ligand/functional differences between these transporters. It was found that, although some differences were found (e.g., OAT3 drug ligands appear to have a more positive charge and long hydrophobic chains), for the most part the drug ligands for OAT1 and OAT3 were similar. In order to investigate if this is also the case with the metabolite ligands, a similar comparison was performed.

To further investigate the metabolites, an extensive list of endogenous metabolites was compiled from both in vitro data, showing the ability to interact with OAT1 or OAT3 (Km and Ki data), and in vivo metabolomics data from this and other metabolomics analyses of the Oat1KO and the Oat3KO. The physicochemical properties of the various metabolites were calculated using ICM, a commercially available computational chemistry software (Molsoft, San Diego, Calif.), and PubChem, including complexity, molecular weight, molecular volume, Log P, Log S, polar surface area, atom counts, bond counts, polarity counts, ring counts, topology counts and others. T-test analyses were performed on the individual attributes pairwise comparisons of OAT1 and OAT3. A number of attributes were identified as statistically different between metabolites interacting with each transporter.

The list of ~70 OAT3 metabolites was then clustered based on their chemical structures. The clusterization resulted in the generation of 7 distinct clusters of metabolites with unique chemical structures. These clusters included sulfated metabolites, and glucuronidated metabolites, as wells as primary and secondary bile acid metabolites.

Example 4

Effect of Chronic Kidney Disease (CKD) on the OAT1-Centered Network:

A CKD-associated metabolic network was constructed in Metscape based on 114 metabolites found to be associated with CKD in humans and/or animal models. As above, a metabolic network was then created which included the metabolites and their immediate neighbors, and the network was trimmed as described above to eliminate water, $CO_2$, ATP, NADH, peptides, etc. After the disease-associated metabolic network was created, it was compared with the OAT1-centered metabolic network.

Statistics:

To determine if the overall in-silico approach results in significant enrichment of metabolites known to have direct interaction with OAT1, a hypergeometric-based test was performed to calculate the various p-values. The hypergeometric calculation, which is based on certain assumptions, has been used in systems biological analyses for determining the probability of a result occurring just by chance (Mitrea et al., 2013). In addition, the hypergeometric test was also used to determine the significance of overlap between two metabolic networks, i.e. the OAT1 network and the CKD network (Wang et al., 2014; Zhang et al., 2013).

Metabolic Pathways Altered in Chronic Kidney Disease (CKD).

Chronic kidney disease (CKD) causes "uremic syndrome," which affects many metabolic pathways and is associated with the accumulation of so-called "uremic toxins" in the plasma. While the pathobiology of CKD and the basis of the symptoms of the uremic syndrome are not well understood, uremic toxins are believed to affect many aspects of metabolism in CKD. Many of these uremic toxins are organic ions, and there is in vitro and in vivo (knockout) evidence that they are transported by OAT1. For example, some of the small molecule uremic toxins of greatest clinical concern (e.g. indoxyl sulfate, p-cresol sulfate, kyurenic acid) are known OAT1 substrates; they also accumulate in Oat1 knockout mice. Indeed, it is believed that these are some of the major molecules removed by dialysis.

The expression of OAT1 is also known to be affected in animal models of kidney disease and in patients with diabetic nephropathy. Thus, in both animal and human data OAT1 has been implicated in the metabolic abnormalities associated with diabetic nephropathy, and Oat1 levels change in animal models of kidney disease. The application of targeted and untargeted metabolomics to patients with CKD and to animal models for this disease has made it possible to produce a list of metabolic alterations associated with CKD. This list includes metabolites involved in key metabolic pathways, uremic toxins, and molecules considered to be biomarkers of CKD. This list was used to generate a putative CKD-associated metabolic network and the CKD network was built based on this review of many metabolic studies using animal models and clinical data. After trimming, this CKD network contained a total of 322 metabolites.

Overlap of the OAT1-centered metabolic network with the CKD-associated network. To evaluate the potential role of OAT1 in the metabolic alterations of CKD, the OAT1-centered network was compared with the CKD network (FIG. 8). It was found that the two networks overlapped significantly (p-value <0.001). While this does not necessarily imply a causal connection between OAT1 function and CKD, it indicates that the metabolic network regulated by OAT1 significantly overlaps with the set of metabolites that are affected in CKD. There were 113 overlapping metabolites between the models (44% of metabolites in the OAT1-centered metabolic network). Pathway enrichment analysis revealed effects on a number of metabolic pathways by these 113 overlapping metabolites. The statistically significantly enriched metabolic pathways included the urea cycle and purine metabolism. Furthermore, there is also a list of putative uremic toxins separately compiled by the EUTox working group, which has examined the considerable functional and other data available on molecules implicated in CKD. The EUTox list includes molecules believed to be related to the pathobiology of CKD, its clinical manifestations, and the altered metabolism of CKD. Based on this, the list of EUT uremic toxins was compared to the list of metabolites found in all three networks (i.e., OAT1-centered, CKD-associated and OAT1-centered/CKD-associated overlapping network) and all of these networks were found to be significantly enriched for uremic toxins (p-value <0.01).

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining a drug therapy or efficacy, drug transporter-associated metabolic disease or disorder, or metabolic side effect in a subject, the method comprising
   obtaining a biological sample from a subject, wherein the sample comprises a plurality of metabolites;
   detecting an amount of each of the plurality of metabolites in the biological sample obtained from the subject,
   identifying a single or plurality of drug transporter-associated metabolomics pathways by comparing each of the plurality of metabolites in the biological sample with drug-transport protein substrates associated with the single or plurality of drug transport-associated metabolomic pathways to obtain an drug-transport protein profile for the subject;
   determining a pharmacophore profile for the subject for each drug-transport protein in the drug-transport protein profile;
   determining a pharmacophore associated with one or a plurality of drugs to be administered to the subject; and determining, based on the pharmacophore associated with the one or plurality of drugs and the pharmacophore profile for the subject, the effect a drug will have on metabolism in a subject.

2. The method of claim 1, further comprising determining a difference between a control and subject's metabolites, wherein a difference is indicative of a drug transport-associated metabolic disease or disorder associated with a pharmacophore.

3. The method of claim 1, further comprising identifying a drug therapy for the subject based upon the pharmacophore associated with the one or plurality of drugs and the pharmacophore profile of the subject.

4. The method of claim 1, wherein the drug transport-associated metabolomics pathways are identified by analyzing a wild-type metabolic profile and a selected drug-transporter knockout metabolic profile and/or the metabolomics profile of a subject with altered expression and/or function of a drug transporter.

5. The method of claim 1, wherein a metabolite or set of metabolites is monitored in a drug therapy for a modulation of a drug transporter metabolic profile to determine an efficacy of the drug and/or the presence of metabolic side effects.

6. The method of claim 1, wherein the drug-transport protein profile comprises one or more SLC family of drug-transport proteins and/or one or more ABC family of drug-transport proteins.

7. The method of claim 6, wherein the one or mom pharmacophore associated with the one or plurality of drugs are matched to the subject's drug-transport protein profile to identify a drug therapy.

* * * * *

UNITED STATES PATENT AND TRADEMARK OFFICE
CERTIFICATE OF CORRECTION

| | | |
|---|---|---|
| PATENT NO. | : 11,004,539 B2 | Page 1 of 1 |
| APPLICATION NO. | : 15/436567 | |
| DATED | : May 11, 2021 | |
| INVENTOR(S) | : Sanjay K. Nigam and Henry C. Liu | |

It is certified that error appears in the above-identified patent and that said Letters Patent is hereby corrected as shown below:

In the Specification

In Column 1, Lines 15-18, please replace with the following:
--This invention was made with government support under GM098449, HD071600, and GM010498 awarded by the National Institutes of Health. The government has certain rights in the invention.--

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*